(12) United States Patent
Hills et al.

(10) Patent No.: US 7,563,749 B2
(45) Date of Patent: Jul. 21, 2009

(54) HERBICIDE-SAFENER COMBINATION

(75) Inventors: Martin Hills, Idstein (DE); Erwin Hacker, Hochheim (DE); Hansjörg Krähmer, Hofheim (DE); Chris Rosinger, Hofheim (DE); Udo Bickers, Wietmarschen (DE); Frank Ziemer, Kriftel (DE); Christian Waldraff, Bad Vilbel (DE); Hansjörg Dietrich, Hofheim (DE); Lothar Willms, Hofheim (DE); Dieter Feucht, Kelkheim (DE); Klaus-Helmut Müller, Düsseldorf (DE); Ulrich Philipp, Lees Summit, MO (US)

(73) Assignee: Bayer CropScience AG, Frankfurt am Main (DE)

( * ) Notice: Subject to any disclaimer, the term of this patent is extended or adjusted under 35 U.S.C. 154(b) by 505 days.

(21) Appl. No.: 11/090,985

(22) Filed: Mar. 25, 2005

(65) Prior Publication Data
US 2005/0233904 A1 Oct. 20, 2005

(30) Foreign Application Priority Data
Mar. 27, 2004 (DE) .......... 10 2004 015 140
Jun. 30, 2004 (DE) .......... 10 2004 031 345

(51) Int. Cl.
*C07D 413/10* (2006.01)
*C07D 413/14* (2006.01)
*A01N 43/54* (2006.01)
*A01N 43/88* (2006.01)
*C07D 413/02* (2006.01)
*C07D 413/06* (2006.01)
*A01N 43/72* (2006.01)

(52) U.S. Cl. .......... 504/223; 544/65
(58) Field of Classification Search .......... 504/239
See application file for complete search history.

(56) References Cited

U.S. PATENT DOCUMENTS

| | | | |
|---|---|---|---|
| 4,021,224 A | 5/1977 | Pallos et al. | |
| 4,021,229 A | 5/1977 | Arneklev et al. | |
| 4,137,070 A | 1/1979 | Pallos et al. | |
| 4,601,745 A | 7/1986 | Moser | |
| 4,623,727 A | 11/1986 | Hübele | |
| 4,639,266 A | 1/1987 | Heubach et al. | |
| 4,881,966 A | 11/1989 | Nyffeler et al. | |
| 4,891,057 A | 1/1990 | Sohn et al. | |
| 4,902,340 A | 2/1990 | Hubele | |
| 5,215,570 A | 6/1993 | Burckhardt et al. | |
| 5,314,863 A | 5/1994 | Löher et al. | |
| 5,380,852 A | 1/1995 | Schütze et al. | |
| 5,401,700 A | 3/1995 | Sohn et al. | |
| 5,476,936 A * | 12/1995 | Philipp et al. | 504/223 |
| 5,488,027 A | 1/1996 | Bauer et al. | |
| 5,516,750 A | 5/1996 | Willms et al. | |
| 5,700,758 A | 12/1997 | Rösch et al. | |
| 5,739,079 A | 4/1998 | Holdgrün et al. | |
| 6,235,680 B1 | 5/2001 | Ziemer et al. | |
| 6,251,827 B1 | 6/2001 | Ziemer et al. | |

FOREIGN PATENT DOCUMENTS

| | | |
|---|---|---|
| DE | 43 23 122 A1 | 1/1995 |
| EP | 0 086 750 | 8/1983 |
| EP | 0 094 349 | 11/1983 |
| EP | 0 149 974 | 7/1985 |
| EP | 0 174 562 | 3/1986 |
| EP | 0 191 736 | 8/1986 |
| EP | 0 269 806 | 6/1988 |
| EP | 0 333 131 | 9/1989 |
| EP | 0 346 620 | 12/1989 |
| EP | 0 365 484 | 4/1990 |
| EP | 0 492 366 | 7/1992 |
| EP | 0 582 198 | 2/1994 |
| EP | 1 008 297 A2 | 6/2000 |
| GB | 2 121 403 | 12/1983 |
| WO | WO-91/07874 | 6/1991 |
| WO | WO-91/08202 | 6/1991 |
| WO | WO-95/07897 | 3/1995 |
| WO | WO-97/45016 | 12/1997 |
| WO | WO-99/16744 | 4/1999 |
| WO | WO-02/34048 | 5/2002 |

OTHER PUBLICATIONS

Davies et al., Pesticide Science, 1999, Society of Chemical Industry, vol. 55, pp. 1043-1058.*
U.S. Appl. No. 11/090,374, filed Mar. 25, 2005.
U.S. Appl. No. 11/090,424, filed Mar. 25, 2005.

* cited by examiner

*Primary Examiner*—Johann R Richter
*Assistant Examiner*—Courtney Brown
(74) *Attorney, Agent, or Firm*—Connolly Bove Lodge & Hutz LLP

(57) ABSTRACT

The present invention relates to a herbicide-safener combination, comprising
(A) one or more compounds of the formula (I) or salts thereof

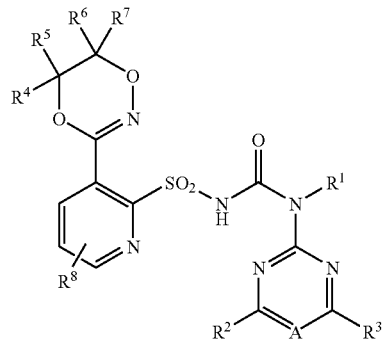

(I)

as defined in the application
and
(B) one or more safeners.

21 Claims, No Drawings

HERBICIDE-SAFENER COMBINATION

The invention relates to the technical field of the crop protection compositions, in particular herbicide-safener combinations, which are highly suitable for use against harmful plants in crops of useful plants.

U.S. Pat. No. 5,476,936 discloses herbicidally active compounds controlling a broad spectrum of weeds. However, some of these active compounds are not entirely compatible with some important crop plants such as cereals. Accordingly, in some crops, they cannot be employed such that the desired broad herbicidal activity against harmful plants is ensured.

It was an object of the present invention to provide herbicidal compositions in which the selectivity of the abovementioned herbicides in important crop plants is increased. Surprisingly, this object is achieved by the herbicide-safener combination of the present invention.

Accordingly, the present invention provides a herbicide-safener combination, comprising
(A) one or more compounds of the formula (I) or salts thereof (I)

in which
A is nitrogen or a $CR^{11}$ grouping,
  where
  $R^{11}$ is hydrogen, alkyl, halogen and haloalkyl,
$R^1$ is hydrogen or an optionally substituted radical from the group consisting of alkyl, alkoxy, alkoxyalkyl, alkenyl, akynyl, cycloalkyl, cycloalkylalkyl, aralkyl and aryl,
$R^2$ is hydrogen, halogen or in each case optionally halogen-substituted alkyl, alkoxy, alkylthio, alkylamino or dialkylamino having in each case 1 to 6 carbon atoms,
$R^3$ is hydrogen, halogen or in each case optionally halogen-substituted alkyl, alkoxy, alkylthio, alkylamino or dialkylamino having in each case 1 to 6 carbon atoms,
$R^4$-$R^7$ independently of one another are hydrogen, halogen, cyano, thiocyanato or in each case optionally halogen-substituted alkyl, alkoxy, alkylthio, alkylsulfinyl, alkylsulfonyl, alkylamino, alkylcarbonyl, alkoxycarbonyl, alkylaminocarbonyl having in each case 1 to 3 carbon atoms,
$R^8$ is hydrogen, halogen, cyano, thiocyanato or in each case optionally halogen-substituted alkyl, alkoxy, alkylthio, alkylsulfinyl, alkylsulfonyl, alkylamino, alkylcarbonyl, alkoxycarbonyl, alkylaminocarbonyl having in each case 1 to 3 carbon atoms,
where in the radicals mentioned above the alkyl and alkylene groups may in each case contain 1 to 6 carbon atoms, the alkenyl and alkynyl groups may in each case contain 2 to 6 carbon atoms, the cycloalkyl groups may in each case contain 3 to 6 carbon atoms and the aryl groups may in each case contain 6 or 10 carbon atoms; and (B) one or more safeners.

The herbicide-safener combinations according to the invention may additionally comprise further components, for example crop protection agents of a different type and/or formulation auxiliaries and/or additives customary in crop protection, or they may be employed together with these.

The herbicides (A) and the safeners (B) can be applied in a known manner, for example together (for example as a coformulation or as a tank mix), or else as a split application, for example to the plants, parts of plants, plant seeds or to the area on which the plants grow. It is possible, for example, to apply the individual active compounds or the herbicide-safener combination in a plurality of portions (sequential application), for example as pre-emergence applications followed by post-emergence applications or as early post-emergence applications followed by applications at medium or late post-emergence. Preference is given here to the simultaneous or nearly simultaneous application of the active compounds of the combination in question. It is also possible to use the individual active compounds or the herbicide-safener combination for seed dressing.

The above formula (I) encompasses all stereoisomers and mixtures thereof, including, in particular, also racemic mixtures and—if enantiomers are possible—the respective biologically active enantiomer.

The compounds of the formula (I) and their salts are known, as is their preparation, for example from U.S. Pat. No. 5,476,936, which is incorporated into the present description by way of reference.

Preferred herbicides (A) are compounds of the formula (I) and salts thereof
in which
A is nitrogen or a CH grouping,
$R^1$ is hydrogen or an optionally halogen-substituted radical from the group consisting of alkyl, alkoxy, alkoxyalkyl, alkenyl and alkynyl having in each case up to 3 carbon atoms,
$R^2$ is hydrogen, halogen or in each case halogen-substituted alkyl, alkoxy, alkylthio, alkylamino or dialkylamino having in each case 1 to 3 carbon atoms in the alkyl radicals,
$R^3$ is hydrogen, halogen or in each case halogen-substituted alkyl, alkoxy, alkylthio, alkylamino or dialkylamino having in each case 1 to 3 carbon atoms in the alkyl radicals,
$R^4$-$R^7$ independently of one another are hydrogen, halogen, cyano, thiocyanato or in each case optionally halogen-substituted alkyl, alkoxy, alkylthio, alkylsulfinyl, alkylsulfonyl, alkylamino, alkyl-carbonyl, alkoxycarbonyl, or alkylaminocarbonyl having in each case 1 to 3 carbon atoms in the alkyl radicals,
$R^8$ is hydrogen, halogen, cyano, thiocyanato or in each case optionally halogen-substituted alkyl, alkoxy, alkylthio, alkylsulfinyl, alkylsulfonyl, alkylamino, alkylcarbonyl, alkoxycarbonyl or alkylaminocarbonyl having in each case 1 to 3 carbon atoms in the alkyl radicals.

Preferred herbicides (A) are also salts which are obtained by customary processes from compounds of the formula (I) and bases, such as, for example, sodium hydroxide, sodium hydride, sodium amide and sodium carbonate, potassium hydroxide, potassium hydride, potassium amide and potassium carbonate or calcium hydroxide, calcium hydride, calcium amide and calcium carbonate, sodium $C_1$-$C_4$-alkoxides or potassium $C_1$-$C_4$-alkoxides, ammonia, $C_1$-$C_4$-alkylamines, di-($C_1$-$C_4$-alkyl)amines or tri-($C_1$-$C_4$)amines.

Particularly preferred herbicides (A) are compounds of the formula (I) and salts thereof
in which
A is nitrogen or a CH group,
$R^1$ is hydrogen, methyl, ethyl, methoxy, methoxymethyl or ethoxy,
$R^2$ is hydrogen, chlorine, methyl, ethyl, trifluoromethyl, methoxy, ethoxy, difluoromethoxy, methylthio, methylamino or dimethylamino,
$R^3$ is hydrogen, chlorine, methyl, ethyl, trifluoromethyl, methoxy, ethoxy, difluoromethoxy, methylthio, methylamino or dimethylamino,
$R^4$—$R^7$ independently of one another are hydrogen, fluorine, chlorine, cyano, or in each case optionally fluorine- or chlorine-substituted methyl, methylthio, methylsulfinyl, methylsulfonyl, methoxycarbonyl and ethoxycarbonyl, preferably hydrogen,
$R^8$ is hydrogen, fluorine, chlorine, bromine, cyano, or in each case optionally chlorine- or fluorine-substituted methyl, methoxy, ethoxy, methylthio, ethylthio, methylsulfinyl, ethylsulfinyl, methylsulfonyl, ethylsulfonyl, methylamino or dimethylamino, preferably hydrogen.

Particularly preferred herbicides (A) are compounds of the formula (I) and salts thereof, in particular their alkali metal salts,
in which
A is nitrogen,
$R^1$ is hydrogen or methyl,
$R^2$ is hydrogen, chlorine, methyl, ethyl, trifluoromethyl, methoxy, ethoxy, difluoromethoxy, methylthio, methylamino or dimethylamino,
$R^3$ is hydrogen, chlorine, methyl, ethyl, trifluoromethyl, methoxy, ethoxy, difluoromethoxy, methylthio, methylamino or dimethylamino,
$R^4$-$R^7$ are hydrogen
$R^8$ is hydrogen.

Other particularly preferred herbicides (A) are compounds of the formula (I) and salts thereof, in particular their alkali metal salts,
in which
A is a CH grouping,
$R^1$ is hydrogen or methyl,
$R^2$ is hydrogen, chlorine, methyl, ethyl, trifluoromethyl, methoxy, ethoxy, difluoromethoxy, methylthio, methylamino or dimethylamino,
$R^3$ is hydrogen, chlorine, methyl, ethyl, trifluoromethyl, methoxy, ethoxy, difluoromethoxy, methylthio, methylamino or dimethylamino,
$R^4$-$R^7$ are hydrogen,
$R^8$ is hydrogen.

The general or preferred radical definitions given above can be combined with one another as desired, i.e. including combinations between the given preferred ranges.

The hydrocarbon radicals mentioned in the radical definitions, such as alkyl, alkenyl or alkynyl, can be straight-chain or branched even if this is not explicitly stated, including in combination with heteroatoms, such as in alkoxy, alkylthio, haloalkyl or alkylamino.

If desired, salts may be prepared from the compounds of the formula (I), for example metal salts, such as alkali metal (for example Na, K) salts or alkaline earth metal (for example Ca, Mg) salts or ammonium or amine salts. Such salts are obtained in a simple manner by customary methods for forming salts, for example by dissolving or dispersing a compound of the formula (I) in a suitable diluent, such as, for example, methylene chloride, acetone, tert-butyl methyl ether or toluene, and adding a suitable base. The salts can then—if appropriate after prolonged stirring—be isolated by concentration or filtration with suction.

Examples of compounds used as herbicide (A) are mentioned in table 1 below, where the following abbreviations are used:
m.p.=melting point
decomp. or d.=with decomposition
(+)=the indicated melting point (m.p.) refers to the respective sodium salt, i.e. the corresponding compound in which the hydrogen of the —$SO_2$—NH— group is replaced by sodium.

TABLE 1

Examples of compounds of the formula (I) where $R^4 = R^5 = R^6 = R^7 = R^8 = H$:

| Ex. No. | $R^1$ | A | $R^2$ | $R^3$ | m.p. (° C.) |
|---|---|---|---|---|---|
| I-1 | H | CH | $OCH_3$ | $OC_2H_5$ | 154 |
| I-2 | H | CH | $OCH_3$ | $CH_3$ | |
| I-3 | H | CH | $OHC_3$ | $CH_3$ | 180-181(+) |
| I-4 | H | CH | $OCH_3$ | $C_2H_5$ | |
| I-5 | H | CH | $OCH_3$ | $CF_3$ | |
| I-6 | H | CH | $OCH_3$ | $OCF_2H$ | |
| I-7 | H | CH | $OCH_3$ | $NHCH_3$ | |
| I-8 | H | CH | $OCH_3$ | $N(CH_3)_2$ | 199.5 |
| I-9 | H | CH | $OCH_3$ | Cl | 110-111 |
| I-10 | H | CH | $OCH_3$ | Cl | 175-178(+) |
| I-11 | H | CH | $OCH_3$ | $OCH_3$ | 167-168 |
| I-12 | H | CH | $OCH_3$ | $OCH_3$ | 171-172(+) |
| I-13 | H | CH | $OC_2H_5$ | $OC_2H_5$ | |
| I-14 | H | CH | $OC_2H_5$ | $OC_2H_5$ | 152-154(+) |
| I-15 | H | CH | $OC_2H_5$ | $CH_3$ | |
| I-16 | H | CH | $OC_2H_5$ | $C_2H_5$ | |
| I-17 | H | CH | $OC_2H_5$ | $CF_3$ | |
| I-18 | H | CH | $OC_2H_5$ | $OCF_2H$ | |
| I-19 | H | CH | $OC_2H_5$ | $NHCH_3$ | |
| I-20 | H | CH | $OC_2H_5$ | $N(CH_3)_2$ | |
| I-21 | H | CH | $OC_2H_5$ | Cl | 158-159 |
| I-22 | H | CH | $OC_2H_5$ | Cl | 213(+) |
| I-23 | H | CH | $CH_3$ | $CH_3$ | 153 |
| I-24 | H | CH | $CH_3$ | $C_2H_5$ | |
| I-25 | H | CH | $CH_3$ | $CF_3$ | |
| I-26 | H | CH | $CH_3$ | $OCF_2H$ | |
| I-27 | H | CH | $CH_3$ | $NHCH_3$ | |
| I-28 | H | CH | $CH_3$ | $N(CH_3)_2$ | |
| I-29 | H | CH | $CH_3$ | Cl | 108-109 |
| I-30 | H | CH | $CH_3$ | Cl | >300(+) |
| I-31 | H | CH | $C_2H_5$ | $C_2H_5$ | |
| I-32 | H | CH | $C_2H_5$ | $CF_3$ | |
| I-33 | H | CH | $C_2H_5$ | $OCF_2H$ | |
| I-34 | H | CH | $C_2H_5$ | $NHCH_3$ | |
| I-35 | H | CH | $C_2H_5$ | Cl | |
| I-36 | H | CH | $CF_3$ | $CF_3$ | |
| I-37 | H | CH | $CF_3$ | $OCF_2H$ | |
| I-38 | H | CH | $CF_3$ | $NHCH_3$ | |
| I-39 | H | CH | $CF_3$ | $N(CH_3)_2$ | |
| I-40 | H | CH | $CF_3$ | Cl | |
| I-41 | H | CH | $OCF_2H$ | $OCF_2H$ | |
| I-42 | H | CH | $OCF_2H$ | $NHCH_3$ | |
| I-43 | H | CH | $OCF_2H$ | $N(CH_3)_2$ | |
| I-44 | H | CH | $OCF_2H$ | Cl | |
| I-45 | H | CH | $NHCH_3$ | $NHCH_3$ | |
| I-46 | H | CH | $NHCH_3$ | $N(CH_3)_2$ | |
| I-47 | H | CH | $NHCH_3$ | Cl | |
| I-48 | H | CH | $N(CH_3)_2$ | $N(CH_3)_2$ | |
| I-49 | H | CH | $N(CH_3)_2$ | Cl | |
| I-50 | H | CH | Cl | Cl | |
| I-51 | H | N | $OCH_3$ | $OCH_3$ | 255 |
| I-52 | H | N | $OCH_3$ | $OCH_3$ | 159-162(+) |
| I-53 | H | N | $OCH_3$ | $OC_2H_5$ | |
| I-54 | H | N | $OCH_3$ | $CH_3$ | |
| I-55 | H | N | $OCH_3$ | $C_2H_5$ | |
| I-56 | H | N | $OCH_3$ | $CF_3$ | |
| I-57 | H | N | $OCH_3$ | $OCF_2H$ | |
| I-58 | H | N | $OCH_3$ | $NHCH_3$ | |

TABLE 1-continued

Examples of compounds of the formula (I) where
$R^4 = R^5 = R^6 = R^7 = R^8 = H$:

| Ex. No. | $R^1$ | A | $R^2$ | $R^3$ | m.p. (° C.) |
|---|---|---|---|---|---|
| I-59 | H | N | OCH$_3$ | N(CH$_3$)$_2$ | |
| I-60 | H | N | OCH$_3$ | N(CH$_3$)$_2$ | 156$^{(+)}$ |
| I-61 | H | N | OCH$_3$ | Cl | |
| I-62 | H | N | OC$_2$H$_5$ | OC$_2$H$_5$ | |
| I-63 | H | N | OC$_2$H$_5$ | CH$_3$ | |
| I-64 | H | N | OC$_2$H$_5$ | C$_2$H$_5$ | |
| I-65 | H | N | OC$_2$H$_5$ | CF$_3$ | |
| I-66 | H | N | OC$_2$H$_5$ | OCF$_2$H | |
| I-67 | H | N | OC$_2$H$_5$ | NHCH$_3$ | |
| I-68 | H | N | OC$_2$H$_5$ | N(CH$_3$)$_2$ | |
| I-69 | H | N | OC$_2$H$_5$ | Cl | |
| I-70 | H | N | OC$_2$H$_5$ | Cl | 213$^{(+)}$ |
| I-71 | H | N | CH$_3$ | CH$_3$ | |
| I-72 | H | N | CH$_3$ | C$_2$H$_5$ | |
| I-73 | H | N | CH$_3$ | CF$_3$ | |
| I-74 | H | N | CH$_3$ | OCF$_2$H | |
| I-75 | H | N | CH$_3$ | NHCH$_3$ | |
| I-76 | H | N | CH$_3$ | N(CH$_3$)$_2$ | |
| I-77 | H | N | CH$_3$ | Cl | |
| I-78 | H | N | C$_2$H$_5$ | C$_2$H$_5$ | |
| I-79 | H | N | C$_2$H$_5$ | CF$_3$ | |
| I-80 | H | N | C$_2$H$_5$ | OCF$_2$H | |
| I-81 | H | N | C$_2$H$_5$ | NHCH$_3$ | |
| I-82 | H | N | C$_2$H$_5$ | Cl | |
| I-83 | H | N | CF$_3$ | CF$_3$ | |
| I-84 | H | N | CF$_3$ | OCF$_2$H | |
| I-85 | H | N | CF$_3$ | NHCH$_3$ | |
| I-86 | H | N | CF$_3$ | N(CH$_3$)$_2$ | |
| I-87 | H | N | CF$_3$ | Cl | |
| I-88 | H | N | OCF$_2$H | OCF$_2$H | |
| I-89 | H | N | OCF$_2$H | NHCH$_3$ | |
| I-90 | H | N | OCF$_2$H | N(CH$_3$)$_2$ | |
| I-91 | H | N | OCF$_2$H | Cl | |
| I-92 | H | N | NHCH$_3$ | NHCH$_3$ | |
| I-93 | H | N | NHCH$_3$ | N(CH$_3$)$_2$ | |
| I-94 | H | N | NHCH$_3$ | Cl | |
| I-95 | H | N | N(CH$_3$)$_2$ | N(CH$_3$)$_2$ | |
| I-96 | H | N | N(CH$_3$)$_2$ | Cl | |
| I-97 | H | N | Cl | Cl | |
| I-98 | CH$_3$ | N | OCH$_3$ | OCH$_3$ | |
| I-99 | CH$_3$ | N | OCH$_3$ | OC$_2$H$_5$ | |
| I-100 | CH$_3$ | N | OCH$_3$ | CH$_3$ | |
| I-101 | CH$_3$ | N | OCH$_3$ | C$_2$H$_5$ | |
| I-102 | CH$_3$ | N | OCH$_3$ | CF$_3$ | |
| I-103 | CH$_3$ | N | OCH$_3$ | OCF$_2$H | |
| I-104 | CH$_3$ | N | OCH$_3$ | NHCH$_3$ | |
| I-105 | CH$_3$ | N | OCH$_3$ | N(CH$_3$)$_2$ | |
| I-106 | CH$_3$ | N | OCH$_3$ | Cl | |
| I-107 | CH$_3$ | N | OC$_2$H$_5$ | OC$_2$H$_5$ | |
| I-108 | CH$_3$ | N | OC$_2$H$_5$ | CH$_3$ | |
| I-109 | CH$_3$ | N | OC$_2$H$_5$ | C$_2$H$_5$ | |
| I-110 | CH$_3$ | N | OC$_2$H$_5$ | CF$_3$ | |
| I-111 | CH$_3$ | N | OC$_2$H$_5$ | OCF$_2$H | |
| I-112 | CH$_3$ | N | OC$_2$H$_5$ | NHCH$_3$ | |
| I-113 | CH$_3$ | N | OC$_2$H$_5$ | N(CH$_3$)$_2$ | |
| I-114 | CH$_3$ | N | OC$_2$H$_5$ | Cl | |
| I-115 | CH$_3$ | N | CH$_3$ | CH$_3$ | |
| I-116 | CH$_3$ | N | CH$_3$ | C$_2$H$_5$ | |
| I-117 | CH$_3$ | N | CH$_3$ | CF$_3$ | |
| I-118 | CH$_3$ | N | CH$_3$ | OCF$_2$H | |
| I-119 | CH$_3$ | N | CH$_3$ | NHCH$_3$ | |
| I-120 | CH$_3$ | N | CH$_3$ | N(CH$_3$)$_2$ | |
| I-121 | CH$_3$ | N | CH$_3$ | Cl | |
| I-122 | CH$_3$ | N | C$_2$H$_5$ | C$_2$H$_5$ | |
| I-123 | CH$_3$ | N | C$_2$H$_5$ | CF$_3$ | |
| I-124 | CH$_3$ | N | C$_2$H$_5$ | OCF$_2$H | |
| I-125 | CH$_3$ | N | C$_2$H$_5$ | NHCH$_3$ | |
| I-126 | CH$_3$ | N | C$_2$H$_5$ | Cl | |
| I-127 | CH$_3$ | N | CF$_3$ | CF$_3$ | |
| I-128 | CH$_3$ | N | CF$_3$ | OCF$_2$H | |
| I-129 | CH$_3$ | N | CF$_3$ | NHCH$_3$ | |
| I-130 | CH$_3$ | N | CF$_3$ | N(CH$_3$)$_2$ | |
| I-131 | CH$_3$ | N | CF$_3$ | Cl | |
| I-132 | CH$_3$ | N | OCF$_2$H | OCF$_2$H | |
| I-133 | CH$_3$ | N | OCF$_2$H | NHCH$_3$ | |
| I-134 | CH$_3$ | N | OCF$_2$H | N(CH$_3$)$_2$ | |
| I-135 | CH$_3$ | N | OCF$_2$H | Cl | |
| I-136 | CH$_3$ | N | NHCH$_3$ | NHCH$_3$ | |
| I-137 | CH$_3$ | N | NHCH$_3$ | N(CH$_3$)$_2$ | |
| I-138 | CH$_3$ | N | NHCH$_3$ | Cl | |
| I-139 | CH$_3$ | N | N(CH$_3$)$_2$ | N(CH$_3$)$_2$ | |
| I-140 | CH$_3$ | N | N(CH$_3$)$_2$ | Cl | |
| I-141 | CH$_3$ | N | Cl | Cl | |
| I-142 | H | N | N(CH$_3$)$_2$ | OCH$_2$CF$_3$ | 158 |
| I-143 | H | CH | Cl | OCH$_2$CF$_3$ | 204-205 |
| I-144 | H | CH | Cl | OCH$_2$CF$_3$ | |
| I-145 | H | CH | Cl | OCH$_2$CF$_3$ | 207$^{(+)}$ |

The herbicides (A) inhibit the enzyme acetolactate synthase (ALS) and thus the protein synthesis in plants. The application rate of the herbicides (A) may vary within a wide range depending on external conditions, such as temperature and humidity, and the type of herbicide used, for example between 0.001 g and 500 g of AS/ha (hereinbelow, AS/ha means "active substance per hectare"=based on 100% pure active compound). On application using applications rates of from 0.01 g to 200 g of As/ha of the herbicides (A), preferably the compounds I-1 to I-145, a relatively broad spectrum of harmful plants, for example annual and perennial monocotyledonous or dicotyledonous weeds and also unwanted crop plants is controlled by the pre-emergence and the post-emergence method In the combinations according to the invention, the application rates are generally lower, for example in the range from 0.001 g to 100 g of AS/ha, preferably from 0.005 g to 50 g of AS/ha, particularly preferably from 0.01 g to 9 g of AS/ha.

The herbicides (A) are suitable for controlling harmful plants, for example in crop plants, for example in economically important farm crops, for example monocotyledonous farm crops, such as cereals (for example wheat, barley, rye, oats), rice, corn, millet, or dicotyledonous farm crops, such as sugar beet, oil seed rape, cotton, sunflower and legumes, for example of the genera *glycine* (for example *Glycine max.* (soybean), such as non-transgenic *Glycine max.* (for example conventional cultivars, such as STS cultivars) or transgenic *Glycine max.* (for example RR soybean or LL soybean) and crossbreeds thereof), *Phaseolus, Pisum, Vicia* and *Arachis* or vegetable crops from various botanical groups, such as potato, leek, cabbage, carrot, tomato, onion, and also permanent crops and plantation crops, such as pome fruit and stone fruit, berry fruit, grapevines, Hevea, bananas, sugar cane, coffee, tea, citrus fruit, nut plantations, lawn, palm plantations and forest plantations. These crops are also preferred for the application of the herbicide-safener combinations (A)+(B) according to the invention; particularly preferred is the application in cereals (for example wheat, barley, rye, oats), rice, corn, millet, sugar beet, sugar cane, sunflower, oil seed rape and cotton. The herbicide-safener combinations (A)+(B) can also be used in tolerant and non-tolerant mutant crops and in tolerant and non-tolerant transgenic crops, for example of corn, rice, cereals, oil seed rape and soybean, for example those which are resistant to imidazolinone herbicides, atrazine, glufosinate or glyphosate.

The safeners present as component (B) are understood to be compounds which are capable of reducing phytotoxic actions of crop protection agents such as herbicides in crop plants.

The safeners (B) are preferably selected from the group consisting of:

a) compounds of the formulae (II) to (IV),

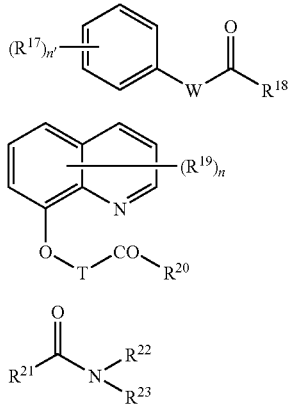

where the symbols and indices are as defined below:

n' is a natural number from 0 to 5, preferably 0 to 3;

T is a $(C_1-C_2)$-alkanediyl chain which is unsubstituted or substituted by one or two $(C_1-C_4)$alkyl radicals or by $[(C_1-C_3)$-alkoxy]carbonyl;

W is an unsubstituted or substituted divalent heterocyclic radical from the group of the partially unsaturated or aromatic five-membered heterocycles having 1 to 3 nitrogen or oxygen hetero ring atoms, where the ring contains at least one nitrogen atom and at most one oxygen atom, preferably a radical from the group consisting of (W1) to (W4),

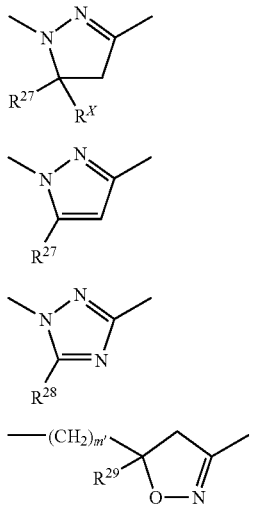

m' is 0 or 1;

$R^{17}$, $R^{19}$ are identical or different and are halogen, $(C_1-C_4)$-alkyl, $(C_1-C_4)$-alkoxy, nitro or $(C_1-C_4)$-haloalkyl;

$R^{18}$, $R^{20}$ are identical or different and are $OR^{24}$, $SR^{24}$ or $NR^{24}R^{25}$ or a saturated or unsaturated 3- to 7-membered heterocycle having at least one nitrogen atom and up to 3 heteroatoms, preferably from the group consisting of oxygen and sulfur, which is attached to the carbonyl group in (II) or (III) via the nitrogen atom and which is unsubstituted or substituted by radicals from the group consisting of $(C_1-C_4)$-alkyl, $(C_1-C_4)$-alkoxy and optionally substituted phenyl, preferably a radical of the formula $OR^{24}$, $NHR^{25}$ or $N(CH_3)_2$, in particular of the formula $OR^{24}$;

$R^{24}$ is hydrogen or an unsubstituted or substituted aliphatic hydrocarbon radical having preferably a total of 1 to 18 carbon atoms;

$R^{25}$ is hydrogen, $(C_1-C_6)$-alkyl, $(C_1-C_6)$-alkoxy or substituted or unsubstituted phenyl;

$R^X$ is H, $(C_1-C_8)$-alkyl, $(C_1-C_8)$-haloalkyl, $(C_1-C_4)$-alkoxy-$(C_1-C_8)$-alkyl, cyano or $COOR^{26}$, where $R^{26}$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R^{27}$, $R^{28}$, $R^{29}$ are identical or different and are hydrogen, $(C_1-C_8)$-alkyl, $(C_1-C_8)$-haloalkyl, $(C_3-C_{12})$-haloalkyl or substituted or unsubstituted phenyl;

$R^{21}$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl preferably dichloromethyl;

$R^{22}$, $R^{23}$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R^{22}$ and $R^{23}$ together form a substituted or unsubstituted heterocyclic ring, preferably an oxazolidine, thiazolidine, piperidine, morpholine, hexahydropyrimidine or benzoxazine ring;

b) one or more compounds from the group consisting of:
1,8-naphthalic anhydride,
methyl diphenylmethoxyacetate,
1-(2-chlorobenzyl)-3-(1-methyl-1-phenylethyl)urea (cumyluron),
O,O-diethyl S-2-ethylthioethyl phosphorod ithioate (disulfoton),
4-chlorophenyl methylcarbamate (mephenate),
O,O-diethyl O-phenyl phosphorothioate (dietholate),
4-carboxy-3,4-dihydro-2H-1-benzopyran-4-acetic acid (CL-304415, CAS-Regno: 31541-57-8),
cyanomethoxyimino(phenyl)acetonitrile (cyometrinil),
1,3-dioxolan-2-ylmethoxyimino(phenyl)acetonitrile (oxabetrinil),
4'-chloro-2,2,2-trifluoroacetophenone O-1,3-dioxolan-2-ylmethyloxime (fluxofenim),
4,6-dichloro-2-phenylpyrimidine (fenclorim),
benzyl 2-chloro-4-trifluoromethyl-1,3-thiazole-5-carboxylate (flurazole),
2-dichloromethyl-2-methyl-1,3-dioxolane (MG-191),
N-(4-methylphenyl)-N'-(1-methyl-1-phenylethyl)urea (dymron),
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor) and their salts and esters, preferably $(C_1-C_8)$ esters;

c) N-acylsulfonamides of the formula (V) and salts thereof

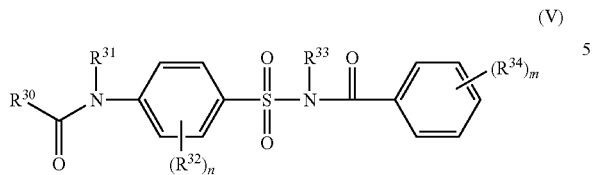

in which

R$^{30}$ is hydrogen, a hydrocarbon radical, a hydrocarbon oxy radical, a hydrocarbon thio radical or a heterocyclyl radical which is preferably attached via a carbon atom, where each of the 4 last-mentioned radicals is unsubstituted or substituted by one or more identical or different radicals from the group consisting of halogen, cyano, nitro, amino, hydroxyl, carboxyl, formyl, carboxamide, sulfonamide and radicals of the formula -Z$^a$-R$^a$,
  where each hydrocarbon moiety has preferably 1 to 20 carbon atoms and a carbon-containing radical R$^{30}$ including substitutents has preferably 1 to 30 carbon atoms;

R$^{31}$ is hydrogen or (C$_1$-C$_4$)-alkyl, preferably hydrogen, or

R$^{30}$ and R$^{31}$ together with the group of the formula —CO—N— are the radical of a 3- to 8-membered saturated or unsaturated ring;

R$^{32}$ are identical or different and are halogen, cyano, nitro, amino, hydroxyl, carboxyl, formyl, CONH$_2$, SO$_2$NH$_2$ or a radical of the formula -Z$^b$-R$^b$;

R$^{33}$ is hydrogen or (C$_1$-C$_4$)-alkyl, preferably H;

R$^{34}$ are identical or different and are halogen, cyano, nitro, amino, hydroxyl, carboxyl, CHO, CONH$_2$, SO$_2$NH$_2$ or a radical of the formula -Z$^c$-R$^c$;

R$^a$ is a hydrocarbon radical or a heterocyclyl radical, where each of the two last-mentioned radicals is unsubstituted or substituted by one or more identical or different radicals from the group consisting of halogen, cyano, nitro, amino, hydroxyl, mono- and di-[(C$_1$-C$_4$)-alkyl]-amino, or by an alkyl radical in which a plurality of, preferably 2 or 3, non-adjacent CH$_2$ groups are in each case replaced by an oxygen atom;

R$^b$, R$^c$ are identical or different and are a hydrocarbon radical or a heterocyclyl radical, where each of the two last-mentioned radicals is unsubstituted or substituted by one or more identical or different radicals from the group consisting of halogen, cyano, nitro, amino, hydroxyl, phosphoryl, halo-(C$_1$-C$_4$)-alkoxy, mono- and di-[(C$_1$-C$_4$)-alkyl]amino, or an alkyl radical in which a plurality of, preferably 2 or 3, non-adjacent CH$_2$ groups are in each case replaced by an oxygen atom;

Z$^a$ is a divalent group of the formula —O—, —S—, —CO—, —CS—, —CO—O—, —CO—S—, —O—CO—, —S—CO—, —SO—, —SO$_2$—, —NR*—, —CO—NR*—, —NR*—CO—, —SO$_2$—NR*— or —NR*—SO$_2$—, where the bond on the right of the divalent group in question is the bond to the radical R$^a$ and where the R* in the five last-mentioned radicals independently of one another are each H, (C$_1$-C$_4$)-alkyl or halo-(C$_1$-C$_4$)-alkyl;

Z$^b$, Z$^c$ independently of one another are a direct bond or a divalent group of the formula —O—, —S—, —CO—, —CS—, —CO—O—, —CO—S—, —O—CO—, —S—CO—, —SO—, —SO$_2$—, —NR*—, —SO$_2$—NR*—, —NR*—SO$_2$—, —CO—NR*— or —NR*—CO—, where the bond on the right of the divalent group in question is the bond to the radical R$^b$ or R$^c$ and where the R* in the 5 last-mentioned radicals independently of one another are each H, (C$_1$-C$_4$)-alkyl or halo-(C$_1$-C$_4$)-alkyl;

n is an integer from 0 to 4, preferably 0, 1 or 2, in particular 0 or 1, and m is an integer from 0 to 5, preferably 0, 1, 2 or 3, in particular 0, 1 or 2;

d) acylsulfamoylbenzamides of the formula (VI), if appropriate also in salt form,

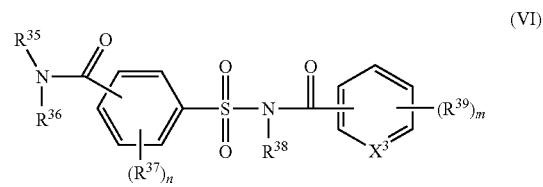

where

X$^3$ is CH or N;

R$^{35}$ is hydrogen, heterocyclyl or a hydrocarbon radical, where the two last-mentioned radicals are optionally substituted by one or more identical or different radicals from the group consisting of halogen, cyano, nitro, amino, hydroxyl, carboxyl, CHO, CHO, CONH$_2$, SO$_2$NH$_2$ and Z$^a$-R$^a$;

R$^{36}$ is hydrogen, hydroxyl, (C$_1$-C$_6$)-alkyl, (C$_2$-C$_6$)-alkenyl, (C$_2$-C$_6$)-alkynyl, (C$_1$-C$_6$)-alkoxy, (C$_2$-C$_6$)-alkenyloxy, where the five last-mentioned radicals are optionally substituted by one or more identical or different radicals from the group consisting of halogen, hydroxyl, hydroxyl, (C$_1$-C$_4$)-alkyl, (C$_1$-C$_4$)-alkoxy and (C$_1$-C$_4$)-alkylthio, or R$^{35}$ and R$^{36}$ together with the nitrogen atom that carries them are a 3- to 8-membered saturated or unsaturated ring;

R$^{37}$ is halogen, cyano, nitro, amino, hydroxyl, carboxyl, CHO, CONH$_2$, SO$_2$NH$_2$ or Z$^b$-R$^b$;

R$^{38}$ is hydrogen, (C$_1$-C$_4$)-alkyl, (C$_2$-C$_4$)-alkenyl or (C$_2$-C$_4$)-alkynyl;

R$^{39}$ is halogen, cyano, nitro, amino, hydroxyl, carboxyl, phosphoryl, CHO, CONH$_2$, SO$_2$NH$_2$ or Z$^c$-R$^c$;

R$^a$ is a (C$_2$-C$_{20}$)-alkyl radical whose carbon chain is interrupted once or more than once by oxygen atoms, is heterocyclyl or a hydrocarbon radical, where the two last-mentioned radicals are optionally substituted by one or more identical or different radicals from the group consisting of halogen, cyano, nitro, amino, hydroxyl, mono- and di-[(C$_1$-C$_4$)-alkyl]amino;

R$^b$, R$^c$ are identical or different and are a (C$_2$-C$_{20}$)-alkyl radical whose carbon chain is interrupted once or more than once by oxygen atoms, are heterocyclyl or a hydrocarbon radical, where the two last-mentioned radicals are optionally substituted by one or more identical or different radicals from the group consisting of halogen, cyano, nitro, amino, hydroxyl, phosphoryl, (C$_1$-C$_4$)-haloalkoxy, mono- and di-[(C$_1$-C$_4$)-alkyl]amino;

Z$^a$ is a divalent unit from the group consisting of O, S, CO, CS, C(O)O, C(O)S, SO, SO$_2$, NR$^d$, C(O)NR$^d$ and SO$_2$NR$^d$;

$Z^b$, $Z^c$ are identical or different and are a direct bond or a divalent unit from the group consisting of O, S, CO, CS, C(O)O, C(O)S, SO, SO$_2$, NR$^d$, SO$_2$NR$^d$ and C(O)NR$^d$;

$R^d$ is hydrogen, (C$_1$-C$_4$)-alkyl or (C$_1$-C$_4$)-haloalkyl;

n is an integer from 0 to 4, and m if X is CH, is an integer from 0 to 5, and if X is N, is an integer from 0 to 4;

e) compounds of the type of the acylsulfamoylbenzamides, for example of the formula (VII) below, which are known, for example, from WO 99/16744,

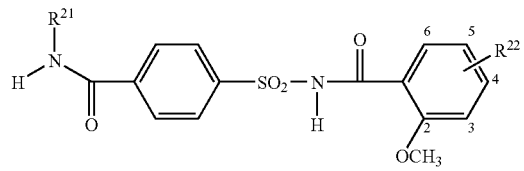

(VII)

for example those in which

R$^{21}$=cyclopropyl and R$^{22}$=H (S3-1=4-cyclopropylaminocarbonyl-N-(2-methoxybenzoyl)benzenesulfonamide), R$^{21}$=cyclopropyl and R$^{22}$=5-Cl (S3-2), R$^{21}$=ethyl and R$^{22}$=H (S3-3), R$^{21}$=isopropyl and R$^{22}$=5-Cl (S3-4) and R$^{21}$=isopropyl and R$^{22}$=H (S3-5);

f) compounds of the type of the N-acylsulfamoylphenylureas of the formula (VIII) which are known, for example, from EP-A-365484,

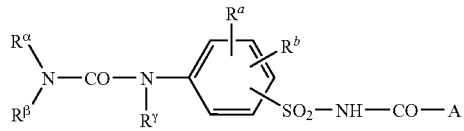

(VIII)

in which

A is a radical from the group consisting of

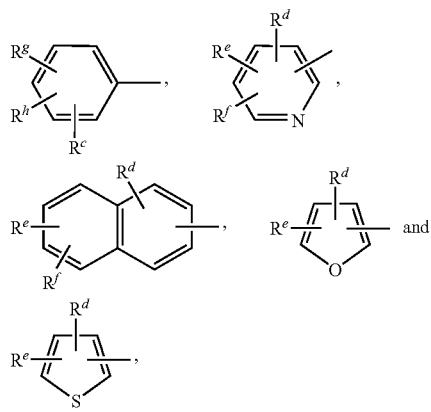

R$^\alpha$ and R$^\beta$ independently of one another are hydrogen, C$_1$-C$_8$-alkyl, C$_3$-C$_8$-cycloalkyl, C$_3$-C$_6$-alkenyl, C$_3$-C$_6$-alkynyl,

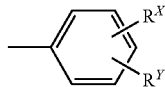

or C$_1$-C$_4$-alkoxy which is si

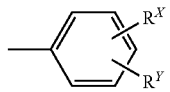

C$_1$-C$_4$-alkoxy, or

R$^\alpha$ and R$^\beta$ together are a C$_4$-C$_6$-alkylene bridge or a C$_4$-C$_6$-alkylene bridge which is interrupted by oxygen, sulfur, SO, SO$_2$, NH or —N(C$_1$-C$_4$-alkyl)-, R$^\gamma$ is hydrogen or C$_1$-C$_4$-alkyl, R$^a$ and R$^b$ independently of one another are hydrogen, halogen, cyano, nitro, trifluoromethyl, C$_1$-C$_4$-alkyl, C$_1$-C$_4$-alkoxy, C$_1$-C$_4$-alkylthio, C$_1$-C$_4$-alkylsulfinyl, C$_1$-C$_4$-alkylsulfonyl, —COOR$^j$, —CONR$^k$R$^m$, —COR$^n$, —SO$_2$NR$^k$R$^m$ or —OSO$_2$—C$_1$-C$_4$-alkyl, or R$^a$ and R$^b$ together are a C$_3$-C$_4$-alkylene bridge which may be substituted by halogen or C$_1$-C$_4$-alkyl, or a C$_3$-C$_4$-alkenylene bridge which may be substituted by halogen or C$_1$-C$_4$-alkyl, or a C$_4$-alkadienylene bridge which may be substituted by halogen or C$_1$-C$_4$-alkyl, and R$^g$ and R$^h$ independently of one another are hydrogen, halogen, C$_1$-C$_4$-alkyl, trifluoromethyl, methoxy, methylthio or —COOR$^j$, where R$^c$ is hydrogen, halogen, C$_1$-C$_4$-alkyl or methoxy, R$^d$ is hydrogen, halogen, nitro, C$_1$-C$_4$-alkyl, C$_1$-C$_4$-alkoxy, C$_1$-C$_4$-alkylthio, C$_1$-C$_4$-alkylsulfinyl, C$_1$-C$_4$-alkylsulfonyl, —COOR$^j$ or —CONR$^k$R$^m$, R$^e$ is hydrogen, halogen, C$_1$-C$_4$-alkyl, —COOR$^j$, trifluoromethyl or methoxy, or R$^d$ and R$^e$ together are a C$_3$-C$_4$-alkylene bridge, R$^f$ is hydrogen, halogen or C$_1$-C$_4$-alkyl, R$^X$ and R$^Y$ independently of one another are hydrogen, halogen, C$_1$-C$_4$-alkyl, C$_1$-C$_4$-alkoxy, C$_1$-C$_4$-alkylthio, —COOR$^4$, trifluoromethyl, nitro orcyano, R$^j$, R$^k$ and R$^m$ independently of one another are hydrogen or C$_1$-C$_4$-alkyl, R$^k$ and R$^m$ together are a C$_4$-C$_6$-alkylene bridge or a C$_4$-C$_6$-alkylene bridge which is interrupted by oxygen, NH or —N(C$_1$-C$_4$-alkyl)-, and R$^n$ is C$_1$-C$_4$-alkyl, phenyl or phenyl which is substituted by halogen, C$_1$-C$_4$-alkyl, methoxy, nitro or trifluoromethyl, preferably 1-[4-(N-2-methoxybenzoylsulfamoyl)phenyl]-3-methylurea, 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthoylsulfamoyl)phenyl]-3,3-dimethylurea, including the stereoisomers and the agriculturally customary salts.

Preference is given to herbicide-safener combinations comprising (A) a herbicidally effective amount of one or more compounds of the formula (I) or salts thereof and (B) an amount, acting as an antidote, of one or more safeners.

Herbicidally effective amount in the sense of the invention is an amount of one or more herbicides sufficient to have a negative impact on plant growth. In the sense of the invention, an amount which acts as an antidote is an amount of one or more safeners sufficient to reduce the phytotoxic action of crop protection agents (for example herbicides) in crop plants.

Unless specifically defined otherwise, the following definitions generally apply to the radicals in the formulae (I) to (VIII) and the formulae below.

The radicals alkyl, alkoxy, haloalkyl, haloalkoxy, alkylamino and alkylthio and the corresponding unsaturated and/or substituted radicals may in each case be straight-chain or branched in the carbon skeleton.

Alkyl radicals, including in composite meanings, such as alkoxy, haloalkyl, etc., preferably have 1 to 4 carbon atoms and are, for example, methyl, ethyl, n- or isopropyl, n-, iso-, t- or 2-butyl. Alkenyl and alkynyl radicals have the meaning of the possible unsaturated radicals which correspond to the alkyl radicals; alkenyl is, for example, allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl. Alkynyl is, for example, propargyl, but-2-yn-1-yl, but-3-yn-1-yl, 1-methyl-but-3-yn-1-yl. "$(C_1-C_4)$-Alkyl" is the short notation for alkyl having 1 to 4 carbon atoms; this applies correspondingly to other general radical definitions having ranges of the possible number of carbon atoms stated in brackets.

Cycloalkyl is preferably a cyclic alkyl radical having 3 to 8, preferably 3 to 7, particularly preferably 3 to 6, carbon atoms, for example cyclopropyl, cyclobutyl, cyclopentyl and cyclohexyl. Cycloalkenyl and cycloalkynyl refer to corresponding unsaturated compounds.

Halogen is fluorine, chlorine, bromine or iodine. Haloalkyl, haloalkenyl and haloalkynyl are alkyl, alkenyl and alkynyl, respectively, which is partially or fully substituted by halogen, preferably by fluorine, chlorine and/or bromine, in particular by fluorine or chlorine, for example $CF_3$, $CHF_2$, $CH_2F$, $CF_2CF_3$, $CH_2CHFCl$, $CCl_3$, $CHCl_2$, $CH_2CH_2Cl$. Haloalkoxy is, for example, $OCF_3$, $OCHF_2$, $OCH_2F$, $OCF_2CF_3$, $OCH_2CF_3$ and $OCH_2CH_2Cl$. This applies correspondingly to other halogen-substituted radicals.

A hydrocarbon radical may be an aromatic or an aliphatic hydrocarbon radical, an aliphatic hydrocarbon radical generally being a straight-chain or branched saturated or unsaturated hydrocarbon radical having preferably 1 to 18, particularly preferably 1 to 12, carbon atoms, for example alkyl, alkenyl or alkynyl.

An aliphatic hydrocarbon radical is preferably alkyl, alkenyl or alkynyl having up to 12 carbon atoms; this applies correspondingly to an aliphatic hydrocarbon radical in a hydrocarbon oxy radical.

Aryl is generally a mono-, bi- or polycyclic aromatic system having preferably 6-20 carbon atoms, with preference 6 to 14 carbon atoms, particularly preferably 6 to 10 carbon atoms, for example phenyl, naphthyl, tetrahydronaphthyl, indenyl, indanyl, pentalenyl and fluorenyl, particularly preferably phenyl.

Heterocyclic ring, heterocyclic radical or heterocyclyl refers to a mono-, bi- or polycyclic ring system which is saturated, unsaturated and/or aromatic and contains one or more, preferably 1 to 4, heteroatoms, preferably from the group consisting of nitrogen, sulfur and oxygen.

Preference is given to saturated heterocycles having 3 to 7 ring atoms and one or two heteroatoms from the group of nitrogen, oxygen and sulfur, where the chalcogens are not adjacent. Particular preference is given to monocyclic rings having 3 to 7 ring atoms and one heteroatom from the group consisting of nitrogen, oxygen and sulfur and also morpholine, dioxolane, piperazine, imidazoline and oxazolidine. Very particularly preferred saturated heterocycles are oxirane, pyrrolidone, morpholine and tetrahydrofuran.

Preference is also given to partially unsaturated heterocycles having 5 to 7 ring atoms and one or two heteroatoms from the group consisting of nitrogen, oxygen and sulfur. Particular preference is given to partially unsaturated heterocycles having 5 to 6 ring atoms and one heteroatom from the group consisting of nitrogen, oxygen and sulfur. Very particularly preferred partially unsaturated heterocycles are pyrazoline, imidazoline and isoxazoline.

Preference is likewise given to heteroaryl, for example mono- or bicyclic aromatic heterocycles having 5 to 6 ring atoms which contain one to four heteroatoms from the group consisting of nitrogen, oxygen and sulfur, where the chalcogens are not adjacent. Particular preference is given to monocyclic aromatic heterocycles having 5 to 6 ring atoms which contain a heteroatom from the group consisting of nitrogen, oxygen and sulfur, and also pyrimidine, pyrazine, pyridazine, oxazole, thiazole, thiadiazole, oxadiazole, pyrazole, triazole and isoxazole. Very particular preference is given to pyrazole, thiazole, triazole and furan.

Substituted radicals, such as substituted hydrocarbon radicals, for example substituted alkyl, alkenyl, alkynyl, aryl such as phenyl, and arylalkyl, such as benzyl, or substituted heterocyclyl, are substituted radicals which are derived from the unsubstituted skeleton, where the substituents preferably have one or more, preferably 1, 2 or 3, in the case of Cl and F also up to the maximum number possible, substituents from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and also the unsaturated aliphatic substituents which correspond to the saturated hydrocarbon-containing substituents mentioned, preferably alkenyl, alkynyl, alkenyloxy, alkynyloxy. In the case of radicals having carbon atoms, preference is given to those having 1 to 4 carbon atoms, in particular 1 or 2 carbon atoms. Preference is generally given to substituents from the group consisting of halogen, for example fluorine or chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy and chlorine.

Mono- or disubstituted amino is a chemically stable radical from the group of the substituted amino radicals which are N-substituted, for example, by one or two identical or different radicals from the group consisting of alkyl, alkoxy, acyl and aryl; preferably monoalkylamino, dialkylamino, acylamino, arylamino, N-alkyl-N-arylamino, and also N-heterocycles. Preference is given here to alkyl radicals having 1 to 4 carbon atoms. Aryl is preferably phenyl in this case. Substituted aryl is preferably substituted phenyl. Acyl is as defined further below, preferably $(C_1-C_4)$-alkanoyl. This applies correspondingly to substituted hydroxylamino or hydrazino.

Optionally substituted phenyl is preferably phenyl which is unsubstituted or mono- or polysubstituted, preferably up to trisubstituted, in the case of halogens such as Cl and F also up to pentasubstituted, by identical or different radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichloro-phenyl, o-, m- and p-methoxyphenyl.

An acyl radical is the radical of an organic acid having preferably up to 6 carbon atoms, for example the radical of a carboxylic acid and radicals of acids derived therefrom, such as thiocarboxylic acid, if appropriate N-substituted aminocarboxylic acids, or the radical of carbonic monoesters, optionally N-substituted carbaminic acids, sulfonic acids, sulfinic acids, phosphonic acids, phosphinic acids. Acyl is, for example, formyl, alkylcarbonyl, such as $(C_1-C_4$-alkyl)-carbonyl, phenylcarbonyl, where the phenyl ring may be substituted, for example as stated above for phenyl, or alkyloxycarbonyl, phenyloxycarbonyl, benzyloxycarbonyl, alkylsulfonyl, alkylsulfinyl or N-alkyl-1-iminoalkyl.

The formulae (I) to (VIII) also include all stereoisomers having the same topological attachment of atoms, and mixtures thereof. Such compounds contain one or more asymmetric carbon atoms or else double bonds which are not specifically shown in the general formulae. The possible stereoisomers, defined by their specific spatial form, such as enantiomers, diastereomers, Z- and E-isomers, can be obtained from mixtures of the stereoisomers by customary methods or else by stereoselective reactions in combination with the use of stereochemically pure starting materials.

The compounds of the formula (II) are known, for example, from EP-A-0 333 131 (ZA-89/1960), EP-A-0 269 806 (U.S. Pat. No. 4,891,057), EP-A-0 346 620 (AU-A-89/34951), EP-A-0 174 562, EP-A-0 346 620 (WO-A-91/08 202), WO-A-91/07 874 or WO-A 95/07 897 (ZA 94/7120) and the literature cited therein or can be prepared by or analogously to the processes described therein. The compounds of the formula (III) are known from EP-A-0 086 750, EP-A-0 94349 (U.S. Pat. No. 4,902,340), EP-A-0 191736 (U.S. Pat. No. 4,881,966) and EP-A-0 492 366 and the literature cited therein or can be prepared by or analogously to the processes described therein. Furthermore, some compounds are described in EP-A-0 582 198 and WO 2002/34048.

The compounds of the formula (IV) are known from numerous patent applications, for example U.S. Pat. No. 4,021,224 and U.S. Pat. No. 4,021,229.

Compounds of the group B (b) are furthermore known from CN-A-87/102 789, EP-A-365484 and from "The Pesticide Manual", The British Crop Protection Council and the Royal Society of Chemistry, 11th edition, Farnham 1997.

The compounds of the group B (c) are described in WO-A-97/45016, those of group B (d) in WO-A-99/16744 and those of group B (e) in EP-A-365484.

The publications cited contain detailed statements about preparation processes and starting materials and mention preferred compounds. These publications are expressly referred to; by reference, they form part of the present description.

Preference is given to herbicide-safener combinations comprising safeners of the formula (II) and/or (III) in which the symbols and indices are as defined below:

$R^{24}$ is hydrogen, $(C_1-C_{18})$-alkyl, $(C_3-C_{12})$-cycloalkyl, $(C_2-C_8)$-alkenyl and $(C_2-C_{18})$-alkynyl, where the carbon-containing groups may be substituted by one or more, preferably up to three, radicals $R^{50}$;

$R^{50}$ is are identical or different and are halogen, hydroxyl, $(C_1-C_8)$-alkoxy, $(C_1-C_8)$-alkylthio, $(C_2-C_8)$-alkenylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$-cycloalkoxy, cyano, mono- and di$(C_1-C_4)$-alkylamino, carboxyl, $(C_1-C_8)$-alkoxycarbonyl, $(C_2-C_8)$-alkenyloxycarbonyl, $(C_1-C_8)$-alkyl-thiocarbonyl, $(C_2-C_8)$-alkynyloxycarbonyl, $(C_1-C_8)$-alkylcarbonyl, $(C_2-C_8)$-alkenylcarbonyl, $(C_2-C_8)$-alkynylcarbonyl, 1-(hydroxyimino)-$(C_1-C_6)$-alkyl, 1-[$(C_1-C_4)$-alkylimino]-$(C_1-C_4)$-alkyl, 1-[$(C_1-C_4)$-alkoxyimino]-$(C_1-C_6)$-alkyl, $(C_1-C_8)$-alkylcarbonylamino, $(C_2-C_8)$-alkenylcarbonylamino, $(C_2-C_8)$-alkynylcarbonylamino, amino-carbonyl, $(C_1-C_8)$-alkylaminocarbonyl, di-$(C_1-C_6)$-alkylamino-carbonyl, $(C_2-C_6)$-alkenylaminocarbonyl, $(C_2-C_6)$-alkynylaminocarbonyl, $(C_1-C_8)$-alkoxycarbonylamino, $(C_1-C_8)$-alkylamino-carbonylamino, $(C_1-C_6)$-alkylcarbonyloxy which is unsubstituted or substituted by $R^{51}$ $(C_2-C_6)$-alkenylcarbonyloxy, $(C_2-C_6)$-alkynyl-carbonyloxy, $(C_1-C_8)$-alkylsulfonyl, phenyl, phenyl-$(C_1-C_6)$-alkoxy, phenyl-$(C_1-C_6)$-alkoxycarbonyl, phenoxy, phenoxy-$(C_1-C_6)$-alkoxy, phenoxy-$(C_1-C_6)$-alkoxycarbonyl, phenylcarbonyloxy, phenyl-carbonylamino, phenyl-$(C_1-C_6)$-alkylcarbonylamino, where the phenyl ring of the 9 last-mentioned radicals is unsubstituted or mono- or polysubstituted, preferably up to trisubstituted, by radicals $R^{52}$ ; $SiR'_3$, —O—$SiR'_3$, $R'_3Si$—$(C_1-C_8)$-alkoxy, —CO—O—$NR'_2$, —O—N=$CR'_2$, —N=$CR'_2$, —O—$NR'_2$, —$NR'_2$, $CH(OR')_2$, —O—$(CH_2)_m$—$CH(OR')_2$, —$CR'''(OR')_2$, —O—$(CH_2)_mCR'''(OR'')_2$ or by $R''O$—$CHR'''CHCOR''$—$(C_1-C_6)$-alkoxy, $R^{51}$ are identical or different and are halogen, nitro, $(C_1-C_4)$-alkoxy and phenyl which is unsubstituted or substituted by one or more, preferably up to three, radicals $R^{52}$;

$R^{52}$ are identical or different and are halogen, $(C_1-C_4)$-alkyl, $(C_1-C_4)$-alkoxy, $(C_1-C_4)$-haloalkyl, $(C_1-C_4)$-haloalkoxy or nitro;

R' are identical or different and are hydrogen, $(C_1-C_4)$-alkyl, phenyl which is unsubstituted or substituted by one or more, preferably up to three, radicals $R^{52}$, or two radicals R' together form a $(C_2-C_6)$-alkanediyl chain;

R" are identical or different and are $(C_1-C_4)$-alkyl, or two radicals R" together form a $(C_2-C_6)$-alkanediyl chain;

R''' is hydrogen or $(C_1-C_4)$-alkyl;

m is 0, 1, 2, 3, 4, 5 or 6.

Particular preference is given to herbicide-safener combinations according to the invention comprising safeners of the formula (II) and/or (III) in which the symbols and indices are as defined below:

$R^{24}$ is hydrogen, $(C_1-C_8)$-alkyl or $(C_3-C_7)$-cycloalkyl, where the carbon-containing radicals above are unsubstituted or mono- or polysubstituted by halogen or mono- or disubstituted, preferably monosubstituted, by radicals $R^{50}$, $R^{50}$ are identical or different and are hydroxyl, $(C_1-C_4)$-alkoxy, carboxyl, $(C_1-C_4)$-alkoxycarbonyl, $(C_2-C_6)$-alkenyloxycarbonyl, $(C_2-C_6)$-alkynyloxycarbonyl, 1-(hydroxyimino)-$(C_1-C_4)$-alkyl, 1-[$(C_1-C_4)$-alkylimino]-$(C_1-C_4)$-alkyl and 1-[$(C_1-C_4)$-alkoxyimino]-$(C_1-C_4)$-alkyl; —$SiR'_3$, —O—N=$CR'_2$, —N=$CR'_2$, —$NR'_2$ and —O—$NR'_2$, in which R' are identical or different and are hydrogen, $(C_1-C_4)$-alkyl or, as a pair, are a $(C_4-C_5)$-alkanediyl chain, $R^{27}$, $R^{28}$, $R^{29}$ are identical or different and are hydrogen, $(C_1-C_8)$-alkyl, $(C_1-C_6)$-haloalkyl, $(C_3-C_7)$-cycloalkyl or phenyl which is unsubstituted or substituted by one or more radicals from the group consisting of halogen, cyano, nitro, amino, mono- and di-[$(C_1-C_4)$-alkyl]amino, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and $(C_1-C_4)$-alkylsulfonyl;

$R^X$ is hydrogen or $COOR^{24}$, where $R^{26}$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxy-alkyl, $(C_3-C_7)$-cycloalkyl or tri-$(C_1-C_4)$-alkylsilyl, $R^{17}$, $R^{19}$ are identical or different and are halogen, methyl, ethyl, methoxy, ethoxy, $(C_1-C_2)$-haloalkyl, preferably hydrogen, halogen or $(C_1-C_2)$-haloalkyl.

Very particular preference is given to safeners in which the symbols and indices in the formula (II) are as defined below:
$R^{17}$ is halogen, nitro or $(C_1-C_4)$-haloalkyl;
n' is 0, 1, 2 or 3;
$R^{81}$ is a radical of the formula OR
$R^{24}$ is hydrogen, $(C_1-C_8)$-alkyl or $(C_3-C_7)$-cycloalkyl, where the carbon-containing radicals above are unsubstituted or mono- or poly-substituted, preferably up to trisubstituted, by identical or different halogen radicals or up to disubstituted, preferably monosubstituted, by identical or different radicals from the group consisting of hydroxyl, $(C_1-C_4)$-alkoxy, $(C_1-C_4)$-alkoxycarbonyl, $(C_2-C_6)$-alkenyl-oxycarbonyl, $(C_2-C_6)$-a lkynyloxycarbonyl, 1-(hydroxyimino)-$(C_1-C_4)$-alkyl, 1-[$(C_1-C_4)$-alkylimino]-$(C_1-C_4)$-alkyl, 1-[$(C_1-C_4)$-alkoxyimino]-$(C_1-C_4)$-alkyl and radicals of the formulae —SiR'$_3$, —O—N=R'$_2$, —N=CR'$_2$, —NR'$_2$ and —O—NR'$_2$, where the radicals R' in the formulae mentioned are identical or different and are hydrogen, $(C_1-C_4)$-alkyl or, as a pair, are $(C_4-C_5)$-alkanediyl;
$R^{27}$, $R^{28}$, $R^{29}$ are identical or different and are hydrogen, $(C_1-C_8)$-alkyl, $(C_1-C_6)$-haloalkyl, $(C_3-C_7)$-cycloalkyl or phenyl which is unsubstituted or substituted by one or more radicals from the group consisting of halogen, $(C_1-C_4)$-alkyl, $(C_1-C_4)$-alkoxy, nitro, $(C_1-C_4)$-haloalkyl and $(C_1-C_4)$-haloalkoxy, and
$R^X$ is hydrogen or COOR$^{26}$, where $R^{26}$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxy-alkyl, $(C_3-C_7)$-cycloalkyl or tri-$(C_1-C_4)$-alkylsilyl.

Very particular preference is also given to safeners of the formula (III) in which the symbols and indices are as defined below:
$R^{19}$ is halogen or $(C_1-C_4)$-haloalkyl;
n' is 0, 1, 2 or 3, where $(R^{19})n'$ is preferably 5-Cl;
$R^{20}$ is a radical of the formula OR$^{24}$;
T is CH$_2$ or CH(COO—$(C_1-C_3)$-alkyl) and
$R^{24}$ is hydrogen, $(C_1-C_8)$-alkyl, $(C_1-C_8)$-haloalkyl or $(C_1-C_4)$-alkoxy-$(C_1-C_4)$-alkyl, preferably hydrogen or $(C_1-C_8)$-alkyl.

Especially preferred are safeners of the formula (II) in which the symbols and indices are as defined below:
W is (W1);
$R^{17}$ is halogen or $(C_1-C_2)$-haloalkyl;
n' is 0, 1, 2 or 3, where $(R^{17})_{n'}$ is preferably 2,4-Cl$_2$;
$R^{18}$ is a radical of the formula OR$^{24}$;
$R^{24}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4)$-alkoxy-$(C_1-C_4)$-alkyl or tri-$(C_1-C_2)$-alkylsilyl, preferably $(C_1-C_4)$-alkyl;
$R^{27}$ is hydrogen, $(C_1-C_8)$-alkyl, $(C_1-C_4)$-haloalkyl or $(C_3-C_7)$-cycloalkyl, preferably hydrogen or $(C_1-C_4)$-alkyl, and
$R^X$ is COOR$^{26}$, where $R^{26}$ is hydrogen, $(C_1-C_8)$-alkyl, $(C_1-C_4)$-halo-alkyl, $(C_1-C_4)$-hydroxyalkyl, $(C_3-C_7)$-cycloalkyl, $(C_1-C_4)$-alkoxy-$(C_1-C_4)$-alkyl or tri-$(C_1-C_2)$-alkylsilyl, preferably hydrogen or $(C_1-C_4)$-alkyl.

Also especially preferred are herbicidal compositions comprising a safener of the formula (II) in which the symbols and indices are as defined below:
W is (W2);
$R^{17}$ is halogen or $(C_1-C_2)$-haloalkyl;
n' is 0, 1, 2 or 3, where $(R^{17})_{n'}$ is preferably 2,4-Cl$_2$;
$R^{18}$ is a radical of the formula OR$^{24}$;
$R^{24}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4)$-alkoxy-$(C_1-C_4)$-alkyl or tri-$(C_1-C_2)$-alkyl-silyl, preferably $(C_1-C_4)$-alkyl, and
$R^{27}$ is hydrogen, $(C_1-C_8)$-alkyl, $(C_1-C_4)$-haloalkyl, $(C_3-C_7)$-cycloalkyl or unsubstituted or substituted phenyl, preferably hydrogen, $(C_1-C_4)$-alkyl or phenyl which is unsubstituted or substituted by one or more radicals from the group consisting of halogen, $(C_1-C_4)$-alkyl, $(C_1-C_4)$-haloalkyl, nitro, cyano and $(C_1-C_4)$-alkoxy.

Especially preferred are also safeners of the formula (II) in which the symbols and indices are as defined below:
W is (W3);
$R^{17}$ is halogen or $(C_1-C_2)$-haloalkyl;
n' is 0, 1, 2 or 3, where $(R^{17})_{n'}$ is preferably 2,4-Cl$_2$;
$R^{18}$ is a radical of the formula OR$^{24}$;
$R^{24}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4)$-alkoxy-$(C_1-C_4)$-alkyl or tri-$(C_1-C_2)$-alkyl-silyl, preferably $(C_1-C_4)$-alkyl, and
$R^{28}$ is $(C_1-C_8)$-alkyl or $(C_1-C_4)$-haloalkyl, preferably C$_1$-haloalkyl.

Especially preferred are also safeners of the formula (II) in which the symbols and indices are as defined below:
W is (W4);
$R^{17}$ is halogen, nitro, $(C_1-C_4)$-alkyl, $(C_1-C_2)$-haloalkyl, preferably CF$_3$, or $(C_1-C_4)$-alkoxy;
n' is 0, 1, 2 or 3;
m' is 0 or 1;
$R^{18}$ is a radical of the formula OR$^{24}$;
$R^{24}$ is hydrogen, $(C_1-C_4)$-alkyl, carboxy-$(C_1-C_4)$-alkyl, $(C_1-C_4)$-alkoxy-carbonyl-$(C_1-C_4)$-alkyl, preferably $(C_1-C_4)$-alkoxy-CO—CH$_2$—, $(C_1-C_4)$-alkoxy-CO—C(CH$_3$)H—, HO—CO—CH$_2$— or HO—CO—C(CH$_3$)H—, and
$R^{29}$ is hydrogen, $(C_1-C_4)$-alkyl, $(C_1-C_4)$-haloalkyl, $(C_3-C_7)$-cycloalkyl or phenyl which is unsubstituted or substituted by one or more radicals from the group consisting of halogen, $(C_1-C_4)$-alkyl, $(C_1-C_4)$-halo-alkyl, nitro, cyano and $(C_1-C_4)$-alkoxy.

Particularly suitable safeners for the herbicidally active compounds of the formula (I) are the following groups of compounds:
a) compounds of the type of the dichlorophenylpyrazoline-3-carboxylic acid (i.e. of the formula (II) in which W=(W1) and $(R^{17})_{n'}$=2,4-Cl$_2$), preferably compounds such as ethyl1-(2,4-dichlorophenyl)-5-(ethoxycarbonyl)-5-methyl-2-pyrazoline-3-carboxylate (II-1, mefenpyr-diethyl), mefenpyr-dimethyl and mefenpyr (II-0), and related compounds as described in WO-A 91/07874;
b) derivatives of dichlorophenylpyrazolecarboxylic acid (i.e. of the formula (II) in which W=(W2) and $(R^{17})_{n'}$=2,4-Cl$_2$), preferably compounds such as ethyl1-(2,4-dichlorophenyl)-5-methylpyrazole-3-carboxylate (II-2), ethyl1-(2,4-dichlorophenyl)-5-isopropylpyrazole-3-carboxylate (II-3), ethyl1-(2,4-dichlorophenyl)-5-(1,1-dimethyl-ethyl)pyrazole-3-carboxylate (II-4), ethyl1-(2,4-dichlorophenyl)-5-phenylpyrazole-3-carboxylate (II-5) and related compounds, as described in EP-A-0 333 131 and EP-A-0 269 806;
c) compounds of the type of the triazolecarboxylic acids (i.e. of the formula (II) in which W=(W3) and $(R^{17})_{n'}$=2,4-Cl$_2$), preferably compounds such as fenchlorazole-ethyl, i.e. ethyl1-(2,4-dichloro-phenyl)-5-trichloromethyl-(1H)-1,2,4-triazole-3-carboxylate (II-6), and related compounds (see EP-A-0 174 562 and EP-A-0 346 620);
d) compounds of the type of the 5-benzyl- or 5-phenyl-2-isoxazoline-3-carboxylic acid or of the 5,5-diphenyl-2- isoxazoline-3-carboxylic acid, such as isoxadifen (II-12), (in which W=(W4)), preferably compounds such as ethyl5-(2,4-dichlorobenzyl)-2-isoxazoline-3-carboxylate (II-7) or ethyl5-phenyl-2-isoxazoline-3-carboxylate (II-8) and related compounds, as described in WO-A-91/08202, or of ethyl5,5-diphenyl-2-isoxazolinecarboxylate (II-9, isoxadifen-ethyl) or n-propyl5,5-diphenyl-2-isoxazolinecarboxylate (II-10) or of ethyl5-(4-fluorophenyl)-5-phenyl-2-isoxazoline-3-carboxylate (II-11), as described in WO-A-95/07897.

e) Compounds of the type of the 8-quinolineoxyacetic acid, for example those of the formula (III) in which $(R^{19})_n$=5-Cl, $R^{20}$=$OR^{24}$ and T=$CH_2$, preferably the compounds 1-methylhexyl(5-chloro-8-quinolineoxy)acetate (III-1, cloquintocet-mexyl), 1,3-dimethylbut-1-yl(5-chloro-8-quinolineoxy)acetate (III-2), 4-allyloxybutyl(5-chloro-8-quinolineoxy)acetate (III-3), 1-allyloxyprop-2-yl(5-chloro-8-quinolineoxy)acetate (III-4), ethyl(5-chloro-8-quinolineoxy)acetate (III-5), methyl(5-chloro-8-quinolineoxy)acetate (III-6), allyl(5-chloro-8-quinolineoxy)acetate (III-7), 2-(2-propylideneiminoxy)-1-ethyl(5-chloro-8-quinolineoxy)acetate (III-8), 2-oxoprop-1-yl(5-chloro-8-quinolineoxy)acetate (III-9), (5-chloro-8-quinolineoxy)acetic acid (III-10) and its salts, as described, for example, in WO-A-2002/34048, and related compounds as described in EP-A-0 860 750, EP-A-0 094 349 and EP-A-0 191 736 or EP-A-0 492 366.

f) Compounds of the type of the (5-chloro-8-quinolineoxy)malonic acid, i.e. of the formula (III) in which $(R^{19})_n$=5-Cl, $R^{20}$=$OR^{24}$, T=—CH(COO-alkyl)-, preferably the compounds diethyl(5-chloro-8-quinolineoxy)malonate (III-11), diallyl(5-chloro-8-quinolineoxy)-malonate, methyl ethyl(5-chloro-8-quinolineoxy)malonate and related compounds, as described in EP-A-0 582 198.

g) Compounds of the type of the dichloroacetamide, i.e. of the formula (IV), preferably: N,N-diallyl-2,2-dichloroacetamide (dichlormid (IV-1), from U.S. Pat. No. 4,137,070), 4-dichloroacetyl-3,4-dihydro-3-methyl-2H-1,4-benzoxazine (IV-2, benoxacor, from EP 0 149 974), N1,N2-diallyl-N2-dichloroacetylglycinamide (DKA-24 (IV-3), from HU 2143821), 4-dichloroacetyl-1-oxa-4-azaspiro[4,5]decane (AD-67), 2,2-dichloro-N-(1,3-dioxolan-2-ylmethyl)-N-(2-propenyl)acetamide (PPG-1292), 3-dichloroacetyl-2,2,5-trimethyloxazolidine (R-29148, IV4), 3-dichloroacetyl-2,2-dimethyl-5-phenyloxazolidine, 3-dichloroacetyl-2,2-dimethyl-5-(2-thienyl)oxazolidine, 3-dichloroacetyl-5-(2-furanyl)-2,2-dimethyloxazolidine (furilazole (IV-5), MON 13900), 1-dichloroacetylhexahydro-3,3,8a-trimethylpyrrolo[1,2-a]pyrimidin-6(2H)-one (dicyclonon, BAS 145138).

h) Compounds of the group B(b), preferably 1,8-naphthalic anhydride (b-1), methyl diphenylmethoxyacetate (b-2), cyanomethoxyimino(phenyl)acetonitrile (cyometrinil) (b-3), 1-(2-chlorobenzyl)-3-(1-methyl-1-phenylethyl)urea (cumyluron) (b-4), O,O-diethyl S-2-ethylthioethyl phosphorodithioate (disulfoton) (b-5), 4-chlorophenyl methylcarbamate (mephenate) (b-6), O,O-diethyl-O-phenyl phosphorothioate (diethalate) (b-7), 4-carboxy-3,4-dihydro-2H-1-benzopyran-4-acetic acid (CL-304415 CAS-Regno: 31541-57-8) (b-8), 1,3-dioxolan-2-ylmethoxyimino(phenyl)acetonitrile (oxabetrinil) (b-9), 4'-chloro-2,2,2-trifluoroacetophenone O-1,3-dioxolan-2-ylmethyl-oxime (fluxofenim) (b-10), 4,6-dichloro-2-phenylpyrimidine (fenclorim) (b-11), benzyl 2-chloro-4-trifluoromethyl-1,3-thiazole-5-carboxylate (flurazole) (b-12), 2-dichloromethyl-2-methyl-1,3-dioxolane (MG-191) (b-13), N-(4-methylphenyl)-N'-(1-methyl-1-phenylethyl)urea (dymron) (b-14), (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl3,6-dichloro-2-methoxybenzoate (lactidichlor)

and their salts and esters, preferably their ($C_1$-$C_8$)-esters.

Preferred safeners are furthermore compounds of the formula (V) or salts thereof in which $R^{30}$ is hydrogen, ($C_1$-$C_6$)-alkyl, ($C_3$-$C_6$)-cycloalkyl, furanyl or thienyl, where each of the 4 last-mentioned radicals is unsubstituted or substituted by one or more substituents from the group consisting of halogen, ($C_1$-$C_4$)-alkoxy, halo-($C_1$-$C_6$)-alkoxy and ($C_1$-$C_4$)-alkylthio and, in the case of cyclic radicals, also ($C_1$-$C_4$)-alkyl and ($C_1$-$C_4$)-haloalkyl, $R^{31}$ is hydrogen, $R^{32}$ is halogen, halo-($C_1$-$C_4$)-alkyl, halo-($C_1$-$C_4$)-alkoxy, ($C_1$-$C_4$)-alkyl, ($C_1$-$C_4$)-alkoxy, ($C_1$-$C_4$)-alkylsulfonyl, ($C_1$-$C_4$)-alkoxycarbonyl or ($C_1$-$C_4$)-alkylcarbonyl, preferably halogen, ($C_1$-$C_4$)-haloalkyl, such as trifluoromethyl, ($C_1$-$C_4$)-alkoxy, halo-($C_1$-$C_4$)-alkoxy, ($C_1$-$C_4$)-alkoxycarbonyl or ($C_1$-$C_4$)-alkylsulfonyl, $R^{33}$ is hydrogen, $R^{34}$ is halogen, ($C_1$-$C_4$)-alkyl, halo-($C_1$-$C_4$)-alkyl, halo-($C_1$-$C_4$)-alkoxy, ($C_3$-$C_6$)-cycloalkyl, phenyl, ($C_1$-$C_4$)-alkoxy, cyano, ($C_1$-$C_4$)-alkylthio, ($C_1$-$C_4$)-alkylsulfinyl, ($C_1$-$C_4$)-alkylsulfonyl, ($C_1$-$C_4$)-alkoxycarbonyl or ($C_1$-$C_4$)-alkylcarbonyl, preferably halogen, ($C_1$-$C_4$)-alkyl, ($C_1$-$C_4$)-haloalkyl, such as trifluoromethyl, halo-($C_1$-$C_4$)-alkoxy, ($C_1$-$C_4$)-alkoxy or ($C_1$-$C_4$)-alkylthio, n is 0, 1 or 2 and m is 1 or 2.

Particular preference is given to compounds of the formula (V) in which $R^{30}$=$H_3C$—O—$CH_2$—, $R^{31}$=$R^{33}$=H, $R^{34}$=2-OMe (V-1), $R^{30}$=$H_3C$—O—$CH_2$—, $R^{31}$=$R^{33}$=H, $R^{34}$=2-OMe-5-Cl (V-2), $R^{30}$=cyclopropyl, $R^{31}$=$R^{33}$=H, $R^{34}$=2-OMe (V-3), $R^{30}$=cyclopropyl, $R^{31}$=$R^{33}$=H, $R^{34}$=2-OMe-5-Cl (V-4), $R^{30}$=cyclopropyl, $R^{31}$=$R^{33}$=H, $R^{34}$=2-Me (M-5), $R^{30}$=tert-butyl, $R^{31}$=$R^{33}$=H, $R^{34}$=2-OMe (V-6).

Preference is furthermore given to safeners of the formula (VI) in which
X³ is CH;
R³⁵ is hydrogen, $(C_1-C_6)$-alkyl, $(C_3-C_6)$-cycloalkyl, $(C_2-C_6)$-alkenyl, $(C_5-C_6)$-cycloalkenyl, phenyl or 3- to 6-membered heterocyclyl having up to 3 heteroatoms from the group consisting of nitrogen, oxygen and sulfur, where the six last-mentioned radicals are optionally substituted by one or more identical or different substituents from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;
R³⁶ is hydrogen, $(C_1-C_6)$-alkyl, $(C_2-C_6)$-alkenyl, $(C_2-C_6)$-alkynyl, where the three last-mentioned radicals are optionally substituted by one or more identical or different substituents from the group consisting of halogen, hydroxyl, $(C_1-C_4)$-alkyl, $(C_1-C_4)$-alkoxy and $(C_1-C_4)$-alkylthio;
R³⁷ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxy-carbonyl or $(C_1-C_4)$-alkylcarbonyl;
R³⁸ is hydrogen;
R³⁹ is halogen, nitro, $(C_1-C_4)$-alkyl, $(C_1-C_4)$-haloalkyl, $(C_1-C_4)$-halo-alkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;
n is 0, 1 or 2 and
m is 1 or 2.

Preferred safeners of the formula (VII) are (S3-1), (S3-2), (S3-3), (S3-4) and (S3-5).

Preferred safeners of the formula (VIII) are
1-[4-(N-2-methoxybenzoylsulfamoyl)phenyl]-3-methylurea (h-1),
1-[4-(N-2-methoxybenzoylsulfamoyl)phenyl]-3,3-dimethylurea (h-2),
1-[4-(N-4,5-dimethylbenzoylsulfamoyl)phenyl]-3-methylurea (h-3) and
1-[4-(N-naphthoylsulfamoyl)phenyl]-3,3-dimethylurea.

Particularly preferred safeners are dymron (b-14), fenclorim (b-11), cumyluron (b4), isoxadifen-ethyl (II-9), mefenpyr-diethyl (II-1), cloquintocet-mexyl (III-1), S3-1, h-1, h-2, h-3, dietholate (b-7), disulfoton (b-5), 1,8-naphthalic anhydride (b-1), fluxofenim (b-10), dichlormid (IV-1), benoxacor (IV-2), flurazole (b-12), R-29148 (IV-4). Particularly preferred for use in rice are dymron, fenclorim, cumyluron, isoxadifen-ethyl. Particularly preferred for use in cereals are mefenpyr-diethyl, cloquintocet-mexyl, in corn in particular isoxadifen-ethyl, (S3-1), (h-1), (h-2), (h-3), 1,8-naphthalic anhydride, fluxofenim, dichlormid, benoxacor, flurazole and R-29148. Preferred for use in sugar cane is isoxadifen-ethyl.

Examples of preferred combinations of herbicidally active compounds (A) and safeners (B) are: (I-1)+(II-0), (I-1)+(II-1), (I-1)+(II-3), (I-1)+(II-4), (I-1)+(II-5), (I-1)+(II-6), (I-1)+(II-9), (I-1)+(II-12), (I-1)+(III-1), (I-1)+(III-4), (I-1)+(III-10), (I-1)+(III-11), (I-1)+(IV-1), (I-1)+(IV-2), (I-1)+(IV-3), (I-1)+(IV-4), (I-1)+(IV-5), (I-1)+(b-1), (I-1)+(b-2), (I-1)+(b-3), (I-1)+(b-4), (I-1)+(b-5), (I-1)+(b-6), (I-1)+(b-7), (I-1)+(b-8), (I-1)+(b-9), (I-1)+(b-10), (I-1)+(b-11), (I-1)+(b-12), (I-1)+(b-13), (I-1)+(b-14), (I-1)+(S3-1), (I-1)+(S3-2), (I-1)+(S3-3), (I-1)+(S3-4), (I-1)+(S3-5), (I-1)+(h-1), (I-1)+(h-2), (I-1)+(V-1), (I-1)+(V-2), (I-1)+(V-3), (I-1)+(V-4), (I-1)+(V-5), (I-1)+(V-6).

(I-2)+(II-0), (I-2)+(II-1), (I-2)+(II-2), (I-2)+(II-3), (I-2)+(II-4), (I-2)+(II-5), (I-2)+(II-6), (I-2)+(II-9), (I-2)+(II-12), (I-2)+(III-1), (I-2)+(III-4), (I-2)+(III-10), (I-2)+(III-11), (I-2)+(IV-1), (I-2)+(IV-2), (I-2)+(IV-3), (I-2)+(IV-4), (I-2)+(IV-5), (I-2)+(b-1), (I-2)+(b-2), (I-2)+(b-3), (I-2)+(b-4), (I-2)+(b-5), (I-2)+(b-6), (I-2)+(b-7), (I-2)+(b-8), (I-2)+(b-9), (I-2)+(b-10), (I-2)+(b-11), (I-2)+(b-12), (I-2)+(b-13), (I-2)+(b-14), (I-2)+(S3-1), (I-2)+(S3-2), (I-2)+(S3-3), (I-2)+(S3-4), (I-2)+(S3-5), (I-2)+(h-1), (I-2)+(h-2), (I-2)+(V-1), (I-2)+(V-2), (I-2)+(V-3), (I-2)+(V-4), (I-2)+(V-5), (I-2)+(V-6).

(I-3)+(II-0), (I-3)+(II-1), (I-3)+(II-2), (I-3)+(II-3)+(II-4), (I-3)+(II-5), (I-3)+(II-6), (I-3)+(II-9), (I-3)+(II-12), (I-3)+(III-1), (I-3)+(III-4), (I-3)+(III-10), (I-3)+(III-11), (I-3)+(IV-1), (I-3)+(IV-2), (I-3)+(IV-3), (I-3)+(IV-4), (I-3)+(IV-5), (I-3)+(b-1), (I-3)+(b-2), (I-3)+(b-3), (I-3)+(b-4), (I-3)+(b-5), (I-3)+(b-6), (I-3)+(b-7), (I-3)+(b-8), (I-3)+(b-9), (I-3)+(b-10), (I-3)+(b-11), (I-3)+(b-12), (I-3)+(b-13), (I-3)+(b-14), (I-3)+(S3-1), (I-3)+(S3-2), (I-3)+(S3-3), (I-3)+(S3-4), (I-3)+(S3-5), (I-3)+(h-1), (I-3)+(h-2), (I-3)+(V-1), (I-3)+(V-2), (I-3)+(V-3), (I-3)+(V-4), (I-3)+(V-5), (I-3)+(V-6).

(I-4)+(II-0), (I-4)+(II-1), (I-4)+(II-2), (I-4)+(II-3), (I-4)+(II-4), (I-4)+(II-5), (I-4)+(II-6), (I-4)+(II-9), (I-4)+(II-12), (I-4)+(III-1), (I-4)+(III-4), (I-4)+(III-10), (I-4)+(III-11), (I-4)+(IV-1), (I-4)+(IV-2), (I-4)+(IV-3), (I-4)+(IV-4), (I-4)+(IV-5), (I-4)+(b-1), (I-4)+(b-2), (I-4)+(b-3), (I-4)+(b-4), (I-4)+(b-5), (I-4)+(b-6), (I-4)+(b-7), (I-4)+(b-8), (I-4)+(b-9), (I-4)+(b-10), (I-4)+(b-11), (I-4)+(b-12), (I-4)+(b-13), (I-4)+(b-14), (I-4)+(S3-1), (I-4)+(S3-2), (I-4)+(S3-3), (I-4)+(S3-4), (I-4)+(S3-5), (I-4)+(h-1), (I-4)+(h-2), (I-4)+(V-1), (I-4)+(V-2), (I-4)+(V-3), (I-4)+(V-4), (I-4)+(V-5), (I-4)+(V-6).

(I-5)+(II-0), (I-5)+(II-1), (I-5)+(II-2), (I-5)+(II-3), (I-5)+(II-4), (I-5)+(II-5), (I-5)+(II-6), (I-5)+(II-9), (I-5)+(II-12), (I-5)+(III-1), (I-5)+(III-4), (I-5)+(III-10), (I-5)+(III-11), (I-5)+(IV-1), (I-5)+(IV-2), (I-5)+(IV-3), (I-5)+(IV-4), (I-5)+(IV-5), (I-5)+(b-1), (I-5)+(b-2), (I-5)+(b-3), (I-5)+(b-4), (I-5)+(b-5), (I-5)+(b-6), (I-5)+(b-7), (I-5)+(b-8), (I-5)+(b-9), (I-5)+(b-10), (I-5)+(b-11), (I-5)+(b-12), (I-5)+(b-13), (I-5)+(b-14), (I-5)+(S3-1), (I-5)+(S3-2), (I-5)+(S3-3), (I-5)+(S3-4), (I-5)+(S3-5), (I-5)+(h-1), (I-5)+(h-2), (I-5)+(V-1), (I-5)+(V-2), (I-5)+(V-3), (I-5)+(V-4), (I-5)+(V-5), (I-5)+(V-6).

(I-6)+(II-0), (I-6)+(II-1), (I-6)+(II-2), (I-6)+(II-3), (I-6)+(II-4), (I-6)+(II-5), (I-6)+(II-6), (I-6)+(II-9), (I-6)+(II-12), (I-6)+(III-1), (I-6)+(III-4), (I-6)+(III-10), (I-6)+(III-11), (I-6)+(IV-1), (I-6)+(IV-2), (I-6)+(IV-3), (I-6)+(IV-4), (I-6)+(IV-5), (I-6)+(b-1), (I-6)+(b-2), (I-6)+(b-3), (I-6)+(b-4), (I-6)+(b-5), (I-6)+(b-6), (I-6)+(b-7), (I-6)+(b-8), (I-6)+(b-9), (I-6)+(b-10), (I-6)+(b-11), (I-6)+(b-12), (I-6)+(b-13), (I-6)+(b-14), (I-6)+(S3-1), (I-6)+(S3-2), (I-6)+(S3-3), (I-6)+(S3-4), (I-6)+(S3-5),(I-6)+(h-1), (I-6)+(h-2), (I-6)+(V-1), (I-6)+(V-2), (I-6)+(V-3), (I-6)+(V-4), (I-6)+(V-5), (I-6)+(V-6).

(I-7)+(II-0), (I-7)+(II-1), (I-7)+(II-2), (I-7)+(II-3), (I-7)+(II-4), (I-7)+(II-5), (I-7)+(II-6), (I-7)+(II-9), (I-7)+(II-12), (I-7)+(III-1), (I-7)+(III-4), (I-7)+(III-10), (I-7)+(III-11), (I-7)+(IV-1), (I-7)+(IV-2), (I-7)+(IV-3), (I-7)+(IV-4), (I-7)+(IV-5), (I-7)+(b-1), (I-7)+(b-2), (I-7)+(b-3), (I-7)+(b-4), (I-7)+(b-5), (I-7)+(b-6), (I-7)+(b-7), (I-7)+(b-8), (I-7)+(b-9), (I-7)+(b-10), (I-7)+(b-11), (I-7)+(b-12), (I-7)+(b-13), (I-7)+(b-14), (I-7)+(S3-1), (I-7)+(S3-2), (I-7)+(S3-3), (I-7)+(S3-4), (I-7)+(S3-5), (I-7)+(h-1), (I-7)+(h-2), (I-7)+(V-1), (I-7)+(V-2), (I-7)+(V-3), (I-7)+(V-4), (I-7)+(V-5), (I-7)+(V-6).

(I-8)+(II-0), (I-8)+(II-1), (I-8)+(II-2), (I-8)+(III-3), (I-8)+(II-4), (I-8)+(II-5), (I-8)+(II-6), (I-8)+(II-9), (I-8)+(II-12), (I-8)+(III-1), (I-8)+(III-4), (I-8)+(III-10), (I-8)+(III-11), (I-8)+(IV-1), (I-8)+(IV-2), (I-8)+(IV-3), (I-8)+(IV-4), (I-8)+(IV-5), (I-8)+(b-1), (I-8)+(b-2), (I-8)+(b-3), (I-8)+(b-4), (I-8)+(b-5), (I-8)+(b-6), (I-8)+(b-7), (I-8)+(b-8), (I-8)+(b-9), (I-8)+(b-10), (I-8)+(b-11), (I-8)+(b-12), (I-8)+(b-13), (I-8)+(b-14), (I-8)+(S3-1), (I-8)+(S3-2), (I-8)+(S3-3), (I-8)+(S3-

4), (I-8)+(S3-5), (I-8)+(h-1), (I-8)+(h-2), (I-8)+(V-1), (I-8)+(V-2), (I-8)+(V-3), (I-8)+(V-4), (I-8)+(V-5), (I-8)+(V-6).

(I-9)+(II-0), (I-9)+(II-1), (I-9)+(II-2), (I-9)+(II-3), (I-9)+(II-4), (I-9)+(II-5), (I-9)+(II-6), (I-9)+(II-9), (I-9)+(II-12), (I-9)+(III-1), (I-9)+(III-4), (I-9)+(III-10), (I-9)+(III-11), (I-9)+(IV-1), (I-9)+(IV-2), (I-9)+(IV-3), (I-9)+(IV-4), (I-9)+(IV-5), (I-9)+(b-1), (I-9)+(b-2), (I-9)+(b-3), (I-9)+(b-4), (I-9)+(b-5), (I-9)+(b-6), (I-9)+(b-7), (I-9)+(b-8), (I-9)+(b-9), (I9)+(b-10), (I-9)+(b-11), (I-9)+(b-12), (I-9)+(b-13), (I-9)+(b-14), (I-9)+(S3-1), (I-9)+(S3-2), (I-9)+(S3-3), (I-9)+(S3-4), (I-9)+(S3-5), (I-9)+(h-1), (I-9)+(h-2), (I-9)+(V-1), (I-9)+(V-2), (I-9)+(V-3), (I-9)+(V-4), (I-9)+(V-5), (I-9)+(V-6).

(I-10)+(II-0), (I-10)+(II-1), (I-10)+(II-2), (I-10)+(II3), (I-10)+(II-4), (I-10)+(II-5), (I-10)+(II-6), (I-10)+(II-9), (I-10)+(II-12), (I-10)+(III-1), (I-10)+(III-4), (I-10)+(III-10), (I-10)+(III-11), (I-10)+(IV-1), (I-10)+(IV-2), (I-10)+(IV-3), (I-10)+(IV-4), (I-10)+(IV-5), (I-10)+(b-1), (I-10)+(b-2), (I-10)+(b-3), (I-10)+(b4), (I-10)+(b-5), (I-10)+(b-6), (I-10)+(b-7), (I-10)+(b-8), (I-10)+(b-9), (I-10)+(b-10), (I-10)+(b-11), (I-10)+(b-12), (I-10)+(b-13), (I-10)+(b-14), (I-10)+(S3-1), (I-10)+(S3-2), (I-10)+(S3-3), (I-10)+(S3-4), (I-10)+(S3-5), (I-10)+(h-1), (I-10)+(h-2), (I-10)+(V-1), (I-10)+(V-2), (I-10)+(V-3), (I-10)+(V-4), (I-10)+(V-5), (I-10)+(V-6).

(I-11)+(II-0), (I-11)+(II-1), (I-11)+(II-2), (I-11)+(II-3), (I-11)+(II-4), (I-11)+(II-5), (I-11)+(II-6), (I-11)+(II-9), (I-11)+(II-12), (I-11)+(III-1), (I-11)+(III-4), (I-11)+(III-10), (I-11)+(III-11), (I-11)+(IV-1), (I-11)+(IV-2), (I-11)+(IV-3), (I-11)+(IV-4), (I-11)+(IV-5), (I-11)+(b-1), (I-11)+(b-2), (I-11)+(b-3), (I-11 )+(b-4), (I-11)+(b-5), (I-11)+(b-6), (I-11)+(b-7), (I-11)+(b-8), (I-11)+(b-9), (I-11)+(b-10), (I-11)+(b-11), (I-11)+(b-12), (I-11)+(b-13), (I-11)+(b-14), (I-11)+(S3-1), (I-11)+(S3-2), (I-11)+(S3-3), (I-11)+(S3-4), (I-11)+(S3-5), (I-11)+(h-1), (I-11)+(h-2), (I-11)+(V-1), (I-11)+(V-2), (I-11)+(V-3), (I-11)+(V-4), (I-11)+(V-5), (I-11)+(V-6).

(I-12)+(II-0), (I-12)+(II-1), (I-12)+(II-2), (I-12)+(II-3), (I-12)+(II-4), (I-12)+(II-5), (I-12)+(II-6), (I-12)+(II-9), (I-12)+(II-12), (I-12)+(III-1), (I-12)+(III-4), (I-12)+(III-10), (I-12)+(III-11), (I-12)+(IV-1), (I-12)+(IV-2), (I-12)+(IV-3), (I-12)+(IV-4), (I-12)+(IV-5), (I-12)+(b-1), (I-12)+(b-2), (I-12)+(b-3), (I-12)+(b-4), (I-12)+(b-5), (I-12)+(b-6), (I-12)+(b-7), (I-12)+(b-8), (I-12)+(b-9), (I-12)+(b-10), (I-12)+(b-11), (I-12),+(b-12), (I-12)+(b-13), (I-12)+(b-14), (I-12)+(S3-1), (I-12)+(S3-2), (I-12)+(S3-3), (I-12)+(S3-4), (I-12)+(S3-5), (I-12)+(h-1), (I-12)+(h-2), (I-12)+(V-1), (I-12)+(V-2), (I-12)+(V-3), (I-12)+(V-4), (I-12)+(V-5), (I-12)+(V-6).

(I-13)+(II-0), (I-13)+(II-1), (I-13)+(II-2), (I-13)+(II-3), (I-13)+(II-4), (I-13)+(II-5), (I-13)+(II-6), (I-13)+(II-9), (I-13)+(II-12), (I-13)+(III-1), (I-13)+(III-4), (I-13)+(III-10), (I-13)+(III-11), (I-13)+(IV-1), (I-13)+(IV-2), (I-13)+(IV-3), (I-13)+(IV-4), (I-13)+(IV-5), (I-13)+(b-1), (I-13)+(b-2), (I-13)+(b-3), (I-13)+(b-4), (I-13)+(b-5), (I-13)+(b-6), (I-13)+(b-7), (I-13)+(b-8), (I-13)+(b-9), (I-13)+(b-10), (I-13)+(b-11), (I-13)+(b-12), (I-13)+(b-13), (I-13)+(b-14), (I-13)+(S3-1), (I-13)+(S3-2)), I-13)+(S3-3), (I-13)+(S3-4), (I-13)+(S3-5), (I-13)+(h-1), (I-13)+(h-2), (I-13)+(V-1), (I-13)+(V-2), (I-13)+(V-3), (I-13)+(V-4), (I-13)+(V-5), (I-13)+(V-6).

(I-14)+(II-0), (I-14)+(II-1), (I-14)+(II-2), (I-14)+(II-3), (I-14)+(II-4), (I-14)+(II-5), (I-14)+(II-6), (I-14)+(II-9), (I-14)+(II-12), (I-14)+(III-1), (I-14)+(III-4), (I-14)+(III-10), (I-14)+(III-11), (I-14)+(IV-1), (I-14)+(IV-2), (I-14)+(IV-3), (I-14)+(IV4), (I-14)+(IV-5), (I-14)+(b-1), I-14)+(b-2), (I-14)+(b-3), (I-14)+(b-4), (I-14)+(b-5), (I-14)+(b-6), (I-14)+(b-7), (I-14)+(b-8), (I-14)+(b-9), (I-14)+(b-10), (I-14)+(b-11), (I-14)+(b-12), (I-14)+(b-13), (I-14)+(b-14), (I-14)+(S3-1), (I-14)+(S3-2), (I-14)+(S3-3), (I-14)+(S3-4), (I-14)+(S3-5), (I-14)+(h-1), (I-14)+(h-2), (I-14)+(V-1), (I-14)+(V-2), (I-14)+(V-3), (I-14)+(V-4), (I-14)+(V-5), (I-14)+(V-6).

(I-15)+(II-0), (I-15)+(II-1), (I-15)+(II-2), (I-15)+(II-3), (I-15)+(II-4), (I-15)+(II-5), (I-15)+(II-6), (I-15)+(II-9), (I-15)+(II-12), (I-15)+(III-1), (I-15)+(III-4), (I-15)+(III-10), (I-15)+(III-11), (I-15),+(IV-1), (I-15)+(IV-2), (I-15)+(IV-3), (I-15)+(IV-4), (I-15)+(IV-5), (I-15)+(b-1), (I-15)+(b-2), (I-15)+(b-3), (I-15)+(b-4), (I-15)+(b-5), (I-15)+(b-6), (I-15)+(b-7), (I-15)+(b-8), (I-15)+(b-9), (I-15)+(b-10), (I-15)+(b-11), (I-15)+(b-12), (I-15)+(b-13), (I-15)+(b-14), (I-15)+(S3-1), (I-15)+(S3-2), (I-15)+(S3-3), (I-15)+(S3-4), (I-15)+(S3-5), (I-15)+(h-1), (I-15),+(h-2), (I-15)+(V-1), (I-15)+(V-2), (I-15)+(V-3), (I-15)+(V-4), (I-15)+(V-5), (I-15)+(V-6).

(I-16)+(II-0), (I-16)+(II-1), (I-16)+(II-2), (I-16)+(II-3), (I-16)+(II-4), (I-16)+(II-5), (I-16)+(II-6), (I-16)+(II-9), (I-16)+(II-12), (I-16)+(III-1), (I-16)+(III-4), (I-16)+(III-10), (I-16)+(III-11), (I-16)+(IV-1), (I-16)+(IV-2), (I-16)+(IV-3), (I-16)+(IV-4), (I-16)+(IV-5), (I-16)+(b-1), (I-16)+(b-2), (I-16)+(b-3), (I-16)+(b-4), (I-16)+(b-5), (I-16)+(b-6), (I-16)+(b-7), (I-16)+(b-8), (I-16)+(b-9), (I-16)+(b-10), (I-16)+(b-11), (I-16)+(b-12), (I-16)+(b-13), (I-16)+(b-14), (I-16)+(S3-1), (I-16)+(S3-2), (I-16)+(S3-3), (I-16)+(S3-4), (I-16)+(S3-5), (I-16)+(h-1), (I-16)+(h-2), (I-16)+(V-1), (I-16)+(V(-2), (I-16)+(V-3), (I-16)+(V(-4), (I-16)+(V-5), (I-16)+(V-6).

(I-17)+(II-0), (I-17)+(II-1), (I-17)+(II-2), (I-17)+(II-3), (I-17)+(II-4), (I-17)+(II-5), (I-17)+(II-6), (I-17)+(II-9), (I-17)+(II-12), (I-17)+(III-1), (I-17)+(III-4), (I-17)+(III-10), (I-17)+(III-11), (I-17)+(IV-1), (I-17)+(IV-2), (I-17)+(IV-3), (I-17)+(IV-4), (I-17)+(IV-5), (I-17)+(b-1), (I-17)+(b-2), (I-17)+(b-3), (I-17)+(b-4), (I-17)+(b-5), (I-17)+(b-6), (I-17)+(b-7), (I-17)+(b-8), (I-17)+(b-9), (I-17)+(b-10), (I-17)+(b-11), (I-17)+(b-12), (I-17)+(b-13), (I-17)+(b-14), (I-17)+(S3-1), (I-17)+(S3-2), (I-17)+(S3-3), (I-17)+(S34), (I-17)+(S3-5), (I-17)+(h-1), (I-17)+(h-2), (I-17)+(V-1), (I-17)+(V-2), (I-17)+(V-3), (I-17)+(V-4), (I-17)+(V-5), (I-17)+(V-6).

(I-18)+(II-0), (I-18)+(II-1), (I-18)+(II-2), (I-18)+(II-3), (I-18)+(II-4), (I-18)+(II-5), (I-18)+(II-6), (I-18)+(II-9), (I-18)+(II-12), (I-18)+(III-1), (I-18)+(III-4), (I-18)+(III-10), (I-18)+(III-11), (I-18)+(IV-1), (I-18)+(IV-2), (I-18)+(IV-3), (I-18)+(IV-4), (I-18)+(IV-5), (I-18)+(b-1), (I-18)+(b-2), (I-18)+(b-3), (I-18)+(b-4), (I-18)+(b-5), (I-18)+(b-6), (I-18)+(b-7), (I-18)+(b-8), (I-18)+(b-9), (I-18)+(b-10), (I-18)+(b-11), (I-18)+(b-12), (I-18)+(b-13), (I-18)+(b-14), (I-18)+(S3-1), (I-18)+(S3-2), (I-18)+(S3-3), (I-18)+(S3-4), (I-18)+(S3-5), (I-18)+(h-1), (I-18)+(h-2), (I-18)+(V-1), (I-18)+(V-2), (I-18)+(V-3), (I-18)+(V-4), (I-18)+(V-5), (I-18)+(V-6).

(I-19)+(II-0), (I-19)+(II-1), (I-19)+(II-2), (I-19)+(II-3), (I-19)+(II-4), (I-19)+(II-5), (I-19)+(II-6), (I-19)+(II-9), (I-19)+(II-12), (I-19)+(III-1), (I-19)+(III-4), (I-19)+(III-10), (I-19)+(III-11), (I-19)+(IV-1), (I-19)+(IV-2), (I-19)+(IV-3), (I-19)+(IV-4), (I-19)+(IV-5), (I-19)+(b-1), (I-19)+(b-2), (I-19)+(b-3), (I-19)+(b-4), (I-19)+(b-5), (I-19)+(b-6), (I-19)+(b-7), (I-19)+(b-8), (I-19)+(b-9), (I-19)+(b-10), (I-19)+(b-11), (I-19)+(b-12), (I-19)+(b-13), (I-19)+(b-14), (I-19)+(S3-1), (I-19)+(S3-2), (I-19)+(S3-3), (I-19)+(S3-4), (I-19)+(S3-5), (I-19)+(h-1), (I-19)+(h-2), (I-19)+(V-1), (I-19)+(V-2), (I-19)+(V-3), (I-19)+(V-4), (I-19)+(V-5), (I-19)+(V-6).

(I-20)+(II-0), (I-20)+(II-1), (I-20)+(II-2), (I-20)+(II-3), (I-20)+(II-4), (I-20)+(II-5), (I-20)+(II-6), (I-20)+(II-9), (I-20)+(II-12), (I-20)+(III-1), (I-20)+(III-4), (I-20)+(III-10), (I-20)+(III-11), (I-20)+(IV-1), (I-20)+(IV-2), (I-20)+(IV-3), (I-20)+(IV-4), (I-20)+(IV-5), (I-20)+(b-1), (I-20)+(b-2), (I-20)+(b-3), (I-20)+(b-4), (I-20)+(b-5), (I-20)+(b-6), (I-20)+(b-7), (I-20)+(b-8), (I-20)+(b-9), (I-20)+(b-10), (I-20)+(b-11), (I-20)+(b-12), (I-20)+(b-13), (I-20)+(b-14), (I-20)+(S3-1), (I-20)+(S3-2), (I-20)+(S3-3), (I-20)+(S3-4), (I-20)+(S3-

5), (I-20)+(h-1), (I-20)+(h-2), (I-20)+(V-1), (I-20)+(V-2), (I-20)+(V-3), (I-20)+(V-4), (I-20)+(V-5), (I-20)+(V-6).

(I-21)+(II-0), (I-21)+(II-1), (I-21)+(II-2), (I-21)+(II-3), (I-21)+(II-4), (I-21)+(II-5), (I-21)+(II-6), (I-21)+(II-9), (I-21)+(II-12), (I-21)+(III-1), (I-21)+(III-4), (I-21)+(III-10), (I-21)+(III-11), (I-21)+(IV-1), (I-21)+(IV-2), (I-21)+(IV-3), (I-21)+(IV-4), (I-21)+(IV-5), (I-21)+(b-1), (I-21)+(b-2), (I-21)+(b-3), (I-21)+(b-4), (I-21)+(b-5), (I-21)+(b-6), (I-21)+(b-7), (I-21)+(b-8), (I-21)+(b-9), (I-21)+(b-10), (I-21)+(b-11), (I-21)+(b-12), (I-21)+(b-13), (I-21)+(b-14), (I-21)+(S3-1), (I-21)+(S3-2), (I-21)+(S3-3), (I-21)+(S3-4), (I-21)+(S3-5), (I-21)+(h-1), (I-21)+(h-2), (I-21)+(V-1), (I-21)+(V-2), (I-21)+(V-3), (I-21)+(V-4), (I-21)+(V-5), (I-21)+(V-6).

(I-22)+(II-0), (I-22)+(II-1), (I-22)+(II-2), (I-22),+(II-3), (I-22)+(II-4), (I-22)+(II-5), (I-22)+(II-6), (I-22)+(II-9), (I-22),+(II-12), (I-22)+(III-1), (I-22)+(III-4), (I-22)+(III-10), (I-22)+(III-11), (I-22)+(IV-1), (I-22)+(IV-2), (I-22)+(IV-3), (I-22)+(IV-4), (I-22)+(IV-5), (I-22)+(b-1), (I-22)+(b-2), (I-22)+(b-3), (I-22)+(b-4), (I-22)+(b-5), (I-22)+(b-6), (I-22)+(b-7), (I-22)+(b-8), (I-22)+(b-9), (I-22)+(b-10), (I-22)+(b-11), (I-11), (I-22)+(b-12), (I-22)+(b-13), (I-22)+(b-14), (I-22)+(S3-1), (I-22)+(S3-2), (I-22)+(S3-3), (I-22)+(S3-4), (I-22)+(S3-5), (I-22)+(h-1), (I-22)+(V-1), (I-22)+(V-2), (I-22)+(V-3), (I-22)+(V-4), (I-22)+(V-5), (I-22)+(V-6).

(I-23)+(II-0), (I-23)+(II-1), (I-23)+(II-2), (I-23)+(II-3), (I-23)+(II-4), (I-23)+(II-5), (I-23)+(II-6), (I-23)+(II-9), (I-23)+(II-12), (I-23)+(III-1), (I-23)+(III-4), (I-23)+(III-10), (I-23)+(III-11), (I-23)+(IV-1), (I-23)+(IV-2), (I-23)+(IV-3), (I-23)+(IV-4), (I-23)+(IV-5), (I-23)+(b-1), (I-23)+(b-2), (I-23)+(b-3), (I-23)+(b-4), (I-23)+(b-5), (I-23)+(b-6), (I-23)+(b-7), (I-23)+(b-8), (I-23)+(b-9), (I-23)+(b-10), (I-23)+(b-11), (I-23)+(b-12), (I-23)+(b-13), (I-23)+(b-14), (I-23)+(S3-1), (I-23)+(S3-2), (I-23)+(S3-3), (I-23)+(S3-4), (I-23)+(S3-5), (I-23)+(h-1), (I-23)+(h-2), (I-23)+(V-1), (I-23)+(V-2), (I-23)+(V-3), (I-23)+(V-4), (I-23)+(V-5), (I-23)+(V-6).

(I-24)+(II-0), (I-24)+(II-1), (I-24)+(II-2), (I-24)+(II-3), (I-24)+(II-4), (I-24)+(II-5), (I-24)+(II-6), (I-24)+(II-9), (I-24)+(II-12), (I-24)+(III-1), (I-24)+(III-4), (I-24)+(III-10), (I-24)+(III-11), (I-24)+(IV-1), (I-24)+(IV-2), (I-24)+(IV-3), (I-24)+(IV-4), (I-24)+(IV-5), (I-24)+(b-1), (I-24)+(b-2), (I-24)+(b-3), (I-24)+(b-4), (I-24)+(b-5), (I-24)+(b-6), (I-24)+(b-7), (I-24)+(b-8), (I-24)+(b-9), (I-24)+(b-10), (I-24)+(b-11), (I-24)+(b-12), (I-24)+(b-13), (I-24)+(b-14), (I-24)+(S3-1), (I-24)+(S3-2), (I-24)+(S3-3), (I-24)+(S34), (I-24)+(S3-5), (I-24)+(h-1), (I-24)+(h-2), (I-24)+(V-1), (I-24)+(V-2), (I-24)+(V-3), (I-24)+(V-4), (I-24)+(V-5), (I-24)+(V-6).

(I-25)+(II-0), (I-25)+(II-1), (I-25)+(II-2), (I-25)+(II-3), (I-25)+(II-4), (I-25)+(II-5), (I-25)+(II-6), (I-25)+(II-9), (I-25)+(II-12), (I-25)+(III-1), (I-25)+(III-4), (I-25)+(III-10), (I-25)+(III-11), (I-25)+(IV-1), (I-25)+(IV-2), (I-25)+(IV-3), (I-25)+(IV-4), (I-25)+(IV-5), (I-25)+(b-1), (I-25)+(b-2), (I-25)+(b-3), (I-25)+(b-4), (I-25)+(b-5), (I-25)+(b-6), (I-25)+(b-7), (I-25)+(b-8), (I-25)+(b-9), (I-25)+(b-10), (I-25)+(b-11), (I-25)+(b-12), (I-25)+(b-13), (I-25)+(b-14), (I-25)+(S3-1), (I-25)+(S3-2), (I-25)+(S3-3), (I-25)+(S3-4), (I-25)+(S3-5), (I-25)+(h-1), (I-25)+(h-2), (I-25)+(V-1), (I-25)+(V-2), (I-25)+(V-3), (I-25)+(V-4), (I-25)+(V-5), (I-25)+(V-6).

(I-26)+(II-0), (I-26)+(II-1), (I-26)+(II-2), (I-26)+(II-3), (I-26)+(II-4), (I-26)+(II-5), (I-26)+(II-6), (I-26)+(II-9), (I-26)+(II-12), (I-26)+(III-1), (I-26)+(III-4), (I-26)+(III-10), (I-26)+(III-11), (I-26)+(IV-1), (I-26)+(IV-2), (I-26)+(IV-3), (I-26)+(IV-4), (I-26)+(IV-5), (I-26)+(b-1), (I-26)+(b-2), (I-26)+(b-3), (I-26)+(b-4), (I-26)+(b-5), (I-26)+(b-6), (I-26)+(b-7), (I-26)+(b-8), (I-26)+(b-9), (I-26)+(b-10), (I-26)+(b-11), (I-26)+(b-12), (I-26)+(b-13), (I-26)+(b-14), (I-26)+(S3-1), (I-26)+(S3-2), (I-26)+(S3-3), (I-26)+(S3-4), (I-26)+(S3-5), (I-26)+(h-1), (I-26)+(h-2), (I-26)+(V-1), (I-26)+(V-2), (I-26)+(V-3), (I-26)+(V-4), (I-26)+(V-5), (I-26)+(V-6).

(I-27)+(II-0), (I-27)+(II-1), (I-27)+(II-2), (I-27)+(II-3), (I-27)+(II-4), (I-27)+(II-5), (I-27)+(II-6), (I-27)+(II-9), (I-27)+(II-12), (I-27)+(III-1), (I-27)+(III-4), (I-27)+(III-10), (I-27)+(III-11), (I-27)+(IV-1), (I-27)+(IV-2), (I-27)+(IV-3), (I-27)+(IV-4), (I-27)+(IV-5), (I-27)+(b-1), (I-27)+(b-2), (I-27)+(b-3), (I-27)+(b-4), (I-27)+(b-5), (I-27)+(b-6), (I-27)+(b-7), (I-27)+(b-8), (I-27)+(b-9), (I-27)+(b-10), (I-27)+(b-11), (I-27)+(b-12), (I-27)+(b-13), (I-27)+(b-14), (I-27)+(S3-1), (I-27)+(S3-2), (I-27)+(S3-3), (I-27)+(S3-4), (I-27)+(S3-5), (I-27)+(h-1), (I-27)+(h-2), (I-27)+(V-1), (I-27)+(V-2), (I-27)+(V-3), (I-27)+(V-4), (I-27)+(V-5), (I-27)+(V-6).

(I-28)+(II-0), (I-28)+(II-1), (I-28)+(II-2), (I-28)+(II-3), (I-28)+(II-4), (I-28)+(II-5), (I-28)+(II-6), (I-28)+(II-9), (I-28)+(II-12), (I-28)+(III-1), (I-28)+(III-4), (I-28)+(III-10), (I-28)+(III-11), (I-28)+(IV-1), (I-28)+(IV-2), (I-28)+(IV-3), (I-28)+(IV-4), (I-28)+(IV-5), (I-28)+(b-1), (I-28)+(b-2), (I-28)+(b-3), (I-28)+(b-4), (I-28)+(b-5), (I-28)+(b-6), (I-28)+(b-7), (I-28)+(b-8), (I-28)+(b-9), (I-28)+(b-10), (I-28)+(b-11), (I-28)+(b-12), (I-28)+(b-13), (I-28)+(b-14), (I-28)+(S3-1), (I-28)+(S3-2), (I-28)+(S3-3), (I-28)+(S3-4), (I-28)+(S3-5), (I-28)+(h-1), (I-28)+(h-2), (I-28)+(V-1), (I-28)+(V-2), (I-28)+(V-3), (I-28)+(V-4), (I-28)+(V-5), (I-28)+(V-6).

(I-29)+(II-0), (I-29)+(II-1), (I-29)+(II-2), (I-29)+(II-3), (I-29)+(II-4), (I-29)+(II-5), (I-29)+(II-6), (I-29)+(II-9), (I-29)+(II-12), (I-29)+(III-1), (I-29)+(III-4), (I-29)+(III-10), (I-29)+(III-11), (I-29)+(IV-1), (I-29)+(IV-2), (I-29)+(IV-3), (I-29)+(IV-4), (I-29)+(IV-5), (I-29)+(b-1), (I-29)+(b-2), (I-29)+(b-3), (I-29)+(b-4), (I-29)+(b-5), (I-29)+(b-6), (I-29)+(b-7), (I-29)+(b-8), (I-29)+(b-9), (I-29)+(b-10), (I-29)+(b-11), (I-29)+(b-12), (I-29)+(b-13), (I-29)+(b-14), (I-29)+(S3-1), (I-29)+(S3-2), (I-29)+(S3-3), (I-29)+(S3-4), (I-29)+(S3-5), (I-29)+(h-1), (I-29)+(h-2), (I-29)+(V-1), (I-29)+(V-2), (I-29)+(V-3), (I-29)+(V-4), (I-29)+(V-5), (I-29)+(V-6).

(I-30)+(II-0), (I-30)+(II-1), (I-30)+(II-2), (I-30)+(II-3)+(II-4), (I-30)+(II-5), (I-30)+(II-6), (I-30)+(II-9), (I-30)+(II-12), (I-30)+(III-1), (I-30)+(III-4), (I-30)+(III-10), (I-30)+(III-11), (I-30)+(IV-1), (I-30)+(IV-2), (I-30)+(IV-3), (I-30)+(IV-4), (I-30)+(IV-5), (I-30)+(b-1), (I-30)+(b-2), (I-30)+(b-3), (I-30)+(b-4), (I-30)+(b-5), (I-30)+(b-6), (I-30)+(b-7), (I-30)+(b-8), (I-30)+(b-9), (I-30)+(b-10), (I-30)+(b-11), (I-30)+(b-12), (I-30)+(b-13), (I-30)+(b-14), (I-30)+(S3-1), (I-30)+(S3-2), (I-30)+(S3-3), (I-30)+(S3-4), (I-30)+(S3-5), (I-30)+(h-1), (I-30)+(h-2), (I-30)+(V-1), (I-30)+(V-2), (I-30)+(V-3), (I-30)+(V-4), (I-30)+(V-5), (I-30)+(V-6).

(I-31)+(II-0), (I-31)+(II-1), (I-31)+(II-2), (I-31)+(II-3), (I-31)+(II-4), (I-31)+(II-5), (I-31)+(II-6), (I-31)+(II-9), (I-31)+(II-12), (I-31)+(III-1), (I-31)+(III-4), (I-31)+(III-10), (I-31)+(III-11), (I-31)+(IV-1), (I-31)+(IV-2), (I-31)+(IV-3), (I-31)+(IV-4), (I-31)+(IV-5), (I-31)+(b-1), (I-31)+(b-2), (I-31)+(b-3), (I-31)+(b-4), (I-31)+(b-5), (I-31)+(b-6), (I-31)+(b-7), (I-31)+(b-8), (I-31)+(b-9), (I-31)+(b-10), (I-31)+(b-11), (I-31)+(b-12), (I-31)+(b-13), (I-31)+(b-14), (I-31)+(S3-1), (I-31)+(S3-2), (I-31)+(S3-3), (I-31)+(S3-4), (I-31)+(S3-5), (I-31)+(h-1), (I-31)+(h-2), (I-31)+(V-1), (I-31)+(V-2), (I-31)+(V-3), (I-31)+(V-4), (I-31)+(V-5), (I-31)+(V-6).

(I-32)+(II-0), (I-32)+(II-1), (I-32)+(II-2), (I-32)+(II-3), (I-32)+(II-4), (I-32)+(II-5), (I-32)+(II-6), (I-32)+(II-9), (I-32)+(II-12), (I-32)+(III-1), (I-32)+(III-4), (I-32)+(III-10), (I-32)+(III-11), (I-32)+(IV-1), (I-32)+(IV-2), (I-32)+(IV-3), (I-32)+(IV-4), (I-32)+(IV-5), (I-32)+(b-1), (I-32)+(b-2), (I-32)+(b-3), (I-32)+(b-4), (I-32)+(b-5), (I-32)+(b-6), (I-32)+(b-7), (I-32)+(b-8), (I-32)+(b-9), (I-32)+(b-10), (I-32)+(b-11), (I-32)+(b-12), (I-32)+(b-13), (I-32)+(b-14), (I-32)+(S3-1), (I-32)+(S3-2), (I-32)+(S3-3), (I-32)+(S3-4), (I-32)+(S3-

5), (I-32)+(h-1), (I-32)+(h-2), (I-32)+(V-1), (I-32)+(V-2), (I-32)+(V-3), (I-32)+(V-4), (I-32)+(V-5), (I-32)+(V-6).

(I-33)+(II-0), (I-33)+(II-1), (I-33)+(II-2), (I-33)+(II-3), (I-33)+(II-4), (I-33)+(II-5), (I-33)+(II-6), (I-33)+(II-9), (I-33)+(II-12), (I-33)+(III-1), (I-33)+(III-4), (I-33)+(III-10), (I-33)+(III-11), (I-33)+(IV-1), (I-33)+(IV-2), (I-33)+(IV-3), (I-33)+(IV-4), (I-33)+(IV-5), (I-33)+(b-1), (I-33)+(b-2), (I-33)+(b-3), (I-33)+(b-4), (I-33)+(b-5), (I-33)+(b-6), (I-33)+(b-7), (I-33)+(b-8), (I-33)+(b-9), (I-33)+(b-10), (I-33)+(b-11), (I-33)+(b-12), (I-33)+(b-13), (I-33)+(b-14), (I-33)+(S3-1), (I-33)+(S3-2), (I-33)+(S3-3), (I-33)+(S3-4), (I-33)+(S3-5), (I-33)+(h-1), (I-33)+(h-2), (I-33)+(V-1), (I-33)+(V-2), (I-33)+(V-3), (I-33)+(V-4), (I-33)+(V-5), (I-33)+(V-6).

(I-34)+(II-0), (I-34)+(II-1), (I-34)+(II-2), (I-34)+(II-3), (I-34)+(II-4), (I-34)+(II-5), (I-34)+(II-6), (I-34)+(II-9), (I-34)+(II-12), (I-34)+(III-1), (I-34)+(III-4), (I-34)+(III-10), (I-34)+(III-11), (I-34)+(IV-1), (I-34)+(IV-2), (I-34)+(IV-3), (I-34)+(IV-4), (I-34)+(IV-5), (I-34)+(b-1), (I-34)+(b-2), (I-34)+(b-3), (I-34)+(b-4), (I-34)+(b-5), (I-34)+(b-6), (I-34)+(b-7), (I-34)+(b-8), (I-34)+(b-9), (I-34)+(b-10), (I-34)+(b-11), (I-34)+(b-12), (I-34)+(b-13), (I-34)+(b-14), (I-34)+(S3-1), (I-34)+(S3-2), (I-34)+(S3-3), (I-3-4)+(S3-4), (I-34)+(S3-5), (I-34)+(h-1), (I-34)+(h-2), (I-34)+(V-1), (I-34)+(V-2), (I-34)+(V-3), (I-34)+(V-4), (I-34)+(V-5), (I-34)+(V-6).

(I-35)+(II-0), (I-35)+(II-1), (I-35)+(II-2), (I-35)+(II-3), (I-35)+(II-4), (I-35)+(II-5), (I-35)+(II-6), (I-35)+(II-9), (I-35)+(II-12), (I-35)+(III-1), (I-35)+(III-4), (I-35)+(III-10), (I-35)+(III-11), (I-35)+(IV-1), (I-35)+(IV-2), (I-35)+(IV-3), (I-35)+(IV-4), (I-35)+(IV-5), (I-35)+(b-1), (I-35)+(b-2), (I-35)+(b-3), (I-35)+(b-4), (I-35)+(b-5), (I-35)+(b-6), (I-35)+(b-7), (I-35)+(b-8), (I-35)+(b-9), (I-35)+(b-10), (I-35)+(b-11), (I-35)+(b-12), (I-35)+(b-13), (I-35)+(b-14), (I-35)+(S3-1), (I-35)+(S3-2), (I-35)+(S3-3), (I-35)+(S3-4), (I-35)+(S3-5), (I-35)+(h-1), (I-35)+(h-2), (I-35)+(V-1), (I-35)+(V-2), (I-35)+(V-3), (I-35)+(V-4), (I-35)+(V-5), (I-35)+(V-6).

(I-36)+(II-0), (I-36)+(II-1), (I-36)+(II-2), (I-36)+(II-3), (I-36)+(II-4), (I-36)+(II-5), (I-36)+(II-6), (I-36)+(II-9), (I-36)+(II-12), (I-36)+(III-1), (I-36)+(III-4), (I-36)+(III-10), (I-36)+(III-11), (I-36)+(IV-1), (I-36)+(IV-2), (I-36)+(IV-3), (I-36)+(IV-4), (I-36)+(IV-5), (I-36)+(b-1), (I-36)+(b-2), (I-36)+(b-3), (I-36)+(b-4), (I-36)+(b-5), (I-36)+(b-6), (I-36)+(b-7), (I-36)+(b-8), (I-36)+(b-9), (I-36)+(b-10), (I-36)+(b-11), (I-36)+(b-12), (I-36)+(b-13), (I-36)+(b-14), (I-36)+(S3-1), (I-36)+(S3-2), (I-36)+(S3-3), (I-36)+(S3-4), (I-36)+(S3-5), (I-36)+(h-1), (I-36)+(h-2), (I-36)+(V-1), (I-36)+(V-2), (I-36)+(V-3), (I-36)+(V-4), (I-36)+(V-5), (I-36)+(V-6).

(I-37)+(II-0), (I-37)+(II-1), (I-37)+(II-2), (I-37)+(II-3), (I-37)+(II-4), (I-37)+(II-5), (I-37)+(II-6), (I-37)+(II-9), (I-37)+(II-12), (I-37)+(III-1), (I-37)+(III-4), (I-37)+(III-10), (I-37)+(III-11), (I-37)+(IV-1), (I-37)+(IV-2), (I-37)+(IV-3), (I-37)+(IV-4), (I-37)+(IV-5), (I-37)+(b-1), (I-37)+(b-2), (I-37)+(b-3), (I-37)+(b-4), (I-37)+(b-5), (I-37)+(b-6), (I-37)+(b-7), (I-37)+(b-8), (I-37)+(b-9), (I-37)+(b-10), (I-37)+(b-11), (I-37)+(b-12), (I-37)+(b-13), (I-37)+(b-14), (I-37)+(S3-1), (I-37)+(S3-2), (I-37)+(S3-3), (I-37)+(S3-4), (I-37)+(S3-5), (I-37)+(h-1), (I-37)+(h-2), (I-37)+(V-1), (I-37)+(V-2), (I-37)+(V-3), (I-37)+(V-4), (I-37)+(V-5), (I-37)+(V-6).

(I-38)+(II-0), (I-38)+(II-1), (I-38)+(II-2), (I-38)+(II-3), (I-38)+(II-4), (I-38)+(II-5), (I-38)+(II-6), (I-38)+(II-9), (I-38)+(II-12), (I-38)+(III-1), (I-38)+(III-4), (I-38)+(III-10), (I-38)+(III-11), (I-38)+(IV-1), (I-38)+(IV-2), (I-38)+(IV-3), (I-38)+(IV-4), (I-38)+(IV-5), (I-38)+(b-1), (I-38)+(b-2), (I-38)+(b-3), (I-38)+(b-4), (I-38)+(b-5), (I-38)+(b-5), (I-38)+(b-7), (I-38)+(b-8), (I-38)+(b-9), (I-38)+(b-10), (I-38)+(b-11), (I-38)+(b-12), (I-38)+(b-13), (I-38)+(b-14), (I-38)+(S3-1), (I-38)+(S3-2), (I-38)+(S3-3), (I-38)+(S3-4), (I-38)+(S3-5), (I-38)+(h-1), (I-38)+(h-2), (I-38)+(V-1), (I-38)+(V-2), (I-38)+(V-3), (I-38)+(V-4), (I-38)+(V-5), (I-38)+(V-6).

(I-39)+(II-0), (I-39)+(II-1), (I-39)+(II-2), (I-39)+(II-3), (I-39)+(II-4), (I-39)+(II-5), (I-39)+(II-6), (I-39)+(II-9), (I-39)+(II-12), (I-39)+(III-1), (I-39)+(III-4), (I-39)+(III-10), (I-39)+(III-11), (I-39)+(IV-1), (I-39)+(IV-2), (I-39)+(IV-3), (I-39)+(IV-4), (I-39)+(IV-5), (I-39)+(b-1), (I-39)+(b-2), (I-39)+(b-3), (I-39)+(b-4), (I-39)+(b-5), (I-39)+(b-6), (I-39)+(b-7), (I-39)+(b-8), (I-39)+(b-9), (I-39)+(b-10), (I-39)+(b-11), (I-39)+(b-12), (I-39)+(b-13), (I-39)+(b-14), (I-39)+(S3-1), (I-39)+(S3-2), (I-39)+(S3-3), (I-39)+(S3-4), (I-39)+(S3-5), (I-39)+(h-1), (I-39)+(h-2), (I-39)+(V-1), (I-39)+(V-2), (I-39)+(V-3), (I-39)+(V-4), (I-39)+(V-5), (I-39)+(V-6).

(I-40)+(II-0), (I-40)+(II-1), (I-40)+(II-2), (I-40)+(II-3), (I-40)+(II-4), (I-40)+(II-5), (I-40)+(II-6), (I-40)+(II-9), (I-40)+(II-12), (I-40)+(III-1), (I-40)+(III-4), (I-40)+(III-10), (I-40)+(III-11), (I-40)+(IV-1), (I-40)+(IV-2), (I-40)+(IV-3), (I-40)+(IV-4), (I-40)+(IV-5), (I-40)+(b-1), (I-40)+(b-2), (I-40)+(b-3), (I-40)+(b-4), (I-40)+(b-5), (I-40)+(b-6), (I-40)+(b-7), (I-40)+(b-8), (I-40)+(b-9), (I-40)+(b-10), (I-40)+(b-11), (I-40)+(b-12), (I-40)+(b-13), (I-40)+(b-14), (I-40)+(S3-1), (I-40)+(S3-2), (I-40)+(S3-3), (I-40)+(S3-4), (I-40)+(S3-5), (I-40)+(h-1), (I-40)+(h-2), (I-40)+(V-1), (I-40)+(S3-2), (I-40)+(V-3), (I-40)+(V-4), (I-40)+(V-5), (I-40)+(V-6).

(I-41)+(II-0), (I-41)+(II-1), (I-41)+(II-2), (I-41)+(II-3), (I-41)+(II-4), (I-41)+(II-5), (I-41)+(II-6), (I-41)+(II-9), (I-41)+(II-12), (I-41)+(III-1), (I-41)+(III-4), (I-41)+(III-10), (I-41)+(III-11), (I-41)+(IV-1), (I-41)+(IV-2), (I-41)+(IV-3), (I-41)+(IV-4), (I-41)+(IV-5), (I-41)+(b-1), (I-41)+(b-2), (I-41)+(b-3), (I-41)+(b-4), (I-41)+(b-5), (I-41)+(b-6), (I-41)+(b-7), (I-41)+(b-8), (I-41)+(b-9), (I-41)+(b-10), (I-41)+(b-11), (I-41)+(b-12), (I-41)+(b-13), (I-41)+(b-14), (I-41)+(S3-1), (I-41)+(S3-2), (I-41)+(S3-3), (I-41)+(S3-4), (I-41)+(S3-5), (I-41)+(h-1), (I-41)+(h-2), (I-41)+(V-1), (I-41)+(V-2), (I-41)+(V-3), (I-41)+(V-4), (I-41)+(V-5), (I-41)+(V-6).

(I-42)+(II-0), (I-42)+(II-1), (I-42)+(II-2), (I-42)+(II-3), (I-42)+(II-4), (I-42)+(II-5), (I-42)+(II-6), (I-42)+(II-9), (I-42)+(II-12), (I-42)+(III-1), (I-42)+(III-4), (I-42)+(III-10), (I-42)+(III-11), (I-42)+(IV-1), (I-42)+(IV-2), (I-42)+(IV-3), (I-42)+(IV-4), (I-42)+(IV-5), (I-42)+(b-1), (I-42)+(b-2), (I-42)+(b-3), (I-42)+(b-4), (I-42)+(b-5), (I-42)+(b-6), (I-42)+(b-7), (I-42)+(b-8), (I-42)+(b-9), (I-42)+(b-10), (I-42)+(b-11), (I-42)+(b-12), (I-42)+(b-13), (I-42)+(b-14), (I-42)+(S3-1), (I-42)+(S3-2), (I-42)+(S3-3), (I-42)+(S3-4), (I-42)+(S3-5), (I-42)+(h-1), (I-42)+(h-2), (I-42)+(V-1), (I-42)+(V-2), (I-42)+(V-3), (I-42)+(V-4), (I-42)+(V-5), (I-42)+(V-6).

(I-43)+(II-0), (I-43)+(II-1), (I-43)+(II-2), (I-43)+(II-3), (I-43)+(II-4), (I-43)+(II-5), (I-43)+(II-6), (I-43)+(II-9), (I-43)+(II-12), (I-43)+(III-1), (I-43)+(III-4), (I-43)+(III-10), (I-43)+(III-11), (I-43)+(IV-1), (I-43)+(IV-2), (I-43)+(IV-3), (I-43)+(IV-4), (I-43)+(IV-5), (I-43)+(b-1), (I-43)+(b-2), (I-43)+(b-3), (I-43)+(b-4), (I-43)+(b-5), (I-43)+(b-6), (I-43)+(b-7), (I-43)+(b-8), (I-43)+(b-9), (I-43)+(b-10), (I-43)+(b-11), (I-43)+(b-12), (I-43)+(b-13), (I-43)+(b-14), (I-43)+(S3-1), (I-43)+(S3-2), (I-43)+(S3-3), (I-43)+(S3-4), (I-43)+(S3-5), (I-43)+(h-1), (I-43)+(h-2), (I-43)+(V-1), (I-43)+(V-2), (I-43)+(V-3), (I-43)+(V-4), (I-43)+(V-5), (I-43)+(V-6).

(I-44)+(II-0), (I-44)+(II-1), (I-44)+(II-2), (I-44)+(II-3), (I-44)+(II-4), (I-44)+(II-5), (I-44)+(II-6), (I-44)+(II-9), (I-44)+(II-12), (I-44)+(III-1), (I-44)+(III-4), (I-44)+(III-10), (I-44)+(III-11), (I-44)+(IV-1), (I-44)+(IV-2), (I-44)+(IV-3), (I-44)+(IV-4), (I-44)+(IV-5), (I-44)+(b-1), (I-44)+(b-2), (I-44)+(b-3), (I-44)+(b-4), (I-44)+(b-5), (I-44)+(b-6), (I-44)+(b-7), (I-44)+(b-8), (I-44)+(b-9), (I-44)+(b-10), (I-44)+(b-11), (I-44)+(b-12), (I-44)+(b-13), (I-44)+(b-14), (I-44)+(S3-1), (I-44)+(S3-2), (I-44)+(S3-3), (I-44)+(S3-4), (I-44)+(S3-

5), (I-44)+(h-1), (I-44)+(h-2), (I-44)+(V-1), (I-44)+(V-2), (I-44)+(V-3), (I-44)+(V-4), (I-44)+(V-5), (I-44)+(V-6).

(I-45)+(II-0), (I-45)+(II-1), (I-45)+(II-2), (I-45)+(II-3), (I-45)+(II-4), (I-45)+(II-5), (I-45)+(II-6), (I-45)+(II-9), (I-45)+(II-12), (I-45)+(III-1), (I-45)+(III-4), (I-45)+(III-10), (I-45)+(III-11), (I-45)+(IV-1), (I-45)+(IV-2), (I-45)+(IV-3), (I-45)+(IV-4), (I-45)+(IV-5), (I-45)+(b-1), (I-45)+(b-2), (I-45)+(b-3), (I-45)+(b-4), (I-45)+(b-5), (I-45)+(b-6), (I-45)+(b-7), (I-45)+(b-8), (I-45)+(b-9), (I-45)+(b-10), (I-45)+(b-11), (I-45)+(b-12), (I-45)+(b-13), (I-45)+(b-14), (I-45)+(S3-1), (I-45)+(S3-2), (I-45)+(S3-3), (I-45)+(S3-4), (I-45)+(S3-5), (I-45)+(h-1), (I-45)+(h-2), (I-45)+(V-1), (I-45)+(V-2), (I-45)+(V-3), (I-45)+(V-4), (I-45)+(V-5), (I-45)+(V-6).

(I-46)+(II-0), (I-46)+(II-1), (I-46)+(II-2), (I-46)+(II-3), (I-46)+(II-4), (I-46)+(II-5), (I-46)+(II-6), (I-46)+(II-9), (I-46)+(II-12), (I-46)+(III-1), (I-46)+(III-4), (I-46)+(III-10), (I-46)+(III-11), (I-46)+(IV-1), (I-46)+(IV-2), (I-46)+(IV-3), (I-46)+(IV-4), (I-46)+(IV-5), (I-46)+(b-1), (I-46)+(b-2), (I-46)+(b-3), (I-46)+(b-4), (I-46)+(b-5), (I-46)+(b-6), (I-46)+(b-7), (I-46)+(b-8), (I-46)+(b-9), (I-46)+(b-10), (I-46)+(b-11), (I-46)+(b-12), (I-46)+(b-13), (I-46)+(b-14), (I-46)+(S3-1), (I-46)+(S3-2), (I-46)+(S3-3), (I-46)+(S3-4), (I-46)+(S3-5), (I-46)+(h-1), (I-46)+(h-2), (I-46)+(V-1), (I-46)+(V-2), (I-46)+(V-3), (I-46)+(V-4), (I-46)+(V-5), (I-46)+(V-6).

(I-47)+(II-0), (I-47)+(II-1), (I-47)+(II-2), (I-47)+(II-3), (I-47)+(II-4), (I-47)+(II-5), (I-47)+(II-6), (I-47)+(II-9), (I-47)+(II-12), (I-47)+(III-1), (I-47)+(III-4), (I-47)+(III-10), (I-47)+(III-11), (I-47)+(IV-1), (I-47)+(IV-2), (I-47)+(IV-3), (I-47)+(IV-4), (I-47)+(IV-5), (I-47)+(b-1), (I-47)+(b-2), (I-47)+(b-3), (I-47)+(b-4), (I-47)+(b-5), (I-47)+(b-6), (I-47)+(b-7), (I-47)+(b-8), (I-47)+(b-9), (I-47)+(b-10), (I-47)+(b-11), (I-47)+(b-12), (I-47)+(b-13), (I-47)+(b-14), (I-47)+(S3-1), (I-47)+(S3-2), (I-47)+(S3-3), (I-47)+(S3-4), (I-47)+(S3-5), (I-47)+(h-1), (I-47)+(h-2), (I-47)+(V-1), (I-47)+(V-2), (I-47)+(V-3), (I-47)+(V-4), (I-47)+(V-5), (I-47)+(V-6).

(I-48)+(II-0), (I-48)+(II-1), (I-48)+(II-2), (I-48)+(II-3), (I-48)+(II-4), (I-48)+(II-5), (I-48)+(II-6), (I-48)+(II-9), (I-48)+(II-12), (I-48)+(III-1), (I-48)+(III-4), (I-48)+(III-10), (I-48)+(III-11), (I-48)+(IV-1), (I-48)+(IV-2), (I-48)+(IV-3), (I-48)+(IV-4), (I-48)+(IV-5), (I-48)+(b-1), (I-48)+(b-2), (I-48)+(b-3), (I-48)+(b-4), (I-48)+(b-5), (I-48)+(b-6), (I-48)+(b-7), (I-48)+(b-8), (I-48)+(b-9), (I-48)+(b-10), (I-48)+(b-11), (I-48)+(b-12), (I-48)+(b-13), (I-48)+(b-14), (I-48)+(S3-1), (I-48)+(S3-2), (I-48)+(S3-3), (I-48)+(S3-4), (I-48)+(S3-5), (I-48)+(h-1), (I-48)+(h-2), (I-48)+(V-1), (I-48)+(V-2), (I-48)+(V-3), (I-48)+(V-4), (I-48)+(V-5), (I-48)+(V-6).

(I-49)+(II-0), (I-49)+(II-1), (I-49)+(II-2), (I-49)+(II-3), (I-49)+(II-4), (I-49)+(II-5), (I-49)+(II-6), (I-49)+(II-9), (I-49)+(II-12), (I-49)+(III-1), (I-49)+(III-4), (I-49)+(III-10), (I-49)+(III-11), (I-49)+(IV-1), (I-49)+(IV-2), (I-49)+(IV-3), (I-49)+(IV-4), (I-49)+(IV-5), (I-49)+(b-1), (I-49)+(b-2), (I-49)+(b-3), (I-49)+(b-4), (I-49)+(b-5), (I-49)+(b-6), (I-49)+(b-7), (I-49)+(b-8), (I-49)+(b-9), (I-49)+(b-10), (I-49)+(b-11), (I-49)+(b-12), (I-49)+(b-13), (I-49)+(b-14), (I-49)+(S3-1), (I-49)+(S3-2), (I-49)+(S3-3), (I-49)+(S3-4), (I-49)+(S3-5), (I-49)+(h-1), (I-49)+(h-2), (I-49)+(V-1), (I-49)+(V-2), (I-49)+(V-3), (I-49)+(V-4), (I-49)+(V-5), (I-49)+(V-6).

(I-50)+(II-0), (I-50)+(II-1), (I-50)+(II-2), (I-50)+(II-3), (I-50)+(II-4), (I-50)+(II-5), (I-50)+(II-6), (I-50)+(II-9), (I-50)+(II-12), (I-50)+(III-1), (I-50)+(III-4), (I-50)+(III-10), (I-50)+(III-11), (I-50)+(IV-1), (I-50)+(IV-2), (I-50)+(IV-3), (I-50)+(IV-4), (I-50)+(IV-5), (I-50)+(b-1), (I-50)+(b-2), (I-50)+(b-3), (I-50)+(b-4), (I-50)+(b-5), (I-50)+(b-6), (I-50)+(b-7), (I-50)+(b-8), (I-50)+(b-9), (I-50)+(b-10), (I-50)+(b-11), (I-50)+(b-12), (I-50)+(b-13), (I-50)+(b-14), (I-50)+(S3-1), (I-50)+(S3-2), (I-50)+(S3-3), (I-50)+(S3-4), (I-50)+(S3-5), (I-50)+(h-1), (I-50)+(h-2), (I-50)+(V-1), (I-50)+(V-2), (I-50)+(V-3), (I-50)+(V-4), (I-50)+(V-5), (I-50)+(V-6).

(I-51)+(II-0), (I-51)+(II-1), (I-51)+(II-2), (I-51)+(II-3), (I-51)+(II-4), (I-51)+(II-5), (I-51)+(II-6), (I-51)+(II-9), (I-51)+(II-12), (I-51)+(III-1), (I-51)+(III-4), (I-51)+(III-10), (I-51)+(III-11), (I-51)+(IV-1), (I-51)+(IV-2), (I-51)+(IV-3), (I-51)+(IV-4), (I-51)+(IV-5), (I-51)+(b-1), (I-51)+(b-2), (I-51)+(b-3), (I-51)+(b-4), (I-51)+(b-5), (I-51)+(b-6), (I-51)+(b-7), (I-51)+(b-8), (I-51)+(b-9), (I-51)+(b-10), (I-51)+(b-11), (I-51)+(b-12), (I-51)+(b-13), (I-51)+(b-14), (I-51)+(S3-1), (I-51)+(S3-2), (I-51)+(S3-3), (I-51)+(S3-4), (I-51)+(S3-5), (I-51)+(h-1), (I-51)+(h-2), (I-51)+(V-1), (I-51)+(V-2), (I-51)+(V-3), (I-51)+(V-4), (I-51)+(V-5), (I-51)+(V-6).

(I-52)+(II-0), (I-52)+(II-1), (I-52)+(II-2), (I-52)+(II-3), (I-52)+(II-4), (I-52)+(II-5), (I-52)+(II-6), (I-52)+(II-9), (I-52)+(II-12), (I-52)+(III-1), (I-52)+(III-4), (I-52)+(III-10), (I-52)+(III-11), (I-52)+(IV-1), (I-52)+(IV-2), (I-52)+(IV-3), (I-52)+(IV-4), (I-52)+(IV-5), (I-52)-(b-1), (I-52)+(b-2), (I-52)+(b-3), (I-52)+(b-4), (I-52)+(b-5), (I-52)+(b-6), (I-52)+(b-7), (I-52)+(b-8), (I-52)+(b-9), (I-52)+(b-10), (I-52)+(b-11), (I-52)+(b-12), (I-52)+(b-13), (I-52)+(b-14), (I-52)+(S3-1), (I-52)+(S3-2), (I-52)+(S3-3), (I-52)+(S3-4), (I-52)+(S3-5), (I-52)+(h-1), (I-52)+(h-2), (I-52)+(V-1), (I-52)+(V-2), (I-52)+(V-3), (I-52)+(V-4), (I-52)+(V-5), (I-52)+(V-6).

(I-53)+(II-0), (I-53)+(II-1), (I-53)+(II-2), (I-53)+(II-3), (I-53)+(II-4), (I-53)+(II-5), (I-53)+(II-6), (I-53)+(II-9), (I-53)+(II-12), (I-53)+(III-1), (I-53)+(III-4), (I-53)+(III-10), (I-53)+(III-11), (I-53)+(IV-1), (I-53)+(IV-2), (I-53)+(IV-3), (I-53)+(IV-4), (I-53)+(IV-5), (I-53)+(b-1), (I-53)+(b-2), (I-53)+(b-3), (I-53)+(b-4), (I-53)+(b-5), (I-53)+(b-6), (I-53)+(b-7), (I-53)+(b-8), (I-53)+(b-9), (I-53)+(b-10), (I-53)+(b-11), (I-53)+(b-12), (I-53)+(b-13), (I-53)+(b-14), (I-53)+(S3-1), (I-53)+(S3-2), (I-53)+(S3-3), (I-53)+(S3-4), (I-53)+(S3-5), (I-53)+(h-1), (I-53)+(h-2), (I-53)+(V-1), (I-53)+(V-2), (I-53)+(V-3), (I-53)+(V-4), (I-53)+(V-5), (I-53)+(V-6).

(I-54)+(II-0), (I-54)+(II-1), (I-54)+(II-2), (I-54)+(II-3), (I-54)+(II-4), (I-54)+(II-5), (I-54)+(II-6), (I-54)+(II-9), (I-54)+(II-12), (I-54)+(III-1), (I-54)+(III-4), (I-54)+(III-10), (I-54)+(III-11), (I-54)+(IV-1), (I-54)+(IV-2), (I-54)+(IV-3), (I-54)+(IV-4), (I-54)+(IV-5), (I-54)+(b-1), (I-54)+(b-2), (I-54)+(b-3), (I-54)+(b-4), (I-54)+(b-5), (I-54)+(b-6), (I-54)+(b-7), (I-54)+(b-8), (I-54)+(b-9), (I-54)+(b-10), (I-54)+(b-11), (I-54)+(b-12), (I-54)+(b-13), (I-54)+(b-14), (I-54)+(S3-1), (I-54)+(S3-2), (I-54)+(S3-3), (I-54)+(S3-4), (I-54)+(S3-5), (I-54)+(h-1), (I-54)+(h-2), (I-54)+(V-1), (I-54)+(V-2), (I-54)+(V-3), (I-54)+(V-4), (I-54)+(V-5), (I-54)+(V-6).

(I-55)+(II-0), (I-55)+(II-1), (I-55)+(II-2), (I-55)+(II-3), (I-55)+(II-4), (I-55)+(II-5), (I-55)+(II-6), (I-55)+(II-9), (I-55)+(II-12), (I-55)+(III-1), (I-55)+(III-4), (I-55)+(III-10), (I-55)+(III-11), (I-55)+(IV-1), (I-55)+(IV-2), (I-55)+(IV-3), (I-55)+(IV-4), (I-55)+(IV-5), (I-55)+(b-1), (I-55)+(b-2), (I-55)+(b-3), (I-55)+(b-4), (I-55)+(b-5), (I-55)+(b-6), (I-55)+(b-7), (I-55)+(b-8), (I-55)+(b-9), (I-55)+(b-10), (I-55)+(b-11), (I-55)+(b-12), (I-55)+(b-13), (I-55)+(b-14), (I-55)+(S3-1), (I-55)+(S3-2), (I-55)+(S3-3), (I-55)+(S34), (I-55)+(S3-5), (I-55)+(h-1), (I-55)+(h-2), (I-55)+(V-1), (I-55)+(V-2), (I-55)+(V-3), (I-55)+(V-4), (I-55)+(V-5), (I-55)+(V-6).

(I-56)+(II-0), (I-56)+(II-1), (I-56)+(II-2), (I-56)+(II-3), (I-56)+(II-4), (I-56)+(II-5), (I-56)+(II-6), (I-56)+(II-9), (I-56)+(II-12), (I-56)+(III-1), (I-56)+(III-4), (I-56)+(III-10), (I-56)+(III-11), (I-56)+(IV-1), (I-56)+(IV-2), (I-56)+(IV-3), (I-56)+(IV-4), (I-56)+(IV-5), (I-56)+(b-1), (I-56)+(b-2), (I-56)+(b-3), (I-56)+(b-4), (I-56)+(b-5), (I-56)+(b-6), (I-56)+(b-7), (I-56)+(b-8), (I-56)+(b-9), (I-56)+(b-10), (I-56)+(b-11), (I-56)+(b-12), (I-56)+(b-13), (I-56)+(b-14), (I-56)+(S3-1), (I-56)+(S3-2), (I-56)+(S3-3), (I-56)+(S3-4), (I-56)+(S3-

5), (I-56)+(h-1), (I-56)+(h-2), (I-56)+(V-1), (I-56)+(V-2), (I-56)+(V-3), (I-56)+(V-4), (I-56)+(V-5), (I-56)+(V-6).

(I-57)+(II-0), (I-57)+(II-1), (I-57)+(II-2), (I-57)+(II-3), (I-57)+(II-4), (I-57)+(II-5), (I-57)+(II-6), (I-57)+(II-9), (I-57)+(II-12), (I-57)+(III-1),-(I-57)+(III-4), (I-57)+(III-10), (I-57)+(III-11), (I-57)+(IV-1), (I-57)+(IV-2), (I-57)+(IV-3), (I-57)+(IV-4), (I-57)+(IV-5), (I-57)+(b-1), (I-57)+(b-2), (I-57)+(b-3), (I-57)+(b-4), (I-57)+(b-5), (I-57)+(b-6), (I-57)+(b-7), (I-57)+(b-8), (I-57)+(b-9), (I-57)+(b-10), (I-57)+(b-11), (I-57)+(b-12), (I-57)+(b-13), (I-57)+(b-14), (I-57)+(S3-1), (I-57)+(S3-2), (I-57)+(S3-3), (I-57)+(S3-4), (I-57)+(S3-5), (I-57)+(h-1), (I-57)+(h-2), (I-57)+(V-1), (I-57)+(V-2), (I-57)+(V-3), (I-57)+(V-4), (I-57)+(V-5), (I-57)+(V-6).

(I-58)+(II-0), (I-58)+(II-1), (I-58)+(II-2), (I-58)+(II-3), (I-58)+(II-4), (I-58)+(II-5), (I-58)+(II-6), (I-58)+(II-9), (I-58)+(II-12), (I-58)+(III-1), (I-58)+(III-4), (I-58)+(III-10), (I-58)+(III-11), (I-58)+(IV-1), (I-58)+(IV-2), (I-58)+(IV-3), (I-58)+(IV-4), (I-58)+(IV-5), (I-58)+(b-1), (I-58)+(b-2), (I-58)+(b-3), (I-58)+(b-4), (I-58)+(b-5), (I-58)+(b-6), (I-58)+(b-7), (I-58)+(b-8), (I-58)+(b-9), (I-58)+(b-10), (I-58)+(b-11), (I-58)+(b-12), (I-58)+(b-13), (I-58)+(b-14), (I-58)+(S3-1), (I-58)+(S3-2), (I-58)+(S3-3), (I-58)+(S3-4), (I-58)+(S3-5), (I-58)+(h-1), (I-58)+(h-2), (I-58)+(V-1), (I-58)+(V-2), (I-58)+(V-3), (I-58)+(V-4), (I-58)+(V-5), (I-58)+(V-6).

(I-59)+(II-0), (I-59)+(II-1), (I-59)+(II-2), (I-59)+(II-3), (I-59)+(II-4), (I-59)+(II-5), (I-59)+(II-6), (I-59)+(II-9), (I-59)+(II-12), (I-59)+(III-1), (I-59)+(III-4), (I-59)+(III-10), (I-59)+(III-11), (I-59)+(IV-1), (I-59)+(IV-2), (I-59)+(IV-3), (I-59)+(IV-4), (I-59)+(IV-5), (I-59)+(b-1), (IV-59)+(b-2), (I-59)+(b-3), (I-59)+(b-4), (I-59)+(b-5), (I-59)+(b-6), (I-59)+(b-7), (I-59)+(b-8), (I-59)+(b-9), (I-59)+(b-10), (I-59)+(b-11), (I-59)+(b-12), (I-59)+(b-13), (I-59)+(b-14), (I-59)+(S3-1), (I-59)+(S3-2), (I-59)+(S3-3), (I-59)+(S3-4), (I-59)+(S3-5), (I-59)+(h-1), (I-59)+(h-2), (I-59)+(V-1), (I-59)+(V-2), (I-59)+(V-3), (I-59)+(V-4), (I-59)+(V-5), (I-59)+(V-6).

(I-60)+(II-0), (I-60)+(II-1), (I-60)+(II-2), (I-60)+(II-3), (I-60)+(II-4), (I-60)+(II-5), (I-60)+(II-6), (I-60)+(II-9), (I-60)+(II-12), (I-60)+(III-1), (I-60)+(III-4), (I-60)+(III-10), (I-60)+(III-11), (I-60)+(IV-1), (I-60)+(IV-2), (I-60)+(IV-3), (I-60)+(IV-4), (I-60)+(IV-5), (I-60)+(b-1), (I-60)+(b-2), (I-60)+(b-3), (I-60)+(b-4), (I-60)+(b-5), (I-60)+(b-6), (I-60)+(b-7), (I-60)+(b-8), (I-60)+(b-9), (I-60)+(b-10), (I-60)+(b-11), (I-60)+(b-12), (I-60)+(b-13), (I-60)+(b-14), (I-60)+(S3-1), (I-60)+(S3-2), (I-60)+(S3-3), (I-60)+(S3-4), (I-60)+(S3-5), (I-60)+(h-1), (I-60)+(h-2), (I-60)+(V-1), (I-60)+(V-2), (I-60)+(V-3), (I-60)+(V-4), (I-60)+(V-5), (I-60)+(V-6).

(I-61)+(II-0), (I-61)+(II-1), (I-61)+(II-2), (I-61)+(II-3), (I-61)+(II-4), (I-61)+(II-5), (I-61)+(II-6), (I-61)+(II-9), (I-61)+(II-12), (I-61)+(III-1), (I-61)+(III-4), (I-61)+(III-10), (I-61)+(III-11), (I-61)+(IV-1), (I-61)+(IV-2), (I-61)+(IV-3), (I-61)+(IV-4), (I-61)+(IV-5), (I-61)+(b-1), (I-61)+(b-2), (I-61)+(b-3), (I-61)+(b-4), (I-61)+(b-5), (I-61)+(b-6), (I-61)+(b-7), (I-61)+(b-8), (I-61)+(b-9), (I-61)+(b-10), (I-61)+(b-11), (I-61)+(b-12), (I-61)+(b-13), (I-61)+(b-14), (I-61)+(S3-1), (I-61)+(S3-2), (I-61)+(S3-3), (I-61)+(S3-4), (I-61)+(S3-5), (I-61)+(h-1), (I-61)+(h-2), (I-61)+(V-1), (I-61)+(V-2), (I-61)+(V-3), (I-61)+(V-4), (I-61)+(V-5), (I-61)+(V-6).

(I-62)+(II-0), (I-62)+(II-1), (I-62)+(II-2), (I-62)+(II-3), (I-62)+(II-4), (I-62)+(II-5), (I-62)+(II-6), (I-62)+(II-9), (I-62)+(II-12), (I-62)+(III-1), (I-62)+(III-4), (I-62)+(III-10), (I-62)+(III-11), (I-62)+(IV-1), (I-62)+(IV-2), (I-62)+(IV-3), (I-62)+(IV-4), (I-62)+(IV-5), (I-62)+(b-1), (I-62)+(b-2), (I-62)+(b-3), (I-62)+(b-4), (I-62)+(b-5), (I-62)º(b-6), (I-62)+(b-7), (I-62)+(b-8), (I-62)+(b-9), (I-62)+(b-10), (I-62)+(b-11), (I-62)+(b-12), (I-62)+(b-13), (I-62)+(b-14), (I-62)+(S3-1), (I-62)+(S3-2), (I-62)+(S3-3), (I-62)+(S3-4), (I-62)+(S3-5), (I-62)+(h-1), (I-62)+(h-2), (I-62)+(V-1), (I-62)+(V-2), (I-62)+(V-3), (I-62)+(V-4), (I-62)+(V-5), (I-62)+(V-6).

(I-63)+(II-0), (I-63)+(II-1), (I-63)+(II-2), (I-63)+(II-3), (I-63)+(II-4), (I-63)+(II-5), (I-63)+(II-6), (I-63)+(II-9), (I-63)+(II-12), (I-63)+(III-1), (I-63)+(III-4), (I-63)+(III-10), (I-63)+(III-11), (I-63)+(IV-1), (I-63)+(IV-2), (I-63)+(IV-3), (I-63)+(IV-4), (I-63)+(IV-5), (I-63)+(b-1), (I-63)+(b-2), (I-63)+(b-3), (I-63)+(b-4), (I-63)+(b-5), (I-63)+(b-6), (I-63)+(b-7), (I-63)+(b-8), (I-63)+(b-9), (I-63)+(b-10), (I-63)+(b-11), (I-63)+(b-12), (I-63)+(b-13), (I-63)+(b-14), (I-63)+(S3-1), (I-63)+(S3-2), (I-63)+(S3-3), (I-63)+(S34), (I-63)+(S3-5), (I-63)+(h-1), (I-63)+(h-2), (I-63)+(V-1), (I-63)+(V-2), (I-63)+(V-3), (I-63)+(V-4), (I-63)+(V-5), (I-63)+(V-6).

(I-64)+(II-0), (I-64)+(II-1), (I-64)+(II-2), (I-64)+(II-3), (I-64)+(II-4), (I-64)+(II-5), (I-64)+(II-6), (I-64)+(II-9), (I-64)+(II-12), (I-64)+(III-1), (I-64)+(III-4), (I-64)+(III-10), (I-64)+(III-11), (I-64)+(IV-1), (I-64)+(IV-2), (I-64)+(IV-3), (I-64)+(IV-4), (I-64)+(IV-5), (I-64)+(b-1), (I-64)+(b-2), (I-64)+(b-3), (I-64)+(b-4), (I-64)+(b-5), (I-64)º(b-6), (I-64)+(b-7), (I-64)+(b-8), (I-64)+(b-9), (I-64)+(b-10), (I-64)+(b-11), (I-64)+(b-12), (I-64)+(b-13), (I-64)+(b-14), (I-64)+(S3-1), (I-64)+(S3-2), (I-64)+(S3-3), (I-64)+(S3-4), (I-64)+(S3-5), (I-64)+(h-1), (I-64)+(h-2), (I-64)+(V-1), (I-64)+(V-2), (I-64)+(V-3), (I-64)+(V-4), (I-64)+(V-5), (I-64)+(V-6).

(I-65)+(II-0), (I-65)+(II-1), (I-65)+(II-2), (I-65)+(II-3), (I-65)+(II-4), (I-65)+(II-5), (I-65)+(II-6), (I-65)+(II-9), (I-65)+(II-12), (I-65)+(III-1), (I-65)+(III-4), (I-65)+(III-10), (I-65)+(III-11), (I-65)+(IV-1), (I-65)+(IV-2), (I-65)+(IV-3), (I-65)+(IV-4), (I-65)+(IV-5), (I-65)+(b-1), (I-65)+(b-2), (I-65)+(b-3), (I-65)+(b-4), (I-65)+(b-5), (I-65)+(b-6), (I-65)+(b-7), (I-65)+(b-8), (I-65)+(b-9), (I-65)+(b-10), (I-65)+(b-11), (I-65)+(b-12), (I-65)+(b-13), (I-65)+(b-14), (I-65)+(S3-1), (I-65)+(S3-2), (I-65)+(S3-3), (I-65)+(S3-4), (I-65)+(S3-5), (I-65)+(h-1), (I-65)+(h-2), (I-65)+(V-1), (I-65)+(V-2), (I-65)+(V-3), (I-65)+(V-4), (I-65)+(V-5), (I-65)+(V-6).

(I-66)+(II-0), (I-66)+(II-1), (I-66)+(II-2), (I-66)+(II-3), (I-66)+(II-4), (I-66)+(II-5), (I-66)+(II-6), (I-66)+(II-9), (I-66)+(II-12), (I-66)+(III-1), (I-66)+(III-4), (I-66)+(III-10), (I-66)+(III-11), (I-66)+(IV-1), (I-66)+(IV-2), (I-66)+(IV-3), (I-66)+(IV-4), (I-66)+(IV-5), (I-66)+(b-1), (I-66)+(b-2), (I-66)+(b-3), (I-66)+(b-4), (I-66)+(b-5), (I-66)+(b-6), (I-66)+(b-7), (I-66)+(b-8), (I-66)+(b-9), (I-66)+(b-10), (I-66)+(b-11), (I-66)+(b-12), (I-66)+(b-13), (I-66)+(b-14), (I-66)+(S3-1), (I-66)+(S3-2), (I-66)+(S3-3), (I-66)+(S34), (I-66)+(S3-5), (I-66)+(h-1), (I-66)+(h-2), (I-66)+(V-1), (I-66)+(V-2), (I-66)+(V-3), (I-66)+(V-4), (I-66)+(V-5), (I-66)+(V-6).

(I-67)+(II-0), (I-67)+(II-1), (I-67)+(II-2), (I-67)+(II-3), (I-67)+(II-4), (I-67)+(II-5), (I-67)+(II-6), (I-67)+(II-9), (I-67)+(II-12), (I-67)+(III-1), (I-67)+(III-4), (I-67)+(III-10), (I-67)+(III-11), (I-67)+(IV-1), (I-67)+(IV-2), (I-67)+(IV-3), (I-67)+(IV-4), (I-67)+(IV-5), (I-67)+(b-1), (I-67)+(b-2), (I-67)+(b-3), (I-67)+(b-4), (I-67)+(b-5), (I-67)+(b-6), (I-67)+(b-7), (I-67)+(b-8), (I-67)+(b-9), (I-67)+(b-10), (I-67)+(b-11), (I-67)+(b-12), (I-67)+(b-13), (I-67)+(b-14), (I-67)+(S3-1), (I-67)+(S3-2), (I-67)+(S3-3), (I-67)+(S3-4), (I-67)+(S3-5), (I-67)+(h-1), (I-67)+(h-2), (I-67)+(V-1), (I-67)+(V-2), (I-67)+(V-3), (I-67)+(V-4), (I-67)+(V-5), (I-67)+(V-6).

(I-68)+(II-0), (I-68)+(II-1), (I-68)+(II-2), (I-68)+(II-3), (I-68)+(II-4), (I-68)+(II-5), (I-68)+(II-6), (I-68)+(II-9), (I-68)+(II-12), (I-68)+(III-1), (I-68)+(III-4), (I-68)+(III-10), (I-68)+(III-11), (I-68)+(IV-1), (I-68)+(IV-2), (I-68)+(IV-3), (I-68)+(IV-4), (I-68)+(IV-5), (I-68)+(b-1), (I-68)+(b-2), (I-68)+(b-3), (I-68)+(b-4), (I-68)+(b-5), (I-68)+(b-6), (I-68)+(b-7), (I-68)+(b-8), (I-68)+(b-9), (I-68)+(b-10), (I-68)+(b-11), (I-68)+(b-12), (I-68)+(b-13), (I-68)+(b-14), (I-68)+(S3-1), (I-68)+(S3-2), (I-68)+(S3-3), (I-68)+(S3-4), (I-68)+(S3-

5), (I-68)+(h-1), (I-68)+(h-2), (I-68)+(V-1), (I-68)+(V-2), (I-68)+(V-3), (I-68)+(V-4), (I-68)+(V-5), (I-68)+(V-6).

(I-69)+(II-0), (I-69)+(II-1), (I-69)+(II-2), (I-69)+(II-3), (I-69)+(II-4), (I-69)+(II-5), (I-69)+(II-6), (I-69)+(II-9), (I-69)+(II-12), (I-69)+(III-1), (I-69)+(III-4), (I-69)+(III-10), (I-69)+(III-11), (I-69)+(IV-1), (I-69)+(IV-2), (I-69)+(IV-3), (I-69)+(IV-4), (I-69)+(IV-5), (I-69)+(b-1), (I-69)+(b-2), (I-69)+(b-3), (I-69)+(b-4), (I-69)+(b-5), (I-69)+(b-6), (I-69)+(b-7), (I-69)+(b-8), (I-69)+(b-9), (I-69)+(b-10), (I-69)+(b-11), (I-69)+(b-12), (I-69)+(b-13), (I-69)+(b-14), (I-69)+(S3-1), (I-69)+(S3-2), (I-69)+(S3-3), (I-69)+(S3-4), (I-69)+(S3-5), (I-69)+(h-1), (I-69)+(h-2), (I-69)+(V-1), (I-69)+(V-2), (I-69)+(V-3), (I-69)+(V-4), (I-69)+(V-5), (I-69)+(V-6).

(I-70)+(II-0), (I-70)+(II-1), (I-70)+(II-2), (I-70)+(II-3), (I-70)+(II-4), (I-70)+(II-5), (I-70)+(II-6), (I-70)+(II-9), (I-70)+(II-12), (I-70)+(III-1), (I-70)+(III-4), (I-70)+(III-10), (I-70)+(III-11), (I-70)+(IV-1), (I-70)+(IV-2), (I-70)+(IV-3), (I-70)+(IV-4), (I-70)+(IV-5), (I-70)+(b-1), (I-70)+(b-2), (I-70)+(b-3), (I-70)+(b-4), (I-70)+(b-5), (I-70)+(b-6), (I-70)+(b-7), (I-70)+(b-8), (I-70)+(b-9), (I-70)+(b-10), (I-70)+(b-11), (I-70)+(b-12), (I-70)+(b-13), (I-70)+(b-14), (I-70)+(S3-1), (I-70)+(S3-2), (I-70)+(S3-3), (I-70)+(S3-4), (I-70)+(S3-5), (I-70)+(h-1), (I-70)+(h-2), (I-70)+(V-1), (I-70)+(V-2), (I-70)+(V-3), (I-70)+(V-4), (I-70)+(V-5), (I-70)+(V-6).

(I-71)+(II-0), (I-71)+(II-1), (I-71)+(II-2), (I-71)+(II-3), (I-71)+(II-4), (I-71)+(II-5), (I-71)+(II-6), (I-71)+(II-9), (I-71)+(II-12), (I-71)+(III-1), (I-71)+(III-4), (I-71)+(III-10), (I-71)+(III-11), (I-71)+(IV-1), (I-71)+(IV-2), (I-71)+(IV-3), (I-71)+(IV-4), (I-71)+(IV-5), (I-71)+(b-1), (I-71)+(b-2), (I-71)+(b-3), (I-71)+(b-4), (I-71)+(b-5), (I-71)+(b-6), (I-71)+(b-7), (I-71)+(b-8), (I-71)+(b-9), (I-71)+(b-10), (I-71)+(b-11), (I-71)+(b-12), (I-71)+(b-13), (I-71)+(b-14), (I-71)+(S3-1), (I-71)+(S3-2), (I-71)+(S3-3), (I-71)+(S3-4), (I-71)+(S3-5), (I-71)+(h-1), (I-71)+(h-2), (I-71)+(V-1), (I-71)+(V-2), (I-71)+(V-3), (I-71)+(V-4), (I-71)+(V-5), (I-71)+(V-6).

(I-72)+(II-0), (I-72)+(II-1), (I-72)+(II-2), (I-72)+(II-3), (I-72)+(II-4), (I-72)+(II-5), (I-72)+(II-6), (I-72)+(II-9), (I-72)+(II-12), (I-72)+(III-1), (I-72)+(III-4), (I-72)+(III-10), (I-72)+(III-11), (I-72)+(IV-1), (I-72)+(IV-2), (I-72)+(IV-3), (I-72)+(IV-4), (I-72)+(IV-5), (I-72)+(b-1), (I-72)+(b-2), (I-72)+(b-3), (I-72)+(b-4), (I-72)+(b-5), (I-72)+(b-6), (I-72)+(b-7), (I-72)+(b-8), (I-72)+(b-9), (I-72)+(b-10), (I-72)+(b-11), (I-72)+(b-12), (I-72)+(b-13), (I-72)+(b-14), (I-72)+(S3-1), (I-72)+(S3-2), (I-72)+(S3-3), (I-72)+(S3-4), (I-72)+(S3-5), (I-72)+(h-1), (I-72)+(h-2), (I-72)+(V-1), (I-72)+(V-2), (I-72)+(V-3), (I-72)+(V-4), (I-72)+(V-5), (I-72)+(V-6).

(I-73)+(II-0), (I-73)+(II-1), (I-73)+(II-2), (I-73)+(II-3), (I-73)+(I-4), (I-73)+(II-5), (I-73)+(II-6), (I-73)+(II-9), (I-73)+(II-12), (I-73)+(III-1), (I-73)+(III-4), (I-73)+(III-10), (I-73)+(III-11), (I-73)+(IV-1), (I-73)+(IV-2), (I-73)+(IV-3), (I-73)+(IV-4), (I-73)+(IV-5), (I-73)+(b-1), (I-73)+(b-2), (I-73)+(b-3), (I-73)+(b-4), (I-73)+(b-5), (I-73)+(b-6), (I-73)+(b-7), (I-73)+(b-8), (I-73)+(b-9), (I-73)+(b-10), (I-73)+(b-11), (I-73)+(b-12), (I-73)+(b-13), (I-73)+(b-14), (I-73)+(S3-1), (I-73)+(S3-2), (I-73)+(S3-3), (I-73)+(S3-4), (I-73)+(S3-5), (I-73)+(h-1), (I-73)+(h-2), (I-73)+(V-1), (I-73)+(V-2), (I-73)+(V-3), (I-73)+(V-4), (I-73)+(V-5), (I-73)+(V-6).

(I-74)+(II-0), (I-74)+(II-1), (I-74)+(II-2), (I-74)+(II-3), (I-74)+(II-4), (I-74)+(II-5), (I-74)+(II-6), (I-74)+(II-9), (I-74)+(II-12), (I-74)+(III-1), (I-74)+(III-4), (I-74)+(III-10), (I-74)+(III-11), (I-74)+(IV-1), (I-74)+(IV-2), (I-74)+(IV-3), (I-74)+(IV-4), (I-74)+(IV-5), (I-74)+(b-1), (I-74)+(b-2), (I-74)+(b-3), (I-74)+(b-4), (I-74)+(b-5), (I-74)+(b-6), (I-74)+(b-7), (I-74)+(b-8), (I-74)+(b-9), (I-74)+(b-10), (I-74)+(b-11), (I-74)+(b-12), (I-74)+(b-13), (I-74)+(b-14), (I-74)+(S3-1), (I-74)+(S3-2), (I-74)+(S3-3), (I-74)+(S3-4), (I-74)+(S3-5), (I-74)+(h-1), (I-74)+(h-2), (I-74)+(V-1), (I-74)+(V-2), (I-74)+(V-3), (I-74)+(V-4), (I-74)+(V-5), (I-74)+(V-6).

(I-75)+(II-0), (I-75)+(II-1), (I-75)+(II-2), (I-75)+(II-3), (I-75)+(II-4), (I-75)+(II-5), (I-75)+(II-6), (I-75)+(II-9), (I-75)+(II-12), (I-75)+(III-1), (I-75)+(III-4), (I-75)+(III-10), (I-75)+(III-11), (I-75)+(IV-1), (I-75)+(IV-2), (I-75)+(IV-3), (I-75)+(IV-4), (I-75)+(IV-5), (I-75)+(b-1), (I-75)+(b-2), (I-75)+(b-3), (I-75)+(b-4), (I-75)+(b-5), (I-75)+(b-6), (I-75)+(b-7), (I-75)+(b-8), (I-75)+(b-9), (I-75)+(b-10), (I-75)+(b-11), (I-75)+(b-12), (I-75)+(b-13), (I-75)+(b-14), (I-75)+(S3-1), (I-75)+(S3-2), (I-75)+(S3-3), (I-75)+(S3-4), (I-75)+(S3-5), (I-75)+(h-1), (I-75)+(h-2), (I-75)+(V-1), (I-75)+(V-2), (I-75)+(V-3), (I-75)+(V-4), (I-75)+(V-5), (I-75)+(V-6).

(I-76)+(II-0), (I-76)+(II-1), (I-76)+(II-2), (I-76)+(II-3), (I-76)+(II-4), (I-76)+(II-5), (I-76)+(II-6), (I-76)+(II-9), (I-76)+(II-12), (I-76)+(III-1), (I-76)+(III-4), (I-76)+(III-10), (I-76)+(III-11), (I-76)+(IV-1), (I-76)+(IV-2), (I-76)+(IV-3), (I-76)+(IV-4), (I-76)+(IV-5), (I-76)+(b-1), (I-76)+(b-2), (I-76)+(b-3), (I-76)+(b-4), (I-76)+(b-5), (I-76)+(b-6), (I-76)+(b-7), (I-76)+(b-8), (I-76)+(b-9), (I-76)+(b-10), (I-76)+(b-11), (I-76)+(b-12), (I-76)+(b-13), (I-76)+(b-14), (I-76)+(S3-1), (I-76)+(S3-2), (I-76)+(S3-3), (I-76)+(S3-4), (I-76)+(S3-5), (I-76)+(h-1), (I-76)+(h-2), (I-76)+(V-1), (I-76)+(V-2), (I-76)+(V-3), (I-76)+(V-4), (I-76)+(V-5), (I-76 )+(V-6).

(I-77)+(II-0), (I-77)+(II-1), (I-77)+(II-2), (I-77)+(II-3), (I-77)+(II-4), (I-77)+(II-5), (I-77)+(II-6), (I-77)+(II-9), (I-77)+(II-12), (I-77)+(III-1), (I-77)+(III-4), (I-77)+(III-10), (I-77)+(III-11), (I-77)+(IV-1), (I-77)+(IV-2), (I-77)+(IV-3), (I-77)+(IV-4), (I-77)+(IV-5), (I-77)+(b-1), (I-77)+(b-2), (I-77)+(b-3), (I-77)+(b-4), (I-77)+(b-5), (I-77)+(b-6), (I-77)+(b-7), (I-77)+(b-8), (I-77)+(b-9), (I-77)+(b-10), (I-77)+(b-11), (I-77)+(b-12), (I-77)+(b-13), (I-77)+(b-14), (I-77)+(S3-1), (I-77)+(S3-2), (I-77)+(S3-3), (I-77)+(S3-4), (I-77)+(S3-5), (I-77)+(h-1), (I-77)+(h-2), (I-77)+(V-1), (I-77)+(V-2), (I-77)+(V-3), (I-77)+(V-4), (I-77)+(V-5), (I-77)+(V-6).

(I-78)+(II-0), (I-78)+(II-1), (I-78)+(II-2), (I-78)+(II-3), (I-78)+(II-4), (I-78)+(II-5), (I-78)+(II-6), (I-78)+(II-9), (I-78)+(II-12), (I-78)+(III-1), (I-78)+(III-4), (I-78)+(III-10), (I-78)+(III-11), (I-78)+(IV-1), (I-78)+(IV-2), (I-78)+(IV-3), (I-78)+(IV-4), (I-78)+(IV-5), (I-78)+(b-1), (I-78)+(b-2), (I-78)+(b-3), (I-78)+(b-4), (I-78)+(b-5), (I-78)+(b-6), (I-78)+(b-7), (I-78)+(b-8), (I-78)+(b-9), (I-78)+(b-10), (I-78)+(b-11), (I-78)+(b-12), (I-78)+(b-13), (I-78)+(b-14), (I-78)+(S3-1), (I-78)+(S3-2), (I-78)+(S3-3), (I-78)+(S3-4), (I-78)+(S3-5), (I-78)+(h-1), (I-78)+(h-2), (I-78)+(V-1), (I-78)+(V-2), (I-78)+(V-3), (I-78)+(V-4), (I-78)+(V-5), (I-78 )+(V-6).

(I-79)+(II-0), (I-79)+(II-1), (I-79)+(II-2), (I-79)+(II-3), (I-79)+(II-4), (I-79)+(II-5), (I-79)+(II-6), (I-79)+(II-9), (I-79)+(II-12), (I-79)+(III-1), (I-79)+(III-4), (I-79)+(III-10), (I-79)+(III-11), (I-79)+(IV-1), (I-79)+(IV-2), (I-79)+(IV-3), (I-79)+(IV-4), (I-79)+(IV-5), (I-79)+(b-1), (I-79)+(b-2), (I-79)+(b-3), (I-79)+(b-4), (I-79)+(b-5), (I-79)+(b-6), (I-79)+(b-7), (I-79)+(b-8), (I-79)+(b-9), (I-79)+(b-10), (I-79)+(b-11), (I-79)+(b-12), (I-79)+(b-13), (I-79)+(b-14), (I-79)+(S3-1), (I-79)+(S3-2), (I-79)+(S3-3), (I-79)+(S3-4), (I-79)+(S3-5), (I-79)+(h-1), (I-79)+(h-2), (I-79)+(V-1), (I-79)+(V-2), (I-79)+(V-3), (I-79)+(V-4), (I-79)+(V-5), (I-79)+(V-6).

(I-80)+(II-0), (I-80)+(II-1), (I-80)+(II-2), (I-80)+(II-3), (I-80)+(II-4), (I-80)+(II-5), (I-80)+(II-6), (I-80)+(II-9), (I-80)+(II-12), (I-80)+(III-1), (I-80)+(III-4), (I-80)+(III-10), (I-80)+(III-11), (I-80)+(IV-1), (I-80)+(IV-2), (I-80)+(IV-3), (I-80)+(IV-4), (I-80)+(IV-5), (I-80)+(b-1), (I-80)+(b-2), (I-80)+(b-3), (I-80)+(b-4), (I-80)+(b-5), (I-80)+(b-6), (I-80 )+(b-7), (I-80)+(b-8), (I-80)+(b-9), (I-80)+(b-10), (I-80)+(b-11), (I-80)+(b-12), (I-80)+(b-13), (I-80)+(b-14), (I-80)+(S3-1), (I-80)+(S3-2), (I-80)+(S3-3), (I-80)+(S3-4), (I-80)+(S3-

5), (I-80)+(h-1), (I-80)+(h-2), (I-80)+(V-1), (I-80)+(V-2), (I-80)+(V-3), (I-80)+(V-4), (I-80)+(V-5), (I-80)+(V-6).

(I-81)+(II-0), (I-81)+(II-1), (I-81)+(II-2), (I-81)+(II-3), (I-80)+(II-4), (I-81)+(II-5), (I-81)+(II-6), (I-81)+(II-9), (I-81)+(II-12), (I-81)+(III-1), (I-81)+(III-4), (I-81)+(III-10), (I-81)+(III-11), (I-81)+(IV-1), (I-81)+(IV-2), (I-81)+(IV-3), (I-81)+(IV-4), (I-81)+(IV-5), (I-81)+(b-1), (I-81)+(b-2), (I-81)+(b-3), (I-81)+(b-4), (I-81)+(b-5), (I-81)+(b-6), (I-81)+(b-7), (I-81)+(b-8), (I-81)+(b-9), (I-81)+(b-10), (I-81)+(b-11), (I-81)+(b-12), (I-81)+(b-13), (I-81)+(b-14), (I-81)+(S3-1), (I-81)+(S3-2), (I-81)+(S3-3), (I-81)+(S3-4), (I-81)+(S3-5), (I-81)+(h-1), (I-81)+(h-2), (I-81)+(V-1), (I-81)+(V-2), (I-81)+(V-3), (I-81)+(V-4), (I-81)+(V-5), (I-81)+(V-6).

(I-82)+(II-0), (I-82)+(II-1), (I-82)+(II-2), (I-82)+(II-3), (I-82)+(II-4), (I-82)+(II-5), (I-82)+(II-6), (I-82)+(II-9), (I-82)+(II-12), (I-82)+(III-1), (I-82)+(III-4), (I-82)+(III-10), (I-82)+(III-11), (I-82)+(IV-1), (I-82)+(IV-2), (I-82)+(IV-3), (I-82)+(IV-4), (I-82)+(IV-5), (I-82)+(b-1), (I-82)+(b-2), (I-82)+(b-3), (I-82)+(b-4), (I-82)+(b-5), (I-82)+(b-6), (I-82)+(b-7), (I-82)+(b-8), (I-82)+(b-9), (I-82)+(b-10), (I-82)+(b-11), (I-82)+(b-12), (I-82)+(b-13), (I-82)+(b-14), (I-82)+(S3-1), (I-82)+(S3-2), (I-82)+(S3-3), (I-82)+(S3-4), (I-82)+(S3-5), (I-82)+(h-1), (I-82)+(h-2), (I-82)+(V-1), (I-82)+(V-2), (I-82)+(V-3), (I-82)+(V-4), (I-82)+(V-5), (I-82 )+(V-6).

(I-83)+(II-0), (I-83)+(II-1), (I-83)+(II-2), (I-83)+(II-3), (I-83)+(II-4), (I-83)+(II-5), (I-83)+(II-6), (I-83)+(II-9), (I-83)+(II-12), (I-83)+(III-1), (I-83)+(III-4), (I-83)+(III-10), (I-83)+(III-11), (I-83)+(IV-1), (I-83)+(IV-2), (I-83)+(IV-3), (I-83)+(IV-4), (I-83)+(IV-5), (I-83)+(b-1), (I-83)+(b-2), (I-83)+(b-3), (I-83)+(b-4), (I-83)+(b-5), (I-83)+(b-6), (I-83 )+(b-7), (I-83)+(b-8), (I-83)+(b-9), (I-83)+(b-10), (I-83)+(b-11), (I-83)+(b-12), (I-83)+(b-13), (I-83)+(b-14), (I-83)+(S3-1), (I-83)+(S3-2), (I-83)+(S3-3), (I-83)+(S3-4), (I-83)+(S3-5), (I-83)+(h-1), (I-83)+(h-2), (I-83)+(V-1), (I-83)+(V-2), (I-83)+(V-3), (I-83)+(V-4), (I-83)+(V-5), (I-83)+(V-6).

(I-84)+(II-0), (I-84)+(II-1), (I-84)+(II-2), (I-84)+(II-3), (I-84)+(II-4), (I-84)+(II-5), (I-84)+(II-6), (I-84)+(II-9), (I-84)+(II-12), (I-84)+(III-1), (I-84)+(III-4), (I-84)+(III-10), (I-84)+(III-11), (I-84)+(IV-1), (I-84)+(IV-2), (I-84)+(IV-3), (I-84)+(IV-4), (I-84)+(IV-5), (I-84)+(b-1), (I-84)+(b-2), (I-84)+(b-3), (I-84)+(b-4), (I-84)+(b-5), (I-84)+(b-6), (I-84)+(b-7), (I-84)+(b-8), (I-84)+(b-9), (I-84)+(b-10), (I-84)+(b-11), (I-84)+(b-12), (I-84)+(b-13), (I-84)+(b-14), (I-84)+(S3-1), (I-84)+(S3-2), (I-84)+(S3-3), (I-84)+(S3-4), (I-84)+(S3-5), (I-84)+(h-1), (I-84)+(h-2), (I-84)+(V-1), (I-84)+(V-2), (I-84)+(V-3), (I-84)+(V-4), (I-84)+(V-5), (I-84)+(V-6).

(I-85)+(II-0), (I-85)+(II-1), (I-85)+(II-2), (I-85)+(II-3), (I-85)+(II-4), (I-85)+(II-5), (I-85)+(II-6), (I-85)+(II-9), (I-85)+(II-12), (I-85)+(III-1), (I-85)+(III-4), (I-85)+(III-10), (I-85)+(III-11), (I-85)+(IV-1), (I-85)+(IV-2), (I-85)+(IV-3), (I-85)+(IV-4), (I-85)+(IV-5), (I-85)+(b-1), (I-85)+(b-2), (I-85)+(b-3), (I-85)+(b-4), (I-85)+(b-5), (I-85)+(b-6), (I-85)+(b-7), (I-85)+(b-8), (I-85)+(b-9), (I-85)+(b-10), (I-85)+(b-11), (I-85)+(b-12), (I-85)+(b-13), (I-85)+(b-14), (I-85)+(S3-1), (I-85)+(S3-2), (I-85)+(S3-3), (I-85)+(S3-4), (I-85)+(S3-5), (I-85)+(h-1), (I-85)+(h-2), (I-85)+(V-1), (I-85)+(V-2), (I-85)+(V-3), (I-85)+(V-4), (I-85)+(V-5), (I-85)+(V-6).

(I-86)+(II-0), (I-86)+(II-1), (I-86)+(II-2), (I-86)+(II-3), (I-86)+(II-4), (I-86)+(II-5), (I-86)+(II-6), (I-86)+(II-9), (I-86)+(II-12), (I-86)+(III-1), (I-86)+(III-4), (I-86)+(III-10), (I-86)+(III-11), (I-86)+(IV-1), (I-86)+(IV-2), (I-86)+(IV-3), (I-86)+(IV-4), (I-86)+(IV-5), (I-86)+(b-1), (I-86)+(b-2), (I-86)+(b-3), (I-86)+(b-4), (I-86)+(b-5), (I-86)+(b-6), (I-86)+(b-7), (I-86)+(b-8), (I-86)+(b-9), (I-86)+(b-10), (I-86)+(b-11), (I-86)+(b-12), (I-86)+(b-13), (I-86)+(b-14), (I-86)+(S3-1), (I-86)+(S3-2), (I-86)+(S3-3), (I-86)+(S3-4), (I-86)+(S3-5), (I-86)+(h-1), (I-86)+(h-2), (I-86)+(V-1), (I-86)+(V-2), (I-86)+(V-3), (I-86)+(V-4), (I-86)+(V-5), (I-86)+(V-6).

(I-87)+(II-0), (I-87)+(II-1), (I-87)+(II-2), (I-87)+(II-3), (I-87)+(II-4), (I-87)+(II-5), (I-87)+(II-6), (I-87)+(II-9), (I-87)+(II-12), (I-87)+(III-1), (I-87)+(III-4), (I-87)+(III-10), (I-87)+(III-11), (I-87)+(IV-1), (I-87)+(IV-2), (I-87)+(IV-3), (I-87)+(IV-4), (I-87)+(IV-5), (I-87)+(b-1), (I-87)+(b-2), (I-87)+(b-3), (I-87)+(b-4), (I-87)+(b-5), (I-87)+(b-6), (I-87)+(b-7), (I-87)+(b-8), (I-87)+(b-9), (I-87)+(b-10), (I-87)+(b-11), (I-87)+(b-12), (I-87)+(b-13), (I-87)+(b-14), (I-87)+(S3-1), (I-87)+(S3-2), (I-87)+(S3-3), (I-87)+(S3-4), (I-87)+(S3-5), (I-87)+(h-1), (I-87)+(h-2), (I-87)+(V-1), (I-87)+(V-2), (I-87)+(V-3), (I-87)+(V-4), (I-87)+(V-5), (I-87)+(V-6).

(I-88)+(II-0), (I-88)+(II-1), (I-88)+(II-2), (I-88)+(II-3), (I-88)+(II-4), (I-88)+(II-5), (I-88)+(II-6), (I-88)+(II-9), (I-88)+(II-12), (I-88)+(III-1), (I-88)+(III-4), (I-88)+(III-10), (I-88)+(III-11), (I-88)+(IV-1), (I-88)+(IV-2), (I-88)+(IV-3), (I-88)+(IV-4), (I-88)+(IV-5), (I-88)+(b-1), )I-88)+(b-2), (I-88)+(b-3), (I-88)+(b-4), (I-88)+(b-5), (I-88)+(b-6), (I-88)+(b-7), (I-88)+(b-8), (I-88)+(b-9), (I-88)+(b-10), (I-88)+(b-11), (I-88)+(b-12), (I-88)+(b-13), (I-88)+(b-14), (I-88)+(S3-1), (I-88)+(S3-2), (I-88)+(S3-3), (I-88)+(S3-4), (I-88)+(S3-5), (I-88)+(h-1), (I-88)+(h-2), (I-88)+(V-1), (I-88)+(V-2), (I-88)+(V-3), (I-88)+(V-4), (I-88)+(V-5), (I-88)+(V-6).

(I-89)+(II-0), (I-89)+(II-1), (I-89)+(II-2), (I-89)+(II-3), (I-89)+(II-4), (I-89)+(II-5), (I-89)+(II-6), (I-89)+(II-9), (I-89)+(II-12), (I-89)+(III-1), (I-89)+(III-4), (I-89)+(III-10), (I-89)+(III-11), (I-89)+(IV-1), (I-89)+(IV-2), (I-89)+(IV-3), (I-89)+(IV-4), (I-89)+(IV-5), (I-89)+(b-1), (I-89)+(b-2), (I-89)+(b-3), (I-89)+(b-4), (I-89)+(b-5), (I-89)+(b-6), (I-89)+(b-7), (I-89)+(b-8), (I-89)+(b-9), (I-89)+(b-10), (I-89)+(b-11), (I-89)+(b-12), (I-89)+(b-13), (I-89)+(b-14), (I-89)+(S3-1), (I-89)+(S3-2), (I-89)+(S3-3), (I-89)+(S3-4), (I-89)+(S3-5), (I-89)+(h-1), (I-89)+(h-2), (I-89)+(V-1), (I-89)+(V-2), (I-89)+(V-3), (I-89)+(V-4), (I-89)+(V-5), (I-89 )+(V-6).

(I-90)+(II-0), (I-90)+(II-1), (I-90)+(II-2), (I-90)+(II-3), (I-90)+(II-4), (I-90)+(II-5), (I-90)+(II-6), (I-90)+(II-9), (I-90)+(II-12), (I-90)+(III-1), (I-90)+(III-4), (I-90)+(III-10), (I-90)+(III-11), (I-90)+(IV-1), (I-90)+(IV-2), (I-90)+(IV-3), (I-90)+(IV-4), (I-90)+(IV-5), (I-90)+(b-1), (I-90)+(b-2), (I-90)+(b-3), (I-90)+(b-4), (I-90)+(b-5), (I-90)+(b-6), (I-90)+(b-7), (I-90)+(b-8), (I-90)+(b-9), (I-90)+(b-10), (I-90)+(b-11), (I-90)+(b-12), (I-90)+(b-13), (I-90)+(b-14), (I-90)+(S3-1), (I-90)+(S3-2), (I-90)+(S3-3), (I-90)+(S3-4), (I-90)+(S3-5), (I-90)+(h-1), (I-90)+(h-2), (I-90)+(V-1), (I-90)+(V-2), (I-90)+(V-3), (I-90)+(V-4), (I-90)+(V-5), (I-90)+(V-6).

(I-91)+(II-0), (I-91)+(II-1), (I-91)+(II-2), (I-91)+(II-3), (I-91)+(II-4), (I-91)+(II-5), (I-91)+(II-6), (I-91)+(II-9), (I-91)+(II-12), (I-91)+(III-1), (I-91)+(III-4), (I-91)+(III-10), (I-91)+(III-11), (I-91)+(IV-1), (I-91)+(IV-2), (I-91)+(IV-3), (I-91)+(IV-4), (I-91)+(IV-5), (I-91)+(b-1), (I-91)+(b-2), (I-91)+(b-3), (I-91)+(b-4), (I-91)+(b-5), (I-91)+(b-6), (I-91)+(b-7), (I-91)+(b-8), (I-91)+(b-9), (I-91)+(b-10), (I-91)+(b-11), (I-91)+(b-12), (I-91)+(b-13), (I-91)+(b-14), (I-91)+(S3-1), (I-91)+(S3-2), (I-91)+(S3-3), (I-91)+(S3-4), (I-91)+(S3-5), (I-91)+(h-1), (I-91)+(h-2), (I-91)+(V-1), (I-91)+(V-2), (I-91)+(V-3), (I-91)+(V-4), (I-91)+(V-5), (I-91)+(V-6).

(I-92)+(II-0), (I-92)+(II-1), (I-92)+(II-2), (I-92)+(II-3), (I-92)+(II-4), (I-92)+(II-5), (I-92)+(II-6), (I-92)+(II-9), (I-92)+(II-12), (I-92)+(III-1), (I-92)+(III-4), (I-92)+(III-10), (I-92)+(III-11), (I-92)+(IV-1), (I-92)+(IV-2), (I-92)+(IV-3), (I-92)+(IV-4), (I-92)+(IV-5), (I-92)+(b-1), (I-92)+(b-2), (I-92)+(b-3), (I-92)+(b-4), (I-92)+(b-5), (I-92)+(b-6), (I-92)+(b-7), (I-92)+(b-8), (I-92)+(b-9), (I-92)+(b-10), (I-92)+(b-11), (I-92)+(b-12), (I-92)+(b-13), (I-92)+(b-14), (I-92)+(S3-1), (I-92)+(S3-2), (I-92)+(S3-3), (I-92)+(S3-4), (I-92)+(S3-

5), (I-92)+(h-1), (I-92)+(h-2), (I-92)+(V-1), (I-92)+(V-2), (I-92)+(V-3), (I-92)+(V-4), (I-92)+(V-5), (I-92)+(V-6).

(I-93)+(II-0), (I-93)+(II-1), (I-93)+(II-2), (I-93)+(II-3), (I-93)+(II-4), (I-93)+(II-5), (I-93)+(II-6), (I-93)+(II-9), (I-93)+(II-12), (I-93)+(III-1), (I-93)+(III-4), (I-93)+(III-10), (I-93)+(III-11), (I-93)+(IV-1), (I-93)+(IV-2), (I-93)+(IV-3), (I-93)+(IV-4), (I-93)+(IV-5), (I-93)+(b-1), (I-93)+(b-2), (I-93)+(b-3), (I-93)+(b-4), (I-93)+(b-5), (I-93)+(b-6), (I-93)+(b-7), (I-93)+(b-8), (I-93)+(b-9), (I-93)+(b-10), (I-93)+(b-11), (I-93)+(b-12), (I-93)+(b-13), (I-93)+(b-14), (I-93)+(S3-1), (I-93)+(S3-2), (I-93)+(S3-3), (I-93)+(S3-4), (I-93)+(S3-5), (I-93)+(h-1), (I-93)+(h-2), (I-93)+(V-1), (I-93)+(V-2), (I-93)+(V-3), (I-93)+(V-4), (I-93)+(V-5), (I-93)+(V-6).

(I-94)+(II-0), (I-94)+(II-1), (I-94)+(II-2), (I-94)+(II-3), (I-94)+(II-4), (I-94)+(II-5), (I-94)+(II-6), (I-94)+(II-9), (I-94)+(II-12), (I-94)+(III-1), (I-94)+(III-4), (I-94)+(III-10), (I-94)+(III-11), (I-94)+(IV-1), (I-94)+(IV-2), (I-94)+(IV-3), (I-94)+(IV-4), (I-94)+(IV-5), (I-94)+(b-1), (I-94)+(b-2), (I-94)+(b-3), (I-94)+(b-4), (I-94)+(b-5), (I-94)+(b-6), (I-94)+(b-7), (I-94)+(b-8), (I-94)+(b-9), (I-94)+(b-10), (I-94)+(b-11), (I-94)+(b-12), (I-94)+(b-13), (I-94)+(b-14), (I-94)+(S3-1), (I-94)+(S3-2), (I-94)+(S3-3), (I-94)+(S3-4), (I-94)+(S3-5), (I-94)+(h-1), (I-94)+(h-2), (I-94)+(V-1), (I-94)+(V-2), (I-94)+(V-3), (I-94)+(V-4), (I-94)+(V-5), (I-94)+(V-6).

(I-95)+(II-0), (I-95)+(II-1), (I-95)+(II-2), (I-95)+(II-3), (I-95)+(II-4), (I-95)+(II-5), (I-95)+(II-6), (I-95)+(II-9), (I-95)+(II-12), (I-95)+(III-1), (I-95)+(III-4), (I-95)+(III-10), (I-95)+(III-11), (I-95)+(IV-1), (I-95)+(IV-2), (I-95)+(IV-3), (I-95)+(IV-4), (I-95)+(IV-5), (I-95)+(b-1), (I-95)+(b-2), (I-95)+(b-3), (I-95)+(b-4), (I-95)+(b-5), (I-95)+(b-6), (I-95)+(b-7), (I-95)+(b-8), (I-95)+(b-9), (I-95)+(b-10), (I-95)+(b-11), (I-95)+(b-12), (I-95)+(b-13), (I-95)+(b-14), (I-95)+(S3-1), (I-95)+(S3-2), (I-95)+(S3-3), (I-95)+(S3-4), (I-95)+(S3-5), (I-95)+(h-1), (I-95)+(h-2), (I-95)+(V-1), (I-95)+(V-2), (I-95)+(V-3), (I-95)+(V-4), (I-95)+(V-5), (I-95)+(V-6).

(I-96)+(II-0), (I-96)+(II-1), (I-96)+(II-2), (I-96)+(II-3), (I-96)+(II-4), (I-96)+(II-5), (I-96)+(II-6), (I-96)+(II-9), (I-96)+(II-12), (I-96)+(III-1), (I-96)+(III-4), (I-96)+(III-10), (I-96)+(III-11), (I-96)+(IV-1), (I-96)+(IV-2), (I-96)+(IV-3), (I-96)+(IV-4), (I-96)+(IV-5), (I-96)+(b-1), (I-96)+(b-2), (I-96)+(b-3), (I-96)+(b-4), (I-96)+(b-5), (I-96)+(b-6), (I-96)+(b-7), (I-96)+(b-8), (I-96)+(b-9), (I-96)+(b-10), (I-96)+(b-11), (I-96)+(b-12), (I-96)+(b-13), (I-96)+(b-14), (I-96)+(S3-1), (I-96)+(S3-2), (I-96)+(S3-3), (I-96)+(S3-4), (I-96)+(S3-5), (I-96)+(h-1), (I-96)+(h-2), (I-96)+(V-1), (I-96)+(V-2), (I-96)+(V-3), (I-96)+(V-4), (I-96)+(V-5), (I-96)+(V-6).

(I-97)+(II-0), (I-97)+(II-1), (I-97)+(II-2), (I-97)+(II-3), (I-97)+(II-4), (I-97)+(II-5), (I-97)+(II-6), (I-97)+(II-9), (I-97)+(II-12), (I-97)+(III-1), (I-97)+(III-4), (I-97)+(III-10), (I-97)+(III-11), (I-97)+(IV-1), (I-97)+(IV-2), (I-97)+(IV-3), (I-97)+(IV-4), (I-97)+(IV-5), (I-97)+(b-1), (I-97)+(b-2), (I-97)+(b-3), (I-97)+(b-4), (I-97)+(b-5), (I-97)+(b-6), (I-97)+(b-7), (I-97)+(b-8), (I-97)+(b-9), (I-97)+(b-10), (I-97)+(b-11), (I-97)+(b-12), (I-97)+(b-13), (I-97)+(b-14), (I-97)+(S3-1), (I-97)+(S3-2), (I-97)+(S3-3), (I-97)+(S3-4), (I-97)+(S3-5), (I-97)+(h-1), (I-97)+(h-2), (I-97)+(V-1), (I-97)+(V-2), (I-97)+(V-3), (I-97)+(V-4), (I-97)+(V-5), (I-97)+(V-6).

(I-98)+(II-0), (I-98)+(II-1), (I-98)+(II-2), (I-98)+(II-3), (I-98)+(II-4), (I-98)+(II-5), (I-98)+(II-6), (I-98)+(II-9), (I-98)+(II-12), (I-98)+(III-1), (I-98)+(III-4), (I-98)+(III-10), (I-98)+(III-11), (I-98)+(IV-1), (I-98)+(IV-2), (I-98)+(IV-3), (I-98)+(IV-4), (I-98)+(IV-5), (I-98)+(b-1), (I-98)+(b-2), (I-98)+(b-3), (I-98)+(b-4), (I-98)+(b-5), (I-98)+(b-6), (I-98)+(b-7), (I-98)+(b-8), (I-98)+(b-9), (I-98)+(b-10), (I-98)+(b-11), (I-98)+(b-12), (I-98)+(b-13), (I-98)+(b-14), (I-98)+(S3-1), (I-98)+(S3-2), (I-98)+(S3-3), (I-98)+(S3-4), (I-98)+(S3-5), (I-98)+(h-1), (I-98)+(h-2), (I-98)+(V-1), (I-98)+(V-2), (I-98)+(V-3), (I-98)+(V-4), (I-98)+(V-5), (I-98)+(V-6).

(I-99)+(II-0), (I-99)+(II-1), (I-99)+(II-2), (I-99)+(II-3), (I-99)+(II-4), (I-99)+(II-5), (I-99)+(II-6), (I-99)+(II-9), (I-99)+(II-12), (I-99)+(III-1), (I-99)+(III-4), (I-99)+(III-10), (I-99)+(III-11), (I-99)+(IV-1), (I-99)+(IV-2), (I-99)+(IV-3), (I-99)+(IV-4), (I-99)+(IV-5), (I-99)+(b-1), (I-99)+(b-2), (I-99)+(b-3), (I-99)+(b-4), (I-99)+(b-5), (I-99)+(b-6), (I-99)+(b-7), (I-99)+(b-8), (I-99)+(b-9), (I-99)+(b-10), (I-99)+(b-11), (I-99)+(b-12), (I-99)+(b-13), (I-99)+(b-14), (I-99)+(S3-1), (I-99)+(S3-2), (I-99)+(S3-3), (I-99)+(S3-4), (I-99)+(S3-5), (I-99)+(h-1), (I-99)+(h-2), (I-99)+(V-1), (I-99)+(V-2), (I-99)+(V-3), (I-99)+(V-4), (I-99)+(V-5), (I-99)+(V-6).

(I-100)+(II-0), (I-100)+(II-1), (I-100)+(II-2), (I-100)+(II-3), (I-100)+(II-4), (I-100)+(II-5), (I-100)+(II-6), (I-100)+(II-9), (I-100)+(II-12), (I-100)+(III-1), (I-100)+(III-4), (I-100)+(III-10), (I-100)+(III-11), (I-100)+(IV-1), (I-100)+(IV-2), (I-100)+(IV-3), (I-100)+(IV-4), (I-100)+(IV-5), (I-100)+(b-1), (I-100)+(b-2), (I-100)+(b-3), (I-100)+(b-4), (I-100)+(b-5), (I-100)+(b-6), (I-100)+(b-7), (I-100)+(b-8), (I-100)+(b-9), (I-100)+(b-10), (I-100)+(b-11), (I-100)+(b-12), (I-100)+(b-13), (I-100)+(b-14), (I-100)+(S3-1), (I-100)+(S3-2), (I-100)+(S3-3), (I-100)+(S3-4), (I-100)+(S3-5), (I-100)+(h-1), (I-100)+(h-2), (I-100)+(V-1), (I-100)+(V-2), (I-100)+(V-3), (I-100)+(V-4), (I-100)+(V-5), (I-100)+(V-6).

(I-101)+(II-0), (I-101)+(II-1), (I-101)+(II-2), (I-101)+(II-3), (I-101)+(II-4), (I-101)+(II-5), (I-101)+(II-6), (I-101)+(II-9), (I-101)+(II-12), (I-101)+(III-1), (I-101)+(III-4), (I-101)+(III-10), (I-101)+(III-11), (I-101)+(IV-1), (I-101)+(IV-2), (I-101)+(IV-3), (I-101)+(IV-4), (I-101)+(IV-5), (I-101)+(b-1), (I-101)+(b-2), (I-101)+(b-3), (I-101)+(b-4), (I-101)+(b-5), (I-101)+(b-6), (I-101)+(b-7), (I-101)+(b-8), (I-101)+(b-9), (I-101)+(b-10), (I-101)+(b-11), (I-101)+(b-12), (I-101)+(b-13), (I-101)+(b-14), (I-101)+(S3-1), (I-101)+(S3-2), (I-101)+(S3-3), (I-101)+(S3-4), (I-101)+(S3-5), (I-101)+(h-1), (I-101)+(h-2), (I-101)+(V-1), (I-101)+(V-2), (I-101)+(V-3), (I-101)+(V-4), (I-101)+(V-5), (I-101)+(V-6).

(I-102)+(II-0), (I-102)+(II-1), (I-102)+(II-2), (I-102)+(II-3), (I-102)+(II-4), (I-102)+(II-5), (I-102)+(II-6), (I-102)+(II-9), (I-102)+(II-12), (I-102)+(III-1), (I-102)+(III-4), (I-102)+(III-10), (I-102)+(III-11), (I-102)+(IV-1), (I-102)+(IV-2), (I-102)+(IV-3), (I-102)+(IV-4), (I-102)+(IV-5), (I-102)+(b-1), (I-102)+(b-2), (I-102)+(b-3), (I-102)+(b-4), (I-102)+(b-5), (I-102)+(b-6), (I-102)+(b-7), (I-102)+(b-8), (I-102)+(b-9), (I-102)+(b-10), (I-102)+(b-11), (I-102)+(b-12), (I-102)+(b-13), (I-102)+(b-14), (I-102)+(S3-1), (I-102)+(S3-2), (I-102)+(S3-3), (I-102)+(S3-4), (I-102)+(S3-5), (I-102)+(h-1), (I-102)+(h-2), (I-102)+(V-1), (I-102)+(V-2), (I-102)+(V-3), (I-102)+(V-4), (I-102)+(V-5), (I-102)+(V-6).

(I-103)+(II-0), (I-103)+(II-1), (I-103)+(II-2), (I-103)+(II-3), (I-103)+(II-4), (I-103)+(II-5), (I-103)+(II-6), (I-103)+(II-9), (I-103)+(II-12), (I-103)+(III-1), (I-103)+(III-4), (I-103)+(III-10), (I-103)+(III-11), (I-103)+(IV-1), (I-103)+(IV-2), (I-103)+(IV-3), (I-103)+(IV-4), (I-103)+(IV-5), (I-103)+(b-1), (I-103)+(b-2), (I-103)+(b-3), (I-103)+(b-4), (I-103)+(b-5), (I-103)+(b-6), (I-103)+(b-7), (I-103)+(b-8), (I-103)+(b-9), (I-103)+(b-10), (I-103)+(b-11), (I-103)+(b-12), (I-103)+(b-13), (I-103)+(b-14), (I-103)+(S3-1), (I-103)+(S3-2), (I-103)+(S3-3), (I-103)+(S3-4), (I-103)+(S3-5), (I-103)+(h-1), (I-103)+(h-2), (I-103)+(V-1), (I-103)+(V-2), (I-103)+(V-3), (I-103)+(V-4), (I-103)+(V-5), (I-103)+(V-6).

(I-104)+(II-0), (I-104)+(II-1), (I-104)+(II-2), (I-104)+(II-3), (I-104)+(II-4), (I-104)+(II-5), (I-104)+(II-6), (I-104)+(II-9), (I-104)+(II-12), (I-104)+(III-1), (I-104)+(III-4), (I-104)+(III-10), (I-104)+(III-11), (I-104)+(IV-1), (I-104)+(IV-2), (I-104)+(IV-3), (I-104)+(IV-4), (I-104))+(IV-5), (I-104)+(b-1), (I-104)+(b-2), (I-104)+(b-3), (I-104)+(b-4), (I-104)+(b-

5), (I-104)+(b-6), (I-104)+(b-7), (I-104)+(b-8), (I-104)+(b-9), (I-104)+(b-10), (I-104)+(b-11), (I-104)+(b-12), (I-104)+(b-13), (I-104)+(b-14), (I-104)+(S3-1), (I-104)+(S3-2), (I-104)+(S3-3), (I-104)+(S3-4), (I-104)+(S3-5), (I-104)+(h-1), (I-104)+(h-2), (I-104)+(V-1), (I-104)+(V-2), (I-104)+(V-3), (I-104)+(V-4), (I-104)+(V-5), (I-104)+(V-6).

(I-105)+(II-0), (I-105)+(II-1), (I-105)+(II-2), (I-105)+(II-3), (I-105)+(II-4), (I-105)+(II-5), (I-105)+(II-6), (I-105)+(II-9), (I-105)+(II-12), (I-105)+(III-1), (I-105)+(III-4), (I-105)+(III-10), (I-105)+(III-11), (I-105)+(IV-1), (I-105)+(IV-2), (I-105)+(IV-3), (I-105)+(IV-4), (I-105)+(IV-5), (I-105)+(b-1), (I-105)+(b-2), (I-105)+(b-3), (I-105)+(b-4), (I-105)+(b-5), (I-105)+(b-6), (I-105)+(b-7), (I-105)+(b-8), (I-105)+(b-9), (I-105)+(b-10), (I-105)+(b-11), (I-105)+(b-12), (I-105)+(b-13), (I-105)+(b-14), (I-105)+(S3-1), (I-105)+(S3-2), (I-105)+(S3-3), (I-105)+(S3-4), (I-105)+(S3-5), (I-105)+(h-1), (I-105)+(h-2), (I-105)+(V-1), (I-105)+(V-2), (I-105)+(V-3), (I-105)+(V-4), (I-105)+(V-5), (I-105)+(V-6).

(I-106)+(II-0), (I-106)+(II-1), (I-106)+(II-2), (I-106)+(II-3), (I-106)+(II-4), (I-106)+(II-5), (I-106)+(II-6), (I-106)+(II-9), (I-106)+(II-12), (I-106)+(III-1), (I-106)+(III-4), (I-106)+(III-10), (I-106)+(III-11), (I-106)+(IV-1), (I-106)+(IV-2), (I-106)+(IV-3), (I-106)+(IV-4), (I-106)+(IV-5), (I-106)+(b-1), (I-106)+(b-2), (I-106)+(b-3), (I-106)+(b-4), (I-106)+(b-5), (I-106)+(b-6), (I-106)+(b-7), (I-106)+(b-8), (I-106)+(b-9), (I-106)+(b-10), (I-106)+(b-11), (I-106)+(b-12), (I-106)+(b-13), (I-106)+(b-14), (I-106)+(S3-1), (I-106)+(S3-2), (I-106)+(S3-3), (I-106)+(S3-4), (I-106)+(S3-5), (I-106)+(h-1), (I-106)+(h-2), (I-106)+(V-1), (I-106)+(V-2), (I-106)+(V-3), (I-106)+(V-4), (I-106)+(V-5), (I-106)+(V-6).

(I-107)+(II-0), (I-107)+(II-1), (I-107)+(II-2), (I-107)+(II-3), (I-107)+(II-4), (I-107)+(II-5), (I-107)+(II-6), (I-107)+(II-9), (I-107)+(II-12), (I-107)+(III-1), (I-107)+(III-4), (I-107)+(III-10), (I-107)+(III-11), (I-107)+(IV-1), (I-107)+(IV-2), (I-107)+(IV-3), (I-107)+(IV-4), (I-107)+(IV-5), (I-107)+(b-1), (I-107)+(b-2), (I-107)+(b-3), (I-107)+(b-4), (I-107)+(b-5), (I-107)+(b-6), (I-107)+(b-7), (I-107)+(b-8), (I-107)+(b-9), (I-107)+(b-10), (I-107)+(b-11), (I-107)+(b-12), (I-107)+(b-13), (I-107)+(b-14), (I-107)+(S3-1), (I-107)+(S3-2), (I-107)+(S3-3), (I-107)+(S3-4), (I-107)+(S3-5), (I-107)+(h-1), (I-107)+(h-2), (I-107)+(V-1), (I-107)+(V-2), (I-107)+(V-3), (I-107)+(V-4), (I-107)+(V-5), (I-107)+(V-6).

(I-108)+(II-0), (I-108)+(II-1), (I-108)+(II-2), (I-108)+(II-3), (I-108)+(II-4), (I-108)+(II-5), (I-108)+(II-6), (I-108)+(II-9), (I-108)+(II-12), (I-108)+(III-1), (I-108)+(III-4), (I-108)+(III-10), (I-108)+(III-11), (I-108)+(IV-1), (I-108)+(IV-2), (I-108)+(IV-3), (I-108)+(IV-4), (I-108)+(IV-5), (I-108)+(b-1), (I-108)+(b-2), (I-108)+(b-3), (I-108)+(b-4), (I-108)+(b-5), (I-108)+(b-6), (I-108)+(b-7), (I-108)+(b-8), (I-108)+(b-9), (I-108)+(b-10), (I-108)+(b-11), (I-108)+(b-12), (I-108)+(b-13), (I-108)+(b-14), (I-108)+(S3-1), (I-108)+(S3-2), (I-108)+(S3-3), (I-108)+(S3-4), (I-108)+(S3-5), (I-108)+(h-1), (I-108)+(h-2), (I-108)+(V-1), (I-108)+(V-2), (I-108)+(V-3), (I-108)+(V-4), (I-108)+(V-5), (I-108)+(V-6).

(I-109)+(II-0), (I-109)+(II-1), (I-109)+(II-2), (I-109)+(II-3), (I-109)+(II-4), (I-109)+(II-5), (I-109)+(II-6), (I-109)+(II-9), (I-109)+(II-12), (I-109)+(III-1), (I-109)+(III-4), (I-109)+(III-10), (I-109)+(III-11), (I-109)+(IV-1), (I-109)+(IV-2), (I-109)+(IV-3), (I-109)+(IV-4), (I-109)+(IV-5), (I-109)+(b-1), (I-109)+(b-2), (I-109)+(b-3), (I-109)+(b-4), (I-109)+(b-5), (I-109)+(b-6), (I-109)+(b-7), (I-109)+(b-8), (I-109)+(b-9), (I-109)+(b-10), (I-109)+(b-11), (I-109)+(b-12), (I-109)+(b-13), (I-109)+(b-14), (I-109)+(S3-1), (I-109)+(S3-2), (I-109)+(S3-3), (I-109)+(S3-4), (I-109)+(S3-5), (I-109)+(h-1), (I-109)+(h-2), (I-109)+(V-1), (I-109)+(V-2), (I-109)+(V-3), (I-109)+(V-4), (I-109)+(V-5), (I-109)+(V-6).

(I-110)+(II-0), (I-110)+(II-1), (I-110)+(II-2), (I-110)+(II-3), (I-110)+(II-4), (I-110)+(II-5), (I-110)+(II-6), (I-110)+(II-9), (I-110)+(II-12), (I-110)+(III-1), (I-110)+(III-4), (I-110)+(III-10), (I-110)+(III-11), (I-110)+(IV-1), (I-110)+(IV-2), (I-110)+(IV-3), (I-110)+(IV-4), (I-110)+(IV-5), (I-110)+(b-1), (I-110)+(b-2), (I-110)+(b-3), (I-110)+(b-4), (I-110)+(b-5), (I-110)+(b-6), (I-110)+(b-7), (I-110)+(b-8), (I-110)+(b-9), (I-110)+(b-10), (I-110)+(b-11), (I-110)+(b-12), (I-110)+(b-13), (I-110)+(b-14), (I-110)+(S3-1), (I-110)+(S3-2), (I-110)+(S3-3), (I-110)+(S3-4), (I-110)+(S3-5), (I-110)+(h-1), (I-110)+(h-2), (I-110)+(V-1), (I-110)+(V-2), (I-110)+(V-3), (I-110)+(V-4), (I-110)+(V-5), (I-110)+(V-6).

(I-111)+(II-0), (I-111)+(II-1), (I-111)+(II-2), (I-111)+(II-3), (I-111)+(II-4), (I-111)+(II-5), (I-111)+(II-6), (I-111)+(II-9), (I-111)+(II-12), (I-111)+(III-1), (I-111)+(III-4), (I-111)+(III-10), (I-111)+(III-11), (I-111)+(IV-1), (I-111)+(IV-2), (I-111)+(IV-3), (I-111)+(IV-4), (I-111)+(IV-5), (I-111)+(b-1), (I-111)+(b-2), (I-111)+(b-3), (I-111)+(b-4), (I-111)+(b-5), (I-111)+(b-6), (I-111)+(b-7), (I-111)+(b-8), (I-111)+(b-9), (I-111)+(b-10), (I-111)+(b-11), (I-111)+(b-12), (I-111)+(b-13), (I-111)+(b-14), (I-111)+(S3-1), (I-111)+(S3-2), (I-111)+(S3-3), (I-111)+(S3-4), (I-111)+(S3-5), (I-111)+(h-1), (I-111)+(h-2), (I-111)+(V-1), (I-111)+(V-2), (I-111)+(V-3), (I-111)+(V-4), (I-111)+(V-5), (I-111)+(V-6).

(I-112)+(II-0), (I-112)+(II-1), (I-112)+(II-2), (I-112)+(II-3), (I-112)+(II-4), (I-112)+(II-5), (I-112)+(II-6), (I-112)+(II-9), (I-112)+(II-12), (I-112)+(III-1), (I-112)+(III-4), (I-112)+(III-10), (I-112)+(III-11), (I-112)+(IV-1), (I-112)+(IV-2), (I-112)+(IV-3), (I-112)+(IV-4), (I-112)+(IV-5), (I-112)+(b-1), (I-112)+(b-2), (I-112)+(b-3), (I-112)+(b-4), (I-112)+(b-5), (I-112)+(b-6), (I-112)+(b-7), (I-112)+(b-8), (I-112)+(b-9), (I-112)+(b-10), (I-112)+(b-11), (I-112)+(b-12), (I-112)+(b-13), (I-112)+(b-14), (I-112)+(S3-1), (I-112)+(S3-2), (I-112)+(S3-3), (I-112)+(S3-4), (I-112)+(S3-5), (I-112)+(h-1), (I-112)+(h-2), (I-112)+(V-1), (I-112)+(V-2), (I-112)+(V-3), (I-112)+(V-4), (I-112)+(V-5), (I-112)+(V-6).

(I-113)+(II-0), (I-113)+(II-1), (I-113)+(II-2), (I-113)+(II-3), (I-113)+(II-4), (I-113)+(II-5), (I-113)+(II-6), (I-113)+(II-9), (I-113)+(II-12), (I-113)+(III-1), (I-113)+(III-4), (I-113)+(III-10), (I-113)+(III-11), (I-113)+(IV-1), (I-113)+(IV-2), (I-113)+(IV-3), (I-113)+(IV-4), (I-113)+(IV-5), (I-113)+(b-1), (I-113)+(b-2), (I-113)+(b-3), (I-113)+(b-4), (I-113)+(b-5), (I-113)+(b-6), (I-113)+(b-7), (I-113)+(b-8), (I-113)+(b-9), (I-113)+(b-10), (I-113)+(b-11), (I-113)+(b-12), (I-113)+(b-13), (I-113)+(b-14), (I-113)+(S3-1), (I-113)+(S3-2), (I-113)+(S3-3), (I-113)+(S3-4), (I-113)+(S3-5), (I-113)+(h-1), (I-113)+(h-2), (I-113)+(V-1), (I-113)+(V-2), (I-113)+(V-3), (I-113)+(V-4), (I-113)+(V-5), (I-113)+(V-6).

(I-114)+(II-0), (I-114)+(II-1), (I-114)+(II-2), (I-114)+(II-3), (I-114)+(II-4), (I-114)+(II-5), (I-114)+(II-6), (I-114)+(II-9), (I-114)+(II-12), (I-114)+(III-1), (I-114)+(III-4), (I-114)+(III-10), (I-114)+(III-11), (I-114)+(IV-1), (I-114)+(IV-2), (I-114)+(IV-3), (I-114)+(IV-4), (I-114)+(IV-5), (I-114)+(b-1), (I-114)+(b-2), (I-114)+(b-3), (I-114)+(b-4), (I-114)+(b-5), (I-114)+(b-6), (I-114)+(b-7), (I-114)+(b-8), (I-114)+(b-9), (I-114)+(b-10), (I-114)+(b-11), (I-114)+(b-12), (I-114)+(b-13), (I-114)+(b-14), (I-114)+(S3-1), (I-114)+(S3-2), (I-114)+(S3-3), (I-114)+(S3-4), (I-114)+(S3-5), (I-114)+(h-1), (I-114)+(h-2), (I-114)+(V-1), (I-114)+(V-2), (I-114)+(V-3), (I-114)+(V-4), (I-114)+(V-5), (I-114)+(V-6).

(I-115)+(II-0), (I-115)+(II-1), (I-115)+(II-2), (I-115)+(II-3), (I-115)+(II-4), (I-115)+(II-5), (I-115)+(II-6), (I-115)+(II-9), (I-115)+(II-12), (I-115)+(III-1), (I-115)+(III-4), (I-115)+(III-10), (I-115)+(III-11), (I-115)+(IV-1), (I-115)+(IV-2), (I-115)+(IV-3), (I-115)+(IV-4), (I-115)+(IV-5), (I-115)+(b-1), (I-115)+(b-2), (I-115)+(b-3), (I-115)+(b-4), (I-115)+(b-5), (I-115)+(b-6), (I-115)+(b-7), (I-115)+(b-8), (I-115)+(b-

9), (I-115)+(b-10), (I-115)+(b-11), (I-115)+(b-12), (I-115)+(b-13), (I-115)+(b-14), (I-115)+(S3-1), (I-115)+(S3-2), (I-115)+(S3-3), (I-115)+(S3-4), (I-115)+(S3-5), (I-115)+(h-1), (I-115)+(h-2), (I-115)+(V-1), (I-115)+(V-2), (I-115)+(V-3), (I-115)+(V-4), (I-115)+(V-5), (I-115)+(V-6).

(I-116)+(II-0), (I-116)+(II-1), (I-116)+(II-2), (I-116)+(II-3), (I-116)+(II-4), (I-116)+(II-5), (I-116)+(II-6), (I-116)+(II-9), (I-116)+(II-12), (I-116)+(III-1), (I-116)+(III-4), (I-116)+(III-10), (I-116)+(III-11), (I-116)+(IV-1), (I-116)+(IV-2), (I-116)+(IV-3), (I-116)+(IV-4), (I-116)+(IV-5), (I-116)+(b-1), (I-116)+(b-2), (I-116)+(b-3), (I-116)+(b-4), (I-116)+(b-5), (I-116)+(b-6), (I-116)+(b-7), (I-116)+(b-8), (I-116)+(b-9), (I-116)+(b-10), (I-116)+(b-11), (I-116)+(b-12), (I-116)+(b-13), (I-116)+(b-14), (I-116)+(S3-1), (I-116)+(S3-2), (I-116)+(S3-3), (I-116)+(S3-3), (I-116)+(S3-5), (I-116)+(h-1), (I-116)+(h-2), (I-116)+(V-1), (I-116)+(V-2), (I-116)+(V-3), (I-116)+(V-4), (I-116)+(V-5), (I-116)+(V-6).

(I-117)+(II-0), (I-117)+(II-1), (I-117)+(II-2), (I-117)+(II-3), (I-117)+(II-4), (I-117)+(II-5), (I-117)+(II-6), (I-117)+(II-9), (I-117)+(II-12), (I-117)+(III-1), (I-117)+(III-4), (I-117)+(III-10), (I-117)+(III-11), (I-117)+(IV-1), (I-117)+(IV-2), (I-117)+(IV-3), (I-117)+(IV-4), (I-117)+(IV-5), (I-117)+(b-1), (I-117)+(b-2), (I-117)+(b-3), (I-117)+(b-4), (I-117)+(b-5), (I-117)+(b-6), (I-117)+(b-7), (I-117)+(b-8), (I-117)+(b-9), (I-117)+(b-10), (I-117)+(b-11), (I-117)+(b-12), (I-117)+(b-13), (I-117)+(b-14), (I-117)+(S3-1), (I-117)+(S3-2), (I-117)+(S3-3), (I-117)+(S3-4), (I-117)+(S3-5), (I-117)+(h-1), (I-117)+(h-2), (I-117)+(V-1), (I-117)+(V-2), (I-117)+(V-3), (I-117)+(V-4), (I-117)+(V-5), (I-117)+(V-6).

(I-118)+(II-0), (I-118)+(II-1), (I-118)+(II-2), (I-118)+(II-3), (I-118)+(II-4), (I-118)+(II-5), (I-118)+(II-6), (I-118)+(II-9), (I-118)+(II-12), (I-118)+(III-1), (I-118)+(III-4), (I-118)+(III-10), (I-118)+(III-11), (I-118)+(IV-1), (I-118)+(IV-2), (I-118)+(IV-3), (I-118)+(IV-4), (I-118)+(IV-5), (I-118)+(b-1), (I-118)+(b-2), (I-118)+(b-3), (I-118)+(b-4), (I-118)+(b-5), (I-118)+(b-6), (I-118)+(b-7), (I-118)+(b-8), (I-118)+(b-9), (I-118)+(b-10), (I-118)+(b-11), (I-118)+(b-12), (I-118)+(b-13), (I-118)+(b-14), (I-118)+(S3-1), (I-118)+(S3-2), (I-118)+(S3-3), (I-118)+(S3-4), (I-118)+(S3-5), (I-118)+(h-1), (I-118)+(h-2), (I-118)+(V-1), (I-118)+(V-2), (I-118)+(V-3), (I-118)+(V-4), (I-118)+(V-5), (I-118)+(V-6).

(I-119)+(II-0), (I-119)+(II-1), (I-119)+(II-2), (I-119)+(II-3), (I-119)+(II-4), (I-119)+(II-5), (I-119)+(II-6), (I-119)+(II-9), (I-119)+(II-12), (I-119)+(III-1), (I-119)+(III-4), (I-119)+(III-10), (I-119)+(III-11), (I-119)+(IV-1), (I-119)+(IV-2), (I-119)+(IV-3), (I-119)+(IV-4), (I-119)+(IV-5), (I-119)+(b-1), (I-119)+(b-2), (I-119)+(b-3), (I-119)+(b-4), (I-119)+(b-5), (I-119)+(b-6), (I-119)+(b-7), (I-119)+(b-8), (I-119)+(b-9), (I-119)+(b-10), (I-119)+(b-11), (I-119)+(b-12), (I-119)+(b-13), (I-119)+(b-14), (I-119)+(S3-1), (I-119)+(S3-2), (I-119)+(S3-3), (I-119)+(S3-4), (I-119)+(S3-5), (I-119)+(h-1), (I-119)+(h-2), (I-119)+(V-1), (I-119)+(V-2), (I-119)+(V-3), (I-119)+(V-4), (I-119)+(V-5), (I-119)+(V-6).

(I-120)+(II-0), (I-120)+(II-1), (I-120)+(II-2), (I-120)+(II-3), (I-120)+(II-4), (I-120)+(II-5), (I-120)+(II-6), (I-120)+(II-9), (I-120)+(II-12), (I-120)+(III-1), (I-120)+(III-4), (I-120)+(III-10), (I-120)+(III-11), (I-120)+(IV-1), (I-120)+(IV-2), (I-120)+(IV-3), (I-120)+(IV-4), (I-120)+(IV-5), (I-120)+(b-1), (I-120)+(b-2), (I-120)+(b-3), (I-120)+(b-4), (I-120)+(b-5), (I-120)+(b-6), (I-120)+(b-7), (I-120)+(b-8), (I-120)+(b-9), (I-120)+(b-10), (I-120)+(b-11), (I-120)+(b-12), (I-120)+(b-13), (I-120)+(b-14), (I-120)+(S3-1), (I-120)+(S3-2), (I-120)+(S3-3), (I-120)+(S3-4), (I-120)+(S3-5), (I-120)+(h-1), (I-120)+(h-2), (I-120)+(V-1), (I-120)+(V-2), (I-120)+(V-3), (I-120)+(V-4), (I-120)+(V-5), (I-120)+(V-6).

(I-121)+(II-0), (I-121)+(II-1), (I-121)+(II-2), (I-121)+(II-3), (I-121)+(II-4), (I-121)+(II-5), (I-121)+(II-6), (I-121)+(II-9), (I-121)+(II-12), (I-121)+(III-1), (I-121)+(III-4), (I-121)+(III-10), (I-121)+(III-11), (I-121)+(IV-1), (I-121)+(IV-2), (I-121)+(IV-3), (I-121)+(IV-4), (I-121)+(IV-5), (I-121)+(b-1), (I-121)+(b-2), (I-121)+(b-3), (I-121)+(b-4), (I-121)+(b-5), (I-121)+(b-6), (I-121)+(b-7), (I-121)+(b-8), (I-121)+(b-9), (I-121)+(b-10), (I-121)+(b-11), (I-121)+(b-12), (I-121)+(b-13), (I-121)+(b-14), (I-121)+(S3-1), (I-121)+(S3-2), (I-121)+(S3-3), (I-121)+(S3-4), (I-121)+(S3-5), (I-121)+(h-1), (I-121)+(h-2), (I-121)+(V-1), (I-121)+(V-2), (I-121)+(V-3), (I-121)+(V-4), (I-121)+(V-5), (I-121)+(V-6).

(I-122)+(II-0), (I-122)+(II-1), (I-122)+(II-2), (I-122)+(II-3), (I-122)+(II-4), (I-122)+(II-5), (I-122)+(II-6), (I-122)+(II-9), (I-122)+(II-12), (I-122)+(III-1), (I-122)+(III-4), (I-122)+(III-10), (I-122)+(III-11), (I-122)+(IV-1), (I-122)+(IV-2), (I-122)+(IV-3), (I-122)+(IV-4), (I-122)+(IV-5), (I-122)+(b-1), (I-122)+(b-2), (I-122)+(b-3), (I-122)+(b-4), (I-122)+(b-5), (I-122)+(b-6), (I-122)+(b-7), (I-122)+(b-8), (I-122)+(b-9), (I-122)+(b-10), (I-122)+(b-11), (I-122)+(b-12), (I-122)+(b-13), (I-122)+(b-14), (I-122)+(S3-1), (I-122)+(S3-2), (I-122)+(S3-3), (I-122)+(S3-4), (I-122)+(S3-5), (I-122)+(h-1), (I-122)+(h-2), (I-122)+(V-1), (I-122)+(V-2), (I-122)+(V-3), (I-122)+(V-4), (I-122)+(V-5), (I-122)+(V-6).

(I-123)+(II-0), (I-123)+(II-1), (I-123)+(II-2), (I-123)+(II-3), (I-123)+(II-4), (I-123)+(II-5), (I-123)+(II-6), (I-123)+(II-9), (I-123)+(II-12), (I-123)+(III-1), (I-123)+(III-4), (I-123)+(III-10), (I-123)+(III-11), (I-123)+(IV-1), (I-123)+(IV-2), (I-123)+(IV-3), (I-123)+(IV-4), (I-123)+(IV-5), (I-123)+(b-1), (I-123)+(b-2), (I-123)+(b-3), (I-123)+(b-4), (I-123)+(b-5), (I-123)+(b-6), (I-123)+(b-7), (I-123)+(b-8), (I-123)+(b-9), (I-123)+(b-10), (I-123)+(b-11), (I-123)+(b-12), (I-123)+(b-13), (I-123)+(b-14), (I-123)+(S3-1), (I-123)+(S3-2), (I-123)+(S3-3), (I-123)+(S3-4), (I-123)+(S3-5), (I-123)+(h-1), (I-123)+(h-2), (I-123)+(V-1), (I-123)+(V-2), (I-123)+(V-3), (I-123)+(V-4), (I-123)+(V-5), (I-123)+(V-6).

(I-124)+(II-0), (I-124)+(II-1), (I-124)+(II-2), (I-124)+(II-3), (I-124)+(II-4), (I-124)+(II-5), (I-124)+(II-6), (I-124)+(II-9), (I-124)+(II-12), (I-124)+(III-1), (I-124)+(III-4), (I-124)+(III-10), (I-124)+(III-11), (I-124)+(IV-1), (I-124)+(IV-2), (I-124)+(IV-3), (I-124)+(IV-4), (I-124)+(IV-5), (I-124)+(b-1), (I-124)+(b-2), (I-124)+(b-3), (I-124)+(b-4), (I-124)+(b-5), (I-124)+(b-6), (I-124)+(b-7), (I-124)+(b-8), (I-124)+(b-9), (I-124)+(b-10), (I-124)+(b-11), (I-124)+(b-12), (I-124)+(b-13), (I-124)+(b-14), (I-124)+(S3-1), (I-124)+(S3-2), (I-124)+(S3-3), (I-124)+(S3-4), (I-124)+(S3-5), (I-124)+(h-1), (I-124)+(h-2), (I-124)+(V-1), (I-124)+(V-2), (I-124)+(V-3), (I-124)+(V-4), (I-124)+(V-5), (I-124)+(V-6).

(I-125)+(II-0), (I-125)+(II-1), (I-125)+(II-2), (I-125)+(II-3), (I-125)+(II-4), (I-125)+(II-5), (I-125)+(II-6), (I-125)+(II-9), (I-125)+(II-12), (I-125)+(III-1), (I-125)+(III-4), (I-125)+(III-10), (I-125)+(III-11), (I-125)+(IV-1), (I-125)+(IV-2), (I-125)+(IV-3), (I-125)+(IV-4), (I-125)+(IV-5), (I-125)+(b-1), (I-125)+(b-2), (I-125)+(b-3), (I-125)+(b-4), (I-125)+(b-5), (I-125)+(b-6), (I-125)+(b-7), (I-125)+(b-8), (I-125)+(b-9), (I-125)+(b-10), (I-125)+(b-11), (I-125)+(b-12), (I-125)+(b-13), (I-125)+(b-14), (I-125)+(S3-1), (I-125)+(S3-2), (I-125)+(S3-3), (I-125)+(S3-4), (I-125)+(S3-5), (I-125)+(h-1), (I-125)+(h-2), (I-125)+(V-1), (I-125)+(V-2), (I-125)+(V-3), (I-125)+(V-4), (I-125)+(V-5), (I-125)+(V-6).

(I-126)+(II-0), (I-126)+(II-1), (I-126)+(II-2), (I-126)+(II-3), (I-126)+(II-4), (I-126)+(II-5), (I-126)+(II-6), (I-126)+(II-9), (I-126)+(II-12), (I-126)+(III-1), (I-126)+(III-4), (I-126)+(III-10), (I-126)+(III-11), (I-126)+(IV-1), (I-126)+(IV-2), (I-126)+(IV-3), (I-126)+(IV-4), (I-126)+(IV-5), (I-126)+(b-1), (I-126)+(b-2), (I-126)+(b-3), (I-126)+(b-4), (I-126)+(b-5), (I-126)+(b-6), (I-126)+(b-7), (I-126)+(b-8), (I-126)+(b-9), (I-126)+(b-10), (I-126)+(b-11), (I-126)+(b-12), (I-126)+(b-13), (I-126)+(b-14), (I-126)+(S3-1), (I-126)+(S3-2), (I-126)+(S3-3), (I-126)+(S3-4), (I-126)+(S3-5), (I-126)+(h-1), (I-126)+(h-2), (I-126)+(V-1), (I-126)+(V-2), (I-126)+(V-3), (I-126)+(V-4), (I-126)+(V-5), (I-126)+(V-6).

(I-127)+(II-0), (I-127)+(II-1), (I-127)+(II-2), (I-127)+(II-3), (I-127)+(II-4), (I-127)+(II-5), (I-127)+(II-6), (I-127)+(II-9), (I-127)+(II-12), (I-127)+(III-1), (I-127)+(III-4), (I-127)+(III-10), (I-127)+(III-11), (I-127)+(IV-1), (I-127)+(IV-2), (I-127)+(IV-3), (I-127)+(IV-4), (I-127)+(IV-5), (I-127)+(b-1), (I-127)+(b-2), (I-127)+(b-3), (I-127)+(b-4), (I-127)+(b-5), (I-127)+(b-6), (I-127)+(b-7), (I-127)+(b-8), (I-127)+(b-9), (I-127)+(b-10), (I-127)+(b-11), (I-127)+(b-12), (I-127)+(b-13), (I-127)+(b-14), (I-127)+(S3-1), (I-127)+(S3-2), (I-127)+(S3-3), (I-127)+(S3-4), (I-127)+(S3-5), (I-127)+(h-1), (I-127)+(h-2), (I-127)+(V-1), (I-127)+(V-2), (I-127)+(V-3), (I-127)+(V-4), (I-127)+(V-5), (I-127)+(V-6).

(I-128)+(II-0), (I-128)+(II-1), (I-128)+(II-2), (I-128)+(II-3), (I-128)+(II-4), (I-128)+(II-5), (I-128)+(II-6), (I-128)+(II-9), (I-128)+(II-12), (I-128)+(III-1), (I-128)+(III-4), (I-128)+(III-10), (I-128)+(III-11), (I-128)+(IV-1), (I-128)+(IV-2), (I-128)+(IV-3), (I-128)+(IV-4), (I-128)+(IV-5), (I-128)+(b-1), (I-128)+(b-2), (I-128)+(b-3), (I-128)+(b-4), (I-128)+(b-5), (I-128)+(b-6), (I-128)+(b-7), (I-128)+(b-8), (I-128)+(b-9), (I-128)+(b-10), (I-128)+(b-11), (I-128)+(b-12), (I-128)+(b-13), (I-128)+(b-14), (I-128)+(S3-1), (I-128)+(S3-2), (I-128)+(S3-3), (I-128)+(S3-4), (I-128)+(S3-5), (I-128)+(h-1), (I-128)+(h-2), (I-128)+(V-1), (I-128)+(V-2), (I-128)+(V-3), (I-128)+(V-4), (I-128)+(V-5), (I-128)+(V-6).

(I-129)+(II-0), (I-129)+(II-1), (I-129)+(II-2), (I-129)+(II-3), (I-129)+(II-4), (I-129)+(II-5), (I-129)+(II-6), (I-129)+(II-9), (I-129)+(II-12), (I-129)+(III-1), (I-129)+(III-4), (I-129)+(III-10), (I-129)+(III-11), (I-129)+(IV-1), (I-129)+(IV-2), (I-129)+(IV-3), (I-129)+(IV-4), (I-129)+(IV-5), (I-129)+(b-1), (I-129)+(b-2), (I-129)+(b-3), (I-129)+(b-4), (I-129)+(b-5), (I-129)+(b-6), (I-129)+(b-7), (I-129)+(b-8), (I-129)+(b-9), (I-129)+(b-10), (I-129)+(b-11), (I-129)+(b-12), (I-129)+(b-13), (I-129)+(b-14), (I-129)+(S3-1), (I-129)+(S3-2), (I-129)+(S3-3), (I-129)+(S3-4), (I-129)+(S3-5), (I-129)+(h-1), (I-129)+(h-2), (I-129)+(V-1), (I-129)+(V-2), (I-129)+(V-3), (I-129)+(V-4), (I-129)+(V-5), (I-129)+(V-6).

(I-130)+(II-0), (I-130)+(II-1), (I-130)+(II-2), (I-130)+(II-3), (I-130)+(II-4), (I-130)+(II-5), (I-130)+(II-6), (I-130)+(II-9), (I-130)+(II-12), (I-130)+(III-1), (I-130)+(III-4), (I-130)+(III-10), (I-130)+(III-11), (I-130)+(IV-1), (I-130)+(IV-2), (I-130)+(IV-3), (I-130)+(IV-4), (I-130)+(IV-5), (I-130)+(b-1), (I-130)+(b-2), (I-130)+(b-3), (I-130)+(b-4), (I-130)+(b-5), (I-130)+(b-6), (I-130)+(b-7), (I-130)+(b-8), (I-130)+(b-9), (I-130)+(b-10), (I-130)+(b-11), (I-130)+(b-12), (I-130)+(b-13), (I-130)+(b-14), (I-130)+(S3-1), (I-130)+(S3-2), (I-130)+(S3-3), (I-130)+(S3-4), (I-130)+(S3-5), (I-130)+(h-1), (I-130)+(h-2), (I-130)+(V-1), (I-130)+(V-2), (I-130)+(V-3), (I-130)+(V-4), (I-130)+(V-5), (I-130)+(V-6).

(I-131)+(II-0), (I-131)+(II-1), (I-131)+(II-2), (I-131)+(II-3), (I-131)+(II-4), (I-131)+(II-5), (I-131)+(II-6), (I-131)+(II-9), (I-131)+(II-12), (I-131)+(III-1), (I-131)+(III-4), (I-131)+(III-10), (I-131)+(III-11), (I-131)+(IV-1), (I-131)+(IV-2), (I-131)+(IV-3), (I-131)+(IV-4), (I-131)+(IV-5), (I-131)+(b-1), (I-131)+(b-2), (I-131)+(b-3), (I-131)+(b-4), (I-131)+(b-5), (I-131)+(b-6), (I-131)+(b-7), (I-131)+(b-8), (I-131)+(b-9), (I-131)+(b-10), (I-131)+(b-11), (I-131)+(b-12), (I-131)+(b-13), (I-131)+(b-14), (I-131)+(S3-1), (I-131)+(S3-2), (I-131)+(S3-3), (I-131)+(S3-4), (I-131)+(S3-5), (I-131)+(h-1), (I-131)+(h-2), (I-131)+(V-1), (I-131)+(V-2), (I-131)+(V-3), (I-131)+(V-4), (I-131)+(V-5), (I-131)+(V-6).

(I-132)+(II-0), (I-132)+(II-1), (I-132)+(II-2), (I-132)+(II-3), (I-132)+(II-4), (I-132)+(II-5), (I-132)+(II-6), (I-132)+(II-9), (I-132)+(II-12), (I-132)+(III-1), (I-132)+(III-4), (I-132)+(III-10), (I-132)+(III-11), (I-132)+(IV-1), (I-132)+(IV-2), (I-132)+(IV-3), (I-132)+(IV-4), (I-132)+(IV-5), (I-132)+(b-1), (I-132)+(b-2), (I-132)+(b-3), (I-132)+(b-4), (I-132)+(b-5), (I-132)+(b-6), (I-132)+(b-7), (I-132)+(b-8), (I-132)+(b-9), (I-132)+(b-10), (I-132)+(b-11), (I-132)+(b-12), (I-132)+(b-13), (I-132)+(b-14), (I-132)+(S3-1), (I-132)+(S3-2), (I-132)+(S3-3), (I-132)+(S3-4), (I-132)+(S3-5), (I-132)+(h-1), (I-132)+(h-2), (I-132)+(V-1), (I-132)+(V-2), (I-132)+(V-3), (I-132)+(V-4), (I-132)+(V-5), (I-132)+(V-6).

(I-133)+(II-0), (I-133)+(II-1), (I-133)+(II-2), (I-133)+(II-3), (I-133)+(II-4), (I-133)+(II-5), (I-133)+(II-6), (I-133)+(II-9), (I-133)+(II-12), (I-133)+(III-1), (I-133)+(III-4), (I-133)+(III-10), (I-133)+(III-11), (I-133)+(IV-1), (I-133)+(IV-2), (I-133)+(IV-3), (I-133)+(IV-4), (I-133)+(IV-5), (I-133)+(b-1), (I-133)+(b-2), (I-133)+(b-3), (I-133)+(b-4), (I-133)+(b-5), (I-133)+(b-6), (I-133)+(b-7), (I-133)+(b-8), (I-133)+(b-9), (I-133)+(b-10), (I-133)+(b-11), (I-133)+(b-12), (I-133)+(b-13), (I-133)+(b-14), (I-133)+(S3-1), (I-133)+(S3-2), (I-133)+(S3-3), (I-133)+(S3-4), (I-133)+(S3-5), (I-133)+(h-1), (I-133)+(h-2), (I-133)+(V-1), (I-133)+(V-2), (I-133)+(V-3), (I-133)+(V-4), (I-133)+(V-5), (I-133)+(V-6).

(I-134)+(II-0), (I-134)+(II-1), (I-134)+(II-2), (I-134)+(II-3), (I-134)+(II-4), (I-134)+(II-5), (I-134)+(II-6), (I-134)+(II-9), (I-134)+(II-12), (I-134)+(III-1), (I-134)+(III-4), (I-134)+(III-10), (I-134)+(III-11), (I-134)+(IV-1), (I-134)+(IV-2), (I-134)+(IV-3), (I-134)+(IV-4), (I-134)+(IV-5), (I-134)+(b-1), (I-134)+(b-2), (I-134)+(b-3), (I-134)+(b-4), (I-134)+(b-5), (I-134)+(b-6), (I-134)+(b-7), (I-134)+(b-8), (I-134)+(b-9), (I-134)+(b-10), (I-134)+(b-11), (I-134)+(b-12), (I-134)+(b-13), (I-134)+(b-14), (I-134)+(S3-1), (I-134)+(S3-2), (I-134)+(S3-3), (I-134)+(S3-4), (I-134)+(S3-5), (I-134)+(h-1), (I-134)+(h-2), (I-134)+(V-1), (I-134)+(V-2), (I-134)+(V-3), (I-134)+(V-4), (I-134)+(V-5), (I-134)+(V-6).

(I-135)+(II-0), (I-135)+(II-1), (I-135)+(II-2), (I-135)+(II-3), (I-135)+(II-4), (I-135)+(II-5), (I-135)+(II-6), (I-135)+(II-9), (I-135)+(II-12), (I-135)+(III-1), (I-135)+(III-4), (I-135)+(III-10), (I-135)+(III-11), (I-135)+(IV-1), (I-135)+(IV-2), (I-135)+(IV-3), (I-135)+(IV-4), (I-135)+(IV-5), (I-135)+(b-1), (I-135)+(b-2), (I-135)+(b-3), (I-135)+(b-4), (I-135)+(b-5), (I-135)+(b-6), (I-135)+(b-7), (I-135)+(b-8), (I-135)+(b-9), (I-135)+(b-10), (I-135)+(b-11), (I-135)+(b-12), (I-135)+(b-13), (I-135)+(b-14), (I-135)+(S3-1), (I-135)+(S3-2), (I-135)+(S3-3), (I-135)+(S3-4), (I-135)+(S3-5), (I-135)+(h-1), (I-135)+(h-2), (I-135)+(V-1), (I-135)+(V-2), (I-135)+(V-3), (I-135)+(V-4), (I-135)+(V-5), (I-135)+(V-6).

(I-136)+(II-0), (I-136)+(II-1), (I-136)+(II-2), (I-136)+(II-3), (I-136)+(II-4), (I-136)+(II-5), (I-136)+(II-6), (I-136)+(II-9), (I-136)+(II-12), (I-136)+(III-1), (I-136)+(III-4), (I-136)+(III-10), (I-136)+(III-11), (I-136)+(IV-1), (I-136)+(IV-2), (I-136)+(IV-3), (I-136)+(IV-4), (I-136)+(IV-5), (I-136)+(b-1), (I-136)+(b-2), (I-136)+(b-3), (I-136)+(b-4), (IV-5), (b-5), (I-136)+(b-6), (I-136)+(b-7), (I-136)+(b-8), (I-136)+(b-9), (I-136)+(b-10), (I-136)+(b-11), (I-136)+(b-12), (I-136)+(b-13), (I-136)+(b-14), (I-136)+(S3-1), (I-136)+(S3-2), (I-136)+(S3-3), (I-136)+(S3-4), (I-136)+(S3-5), (I-136)+(h-1), (I-136)+(h-2), (I-136)+(V-1), (I-136)+(V-2), (I-136)+(V-3), (I-136)+(V-4), (I-136)+(V-5), (I-136)+(V-6).

(I-137)+(II-0), (I-137)+(II-1), (I-137)+(II-2), (I-137)+(II-3), (I-137)+(II-4), (I-137)+(II-5), (I-137)+(II-6), (I-137)+(II-9), (I-137)+(II-20), (I-137)+(III-1), (I-137)+(III-4), (I-137)+(III-10), (I-137)+(III-11), (I-137)+(IV-1), (I-137)+(IV-2), (I-137)+(IV-3), (I-137)+(IV-4), (I-137)+(IV-5), (I-137)+(b-1), (I-137)+(b-2), (I-137)+(b-3), (I-137)+(b-4), (I-137)+(b-5), (I-137)+(b-6), (I-137)+(b-7), (I-137)+(b-8), (I-137)+(b-9), (I-137)+(b-10), (I-137)+(b-11), (I-137)+(b-12), (I-137)+(b-13), (I-137)+(b-14), (I-137)+(S3-1), (I-137)+(S3-2), (I-137)+(S3-3), (I-137)+(S3-4), (I-137)+(S3-5), (I-137)+(h-

1), (I-137)+(h-2), (I-137)+(V-1), (I-137)+(V-2), (I-137)+(V-3), (I-137)+(V-4), (I-137)+(V-5), (I-137)+(V-6).

(I-138)+(II-0), (I-138)+(II-1), (I-138)+(II-2), (I-138)+(II-3), (I-138)+(II-4), (I-138)+(II-5), (I-138)+(II-6), (I-138)+(II-9), (I-138)+(II-12), (I-138)+(III-1), (I-138)+(III-4), (I-138)+(III-10), (I-138)+(III-11), (I-138)+(IV-1), (I-138)+(IV-2), (I-138)+(IV-3), (I-138)+(IV-4), (I-138)+(IV-5), (I-138)+(b-1), (I-138)+(b-2), (I-138)+(b-3), (I-138)+(b-4), (I-138)+(b-5), (I-138)+(b-6), (I-138)+(b-7), (I-138)+(b-8), (I-138)+(b-9), (I-138)+(b-10), (I-138)+(b-11), (I-138)+(b-12), (I-138)+(b-13), (I-138)+(b-14), (I-138)+(S3-1), (I-138)+(S3-2), (I-138)+(S3-3), (I-138)+(S3-3-4), (I-138)+(S3-5), (I-138)+(h-1), (I-138)+(h-2), (I-138)+(V-1), (I-138)+(V-2), (I-138)+(V-3), (I-138)+(V-4), (I-138)+(V-5), (I-138)+(V-6).

(I-139)+(II-0), (I-139)+(II-1), (I-139)+(II-2), (I-139)+(II-3), (I-139)+(II-4), (I-139)+(II-5), (I-139)+(II-6), (I-139)+(II-9), (I-139)+(II-12), (I-139)+(III-1), (I-139)+(III-4), (I-139)+(III-10), (I-139)+(III-11), (I-139)+(IV-1), (I-139)+(IV-2), (I-139)+(IV-3), (I-139)+(IV-4), (I-139)+(IV-5), (I-139)+(b-1), (I-139)+(b-2), (I-139)+(b-3), (I-139)+(b-4), (I-139)+(b-5), (I-139)+(b-6), (I-139)+(b-7), (I-139)+(b-8), (I-139)+(b-9), (I-139)+(b-10), (I-139)+(b-11), (I-139)+(b-12), (I-139)+(b-13), (I-139)+(b-14), (I-139)+(S3-1), (I-139)+(S3-2), (I-139)+(S3-3), (I-139)+(S3-4), (I-139)+(S3-5), (I-139)+(h-1), (I-139)+(h-2), (I-139)+(V-1), (I-139)+(V-2), (I-139)+(V-3), (I-139)+(V-4), (I-139)+(V-5), (I-139)+(V-6).

(I-140)+(II-0), (I-140)+(II-1), (I-140)+(II-2), (I-140)+(II-3), (I-140)+(II-4), (I-140)+(II-5), (I-140)+(II-6), (I-140)+(I-140)+(II-12), (I-140)+(III-1), (I-140)+(III-4), (I-140)+(III-10), (I-140)+(III-11), (I-140)+(IV-1), (I-140)+(IV-2), (I-140)+(IV-3), (I-140)+(IV-4), (I-140)+(IV-5), (I-140)+(b-1), (I-140)+(b-2), (I-140)+(b-3), (I-140)+(b-4), (I-140)+(b-5), (I-140)+(b-6), (I-140)+(b-7), (I-140)+(b-8), (I-140)+(b-9), (I-140)+(b-10), (I-140)+(b-11), (I-140)+(b-12), (I-140)+(b-13), (I-140)+(b-14), (I-140)+(S3-1), (I-140)+(S3-2), (I-140)+(S3-3), (I-140)+(S3-4), (I-140)+(S3-5), (I-140)+(h-1), (I-140)+(h-2), (I-140)+(V-1), (I-140)+(V-2), (I-140)+(V-3), (I-140)+(V-4), (I-140)+(V-5), (I-140)+(V-6).

(I-141)+(II-0), (I-141)+(II-1), (I-141)+(II-2), (I-141)+(II-3), (I-141)+(II-4), (I-141)+(II-5), (I-141)+(II-6), (I-141)+(II-9), (I-141)+(II-12), (I-141)+(III-1), (I-141)+(III-4), (I-141)+(III-10), (I-141)+(III-11), (I-141)+(IV-1), (I-141)+(IV-2), (I-141)+(IV-3), (I-141)+(IV-4), (I-141)+(IV-5), (I-141)+(b-1), (I-141)+(b-2), (I-141)+(b-3), (I-141)+(b-4), (I-141)+(b-5), (I-141)+(b-6), (I-141)+(b-7), (I-141)+(b-8), (I-141)+(b-9), (I-141)+(b-10), (I-141)+(b-11), (I-141)+(b-12), (I-141)+(b-13), (I-141)+(b-14), (I-141)+(S3-1), (I-141)+(S3-2), (I-141)+(S3-3), (I-141)+(S3-4), (I-141)+(S3-5), (I-141)+(h-1), (I-141)+(h-2), (I-141)+(V-1), (I-141)+(V-2), (I-141)+(V-3), (I-141)+(V-4), (I-141)+(V-5), (I-141)+(V-6).

(I-142)+(II-0), (I-142)+(II-1), (I-142)+(II-2), (I-142)+(II-3), (I-142)+(II-4), (I-142)+(II-5), (I-142)+(II-6), (I-142)+(II-9), (I-142)+(II-2), (I-142)+(III-1), (I-142)+(III-4), (I-142)+(III-10), (I-142)+(III-11), (I-142)+(IV-1), (I-142)+(IV-2), (I-142)+(IV-3), (I-142)+(IV-4), (I-142)+(IV-5), (I-142)+(b-1), (I-142)+(b-2), (I-142)+(b-3), (I-142)+(b-4), (I-142)+(b-5), (I-142)+(b-6), (I-142)+(b-7), (I-142)+(b-8), (I-142)+(b-9), (I-142)+(b-10), (I-142)+(b-11), (I-142)+(b-12), (I-142)+(b-13), (I-142)+(b-14), (I-142)+(S3-1), (I-142)+(S3-2), (I-142)+(S3-3), (I-142)+(S3-4), (I-142)+(S3-5), (I-142)+(h-1), (I-142)+(h-2), (I-142)+(V-1), (I-142)+(V-2), (I-142)+(V-3), (I-142)+(V-4), (I-142)+(V-5), (I-142)+(V-6).

(I-143)+(II-0), (I-143)+(II-1), (I-143)+(II-2), (I-143)+(II-3), (I-143)+(II-4), (I-143)+(II-5), (I-143)+(II-6), (I-143)+(II-9), (I-143)+(II-12), (I-143)+(III-1), (I-143)+(III-4), (I-143)+(III-10), (I-143)+(III-11), (I-143)+(IV-1), (I-143)+(IV-2), (I-143)+(IV-3), (I-143)+(IV-4), (I-143)+(IV-5), (I-143)+(b-1), (I-143)+(b-2), (I-143)+(b-3), (I-143)+(b-4), (I-143)+(b-5), (I-143)+(b-6), (I-143)+(b-7), (I-143)+(b-8), (I-143)+(b-9), (I-143)+(b-10), (I-143)+(b-11), (I-143)+(b-12), (I-143)+(b-13), (I-143)+(b-14), (I-143)+(S3-1), (I-143)+(S3-2), (I-143)+(S3-3), (I-143)+(S3-4), (I-143)+(S3-5), (I-143)+(h-1), (I-143)+(h-2), (I-143)+(V-1), (I-143)+(V-2), (I-143)+(V-3), (I-143)+(V-4), (I-143)+(V-5), (I-143)+(V-6).

(I-144)+(II-0), (I-144)+(II-1), (I-144)+(II-2), (I-144)+(II-3), (I-144)+(II-4), (I-144)+(II-5), (I-144)+(II-6), (I-144)+(II-9), (I-144)+(II-12), (I-144)+(III-1), (I-144)+(III-4), (I-144)+(III-10), (I-144)+(III-11), (I-144)+(IV-1), (I-144)+(IV-2), (I-144)+(IV-3), (I-144)+(IV-4), (I-144)+(IV-5), (I-144)+(b-1), (I-144)+(b-2), (I-144)+(b-3), (I-144)+(b-4), (I-144)+(b-5), (I-144)+(b-6), (I-144)+(b-7), (I-144)+(b-8), (I-144)+(b-9), (I-144)+(b-10), (I-144)+(b-11), (I-144)+(b-12), (I-144)+(b-13), (I-144)+(b-14), (I-144)+(S3-1), (I-144)+(S3-2), (I-144)+(S3-3), (I-144)+(S3-4), (I-144)+(S3-5), (I-144)+(h-1), (I-144)+(h-2), (I-144)+(V-1), (I-144)+(V-2), (I-144)+(V-3), (I-144)+(V-4), (I-144)+(V-5), (I-144)+(V-6).

(I-145)+(II-0), (I-145)+(II-1), (I-145)+(II-2), (I-145)+(II-3), (I-145)+(II-4), (I-145)+(II-5), (I-145)+(II-6), (I-145)+(II-9), (I-145)+(II-12), (I-145)+(III-1), (I-145)+(III-4), (I-145)+(III-10), (I-145)+(III-11), (I-145)+(IV-1), (I-145)+(IV-2), (I-145)+(IV-3), (I-145)+(IV-4), (I-145)+(IV-5), (I-145)+(b-1), (I-145)+(b-2), (I-145)+(b-3), (I-145)+(b-4), (I-145)+(b-5), (I-145)+(b-6), (I-145)+(b-7), (I-145)+(b-8), (I-145)+(b-9), (I-145)+(b-10), (I-145)+(b-11), (I-145)+(b-12), (I-145)+(b-13), (I-145)+(b-14), (I-145)+(S3-1), (I-145)+(S3-2), (I-145)+(S3-3), (I-145)+(S3-4), (I-145)+(S3-5), (I-145)+(h-1), (I-145)+(h-2), (I-145)+(V-1), (I-145)+(V-2), (I-145)+(V-3), (I-145)+(V-4), (I-145)+(V-5), (I-145)+(V-6).

The safeners (antidotes) of the formula (II)-(VIII) and the compounds of group (B) (b), for example safeners of the preferred groups a) to h), are suitable for reducing phytotoxic effects which may occur when using herbicides (A) in crops of useful plants, but they have no major effect on the activity of these herbicidally active compounds against harmful plants. By virtue of these properties, it is possible to extend the field of application of customary crop protection compositions considerably, for example to crops in which it has hitherto not been possible to employ the herbicides, or only to a limited extent.

Depending on indication and herbicidally active compounds used, the required application rates of the safeners can vary within wide limits and are generally in the range from 0.001 to 5 kg, preferably from 0.005 to 2.5 kg, of active compound per hectare.

The herbicidally active compounds (A) and the safeners (B) can be applied together (for example as a readymix or by the tank mix method) or sequentially in any desired order, for example by atomizing, pouring or spraying, or by broadcasting granules. The weight ratio of herbicide (A):safener (B) may vary within wide limits and is preferably in the range from 1:10 000 to 10 000:1, in particular from 1:1000 to 1000:1. The optimum amounts of herbicide and safener depend in each case on the type of herbicide used and the type of safener used and on the nature and the development stage of the plant stock to be treated and can be determined in each individual case by simple routine preliminary experiments.

Depending on their properties, the safeners (B) contained in the herbicide-safener combination according to the invention can be used for pretreating the seed of the crop plant (for example for seed dressing) or introduced into the seed furrows prior to sowing or used together with the herbicide before or after emergence of the plants. Pre-emergence treatment includes not only the treatment of the area under cultivation (including, if appropriate, water present on the area under cultivation, for example in the case of rice applications) before sowing, but also the treatment of the sown soil which does not yet sustain vegetation. Preferred is the application together with the herbicide. Tank mixes or readymixes may be employed for this purpose.

In a preferred embodiment, the seed (for example grains, seed or vegetative propagation organs, such as tubers or shoot parts with buds) or seedlings are pretreated with the safeners (B), if appropriate in combination with other agrochemically active compounds. For pretreating the seed, the active compounds can be applied to the seed, for example, by dressing, or the active compounds and the seed can be introduced into water or other solvents, and the active compounds can be taken up, for example, by adduct formation or diffusion in a dip process or by swelling or pregermination. For the pretreatment of seedlings, the young plants can be brought into contact with the safeners, if appropriate in the combination with other agrochemically active compounds, for example by spraying, dipping or watering, and then be transplanted and, if appropriate, be subjected to a post-treatment with the herbicides (A).

The treatment of the seed or the seedlings can be carried out using the safeners (B) alone or together with other agrochemically active compounds, such as herbicides, in particular the herbicides (A), fungicides, insecticides or agents for fortifying the plant, for fertilizing or for promoting the swelling and germination processes. Here, the safeners may, after the pretreatment application, be applied once more before, after or together with the herbicides (A). By pretreating the seed or the seedlings, it is possible to achieve better long-term action of the safeners.

Accordingly, the present invention also provides a method for controlling unwanted plants in crops of plants, which method comprises applying the components (A) and (B) of the herbicide-safener combination according to the invention to the plants (for example harmful plants, such as monocotyledonous or dicotyledonous weeds or unwanted crop plants), the seed (for example grains, seeds or vegetative propagation organs, such as tubers or shoot parts with buds) or to the area in which the plants grow (for example the area under cultivation), for example jointly or separately. Here, it is possible to apply one or more safeners (B), preferably one or more, in particular one, compound of the formula (II), (III), (IV), (V), (VI), (VII), (VIII), and/or from the group B (b), before, after or simultaneously with the herbicide(s) (A) to the plants, the seed or the area in which the plants grow (for example the area under cultivation). In a preferred embodiment, the safeners (B) are used for treating the seed.

Unwanted plants are to be understood as meaning all plants growing in locations where they are unwanted. These may be, for example, harmful plants (for example monocotyledonous or dicotyledonous weeds or unwanted crop plants), including, for example, those which are resistant to certain herbicidally active compounds, such as glyphosate, atrazine, glufosinate or imidazolinone herbicides.

Monocotyledonous weeds are, for example, from the genera *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera*. Dicotyledonous weeds are, for example, from the genera *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum, Euphorbia*.

In the process according to the invention, preferably an effective amount of the components (A) and (B) is used for controlling harmful plants in crop plants, for example in farm crops of economic importance, for example monocotyledonous farm crops, such as cereals (for example wheat, barley, rye, oats), rice, corn, millet, or dicotyledonous farm crops, such as sugar beet, oil seed rape, cotton, sunflowers and legumes, for example of the genera *Glycine* (for example *Glycine max.*, such as non-transgenic *Glycine max.* (for example conventional cultivars, such as STS cultivars) or transgenic *Glycine max.* (for example RR-soybeans or LL-soybeans) and crossbreeds thereof), *Phaseolus, Pisum, Vicia* and *Arachis*, or vegetable crops from various botanical groups, such as potato, leek, cabbage, carrot, tomato, onion, and also permanent crops and plantation crops, such as pome fruit and stone fruit, berry fruit, grapevine, Hevea, bananas, sugar cane, coffee, tea, citrus fruit, nut plantations, lawn, palm plantations and forest plantations.

The invention also provides the use of the herbicide-safener combinations according to the invention for controlling unwanted vegetation, preferably in crop plants.

The herbicide-safener combinations according to the invention can be prepared by known processes, for example as mix formulations of the individual components, if appropriate with further active compounds, additives and/or customary formulation auxiliaries, which are then applied in a customary manner diluted with water, or they can be prepared as tank mixes by jointly diluting the individual components, formulated separately or partially formulated separately, with water. It is furthermore possible to apply the individual components, formulated separately or partially formulated separately, at different times (splitting). It is also possible to apply the individual components or the herbicide-safener combinations in a plurality of portions (sequential application), for example pre-emergence applications followed by post-emergence applications or early post-emergence applications followed by medium or late post-emergence applications. Preference is given here to the joint or almost simultaneous application of the active compounds of the combination in question.

The herbicide-safener combination according to the invention can also be employed for controlling harmful plants in crops of known genetically modified plants or genetically modified plants yet to be developed. In general, the transgenic plants have particular advantageous properties, for example resistance to certain crop protection agents, resistance to plant diseases or to caustic agents of plant diseases, such as specific insects or microorganisms, such as fungi, bacteria or viruses. Other particular properties are concerned, for example, with the harvested crop with regard to quantity, quality, storability, composition and specific constituents. Thus, transgenic plants are known which have an increased starch content or a modified starch quality, or which have a different fatty acid composition or amino acid composition of the harvested crop.

Preference is given to the use of the combinations according to the invention in economically important transgenic crops of useful plants and ornamentals, for example of cereals (such as wheat, barley, rye, oats), millet, rice, cassava and corn, or else crops of sugar beet, cotton, soybean, oil seed rape, potato, tomato, pea and other vegetables.

When the combinations according to the invention are used in transgenic crops, effects in addition to the effects to be observed against harmful plants in other crops are frequently found, which are specific for application in the particular transgenic crop, for example a modified or specifically widened spectrum of weeds which can be controlled, modified application rates which may be employed for the application, preferably good combinability with the herbicides to which the transgenic crop is resistant, and an effect on growth and yield of the transgenic crop plants.

Accordingly, the invention also relates to the use of the herbicidally active composition according to the invention for controlling harmful plants in transgenic crop plants or crop plants which are tolerant as a result of selective breeding.

The herbicides (A) and the safeners (B) can, together or separately, be converted into customary formulations, for example for application by atomizing, watering, spraying and seed dressing, such as solutions, emulsions, suspensions, powders, foams, pastes, granules, aerosols, natural compounds or synthetic materials impregnated with active compounds, microcapsules in polymeric compounds. The formulations may comprise the customary auxiliaries and additives.

These formulations are prepared in a known manner, for example by mixing the active compounds with extenders, i.e. liquid solvents, pressurized liquefied gases and/or solid carriers, using, if appropriate, surfactants, i.e. emulsifiers and/or dispersants and/or foam formers.

If the extender used is water, it is also possible to employ, for example, organic solvents as auxiliary solvents. Suitable liquid solvents are essentially: aromatics, such as xylene, toluene, alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide or dimethyl sulfoxide, and also water.

Suitable solid carriers are: for example ammonium salts and ground natural minerals, such as kaolins, clays, talc, chalk, quartz, aftapulgite, montmorillonite or diatomaceous earth, ground synthetic minerals, such as finely divided silica, alumina and silicates; suitable solid carriers for granules are: for example crushed and fractionated natural rocks, such as calcite, marble, pumice, sepiolite and dolomite, and also synthetic granules of inorganic and organic meals, and granules of organic material, such as sawdust, coconut shells, corn cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, for example alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90% by weight.

The herbicides (A) and the safeners (B), as such or in their formulations, including as a mixture with other agrochemically active compounds, such as known herbicides, can be used for controlling unwanted vegetation, for example for controlling weeds or for controlling unwanted crop plants, readymixes or tank mixes, for example, being possible.

Also possible are mixtures with other known active compounds, such as fungicides, insecticides, acaricides, nematicides, safeners, bird repellents, plant nutrients and substances which improve the soil structure, and also formulation auxiliaries and additives customary in crop protection.

The herbicides (A) and the safeners (B) can be applied as such, in the form of their formulations or the use forms prepared therefrom by further dilution, such as ready-to-use solutions, suspensions, emulsions, powders, pastes and granules. Application is carried out in a customary manner, for example by watering, spraying, atomizing, broadcasting.

The active compounds can be applied to the plants, to parts of the plants, to the seed or to the area under cultivation (soil of a field) preferably to the seed or the green plants and parts of plants and, if appropriate, additionally to the soil of the field. One possible use is the joint application of the active compounds in the form of tank mixes, where the concentrated formulations of the individual active compounds, in optimized formulations, are jointly mixed with water in the tank and the resulting spray liquor is applied.

A joint formulation of the combination according to the invention of active compounds (A) and (B) has the advantage of being easier to apply since the quantities of the components are already present in the correct ratio to one another. Moreover, the auxiliaries in the formulation can be matched optimally to one another.

Suitable combination partners for the herbicide-safener combination according to the invention in mix formulations or in the tank mix are, for example, known agrochemically active compounds, such as herbicides, fungicides or insecticides, as described, for example, in Weed Research 26, 441-445 (1986), or "The Pesticide Manual", 13th edition, The British Crop Protection Council, 2003, and the literature cited therein. The following active compounds, for example, may be mentioned as herbicides known from the literature which can be combined with the mixtures according to the invention (note: the compounds are referred to either by the "common name" according to the International Organization for Standardization (ISO) or by the chemical name, if appropriate together with a customary code number, and include in each case all use forms, such as acids, salts, esters and isomers, such as stereoisomers and optical isomers. One and in some cases a plurality of application forms is/are mentioned):

2,4-D, acetochlor, acifluorfen, acifluorfen-sodium, aclonifen, alachlor, alloxydim, alloxydim-sodium, ametryn, amicarbazone, amidosulfuron, aminopyralid, amitrole, anilofos, asulam, atrazine, azafenidin, azimsulfuron, beflubutamid, benazolin, benazolin-ethyl, benfuresate, bensulfuron-methyl, bentazone, benzfendizone, benzobicyclon, benzofenap, bifenox, bilanafos, bispyribac-sodium, bromacil, bromobutide, bromofenoxim, bromoxynil, butachlor, butafenacil, butenachlor, butralin, butroxydim, butylate, cafenstrole, carbetamide, carfentrazone-ethyl, chlomethoxyfen, chloridazon, chlorimuron-ethyl, chlornitrofen, chlorotoluron, chlorsulfuron, cinidon-ethyl, cinmethylin, cinosulfuron, clefoxydim, clethodim, clodinafop-propargyl, clomazone, clomeprop, clopyralid, cloransulam-methyl, cumyluron, cyanazine, cyclosulfamuron, cycloxydim, cyhalofop-butyl, desmedipham, dicamba, dichlobenil, dichlorprop, dichlorprop-p, diclofop-methyl, diclosulam, difenzoquat, diflufenican, diflufenzopyr, dikegulac-sodium, dimefuron, dimepiperate, dimethachlor, dimethametryn, dimethenamid, triaziflam, diquat-dibromide, dithiopyr, diuron, dymron, EPTC, esprocarb, ethalfluralin, ethametsulfuron-methyl, ethofumesate, ethoxyfen, ethoxysulfuron, etobenzanid, fenoxaprop-ethyl, fenoxaprop-p-ethyl, fentrazamide, flamprop-M-isopropyl, flamprop-M-methyl, flazasulfuron, florasulam, fluazifop, fluazifop-butyl, fluazifop-butyl, fluazolate, flucarbazone-sodium, flucetosulfuron, fluchloralin, flufenacet, flufenpyr, flumetsulam, flumiclorac-pentyl, flumioxazin, fluometuron, fluorochloridone, fluoroglycofen-ethyl, flupoxam, flupyrsulfuron-methyl-sodium, fluridone, fluroxypyr, fluroxypyr-butoxypropyl, fluroxypyr-meptyl, flurprimidol, flurtamone, fluthiacet-methyl, fomesafen, foramsulfuron, glufosinate, glufosinate-ammonium, glyphosate, halosulfuron-methyl, haloxyfop, haloxyfop-ethoxyethyl, haloxyfop-methyl, haloxyfop-P-methyl, hexazinone, imazamethabenz-methyl, imazamox, imazapic, imazapyr, imazaquin, imazethapyr, imazosulfuron, indanofan, iodosulfuron-methyl-natrium, ioxynil, isoproturon, isouron, isoxaben, isoxachlortole, isoxaflutole, ketospiradox, lactofen, lenacil, linuron, MCPA, mecoprop, mecoprop-P, mefenacet, mesosulfuron-methyl, mesotrione, metamifop, metamitron, metazachlor, methabenzthiazuron, methyldymron, metobromuron, metolachlor, metosulam, metoxuron, metribuzin, metsulfuron-methyl, molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, penoxsulam, pentoxazone, pethoxamid, phenmedipham, picloram, picolinafen, pinoxaden, piperophos, pretilachlor, primisulfuron-methyl, profluazol, profoxydim, prometryn, propachlor, propanil, propaquizafop, propisochlor, propoxycarbazone-sodium, propyzamide, prosulfocarb, prosulfuron, pyraclonil, pyraflufen-ethyl, pyrazolate, pyrazosulfuron-ethyl, pyrazoxyfen, pyribenzoxim, pyributicarb, pyridafol, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sethoxydim, simazine, simetryn, S-metolachlor, sulcotrione, sulfentrazone, sulfometuron-methyl, sulfosate, sulfosulfuron, tebuthiuron, tepraloxydim, terbuthylazine, terbutryn, thenylchlor, thiazopyr, thifensulfuron-methyl, thiobencarb, tiocarbazil, tralkoxydim, triallate, triasulfuron, tribenuron-methyl, triclopyr, tridiphane, trifloxysulfuron, trifluralin, triflusulfuron-methyl and tritosulfuron.

For application, formulations which are present in a commercial form can, if appropriate, be diluted in a customary manner using, for example, water. Preparations in the form of dusts, soil granules and granules for broadcasting and also sprayable solutions are usually not diluted any further with further inert substances prior to the application.

BIOLOGICAL EXAMPLES

1. Pre-emergence Action Against Weeds

Seeds or rhizome pieces of monocotyledonous and dicotyledonous weed plants were placed in sandy loam soil in cardboard pots and covered with soil. The active compounds (A) and (B), formulated in the form of wettable powders or emulsion concentrates, were then applied to the surface of the covering soil in various dosages as an aqueous suspension or emulsion using a water application rate of 600 to 800 l/ha (converted).

After the treatment, the pots were placed in a greenhouse and kept under good growth conditions for the weeds. Optical scoring of the damage to the plants or emerged plants was carried out after emergence of the test plants after a trial period of 3 to 4 weeks, in comparison to untreated controls. As shown by the results, the tested herbicide-safener combinations have good herbicidal pre-emergence activity against a broad spectrum of weed grasses and broad-leaved weeds. For example, the herbicide-safener combinations of the compounds Nos. I-1, I-3, I-8, I-9, I-10, I-11, I-12, I-14, I-21, I-22, I-23, I-29, I-30, I-51, I-52, I-60, I-70, I-142, I-143, I-145 and other compounds from Table 1 with the safeners dymron (b-14), fenclorim (b-11), cumyluron (b-4), isoxadifen-ethyl (II-9), mefenpyr-diethyl (II-1), cloquintocet-mexyl (III-1), S3-1, h-1, h-2, h-3, dietholate (b-7), disulfoton (b-5), 1,8-naphthalic anhydride (b-1), fluxofenim (b-10), dichlormid (IV-1), benoxacor (IV-2), flurazole (b-12) and R-29148 (IV-4) have very good herbicidal activity against harmful plants such as Sinapis alba, Chrysanthemum segetum, Avena sativa, Stellaria media, Echinochloa crus-galli, Lolium multiflorum, Setaria viridis, Abutilon theophrasti, Amaranthus retroflexus and Panicum miliaceum when applied by the pre-emergence method at an application rate of 100 g or less of herbicide (A) per hectare.

2. Post-emergence Action Against Weeds

Seeds or rhizome pieces of monocotyledonous and dicotyledonous weeds were placed into sandy loam soil in plastic pots, covered with soil and grown in a greenhouse under good growth conditions. Three weeks after sowing, the test plants were treated at the three-leaf stage. The compounds according to the invention, formulated as wettable powders or as emulsion concentrates, were sprayed onto the green parts of the plants at various dosages using a water application rate of 600 to 800 l/ha (converted). The test plants were stood in the greenhouse under optimum growth conditions for about three to four weeks, and the action of the preparations was then scored visually in comparison to untreated controls. Post-emergence, too, the herbicide-safener combinations according to the invention have good herbicidal activity against a broad spectrum of economically important weed grasses and broad-leaved weeds. For example, the herbicide-safener combinations of the compounds Nos. I-1, I-3, I-8, I-9, I-10, I-11, I-12, I-14, I-21, I-22, I-23, I-29, I-30, I-51, I-52, I-60, I-70, I-142, I-143, I-145 and other compounds from Table 1 with the safeners dymron (b-14), fenclorim (b-11), cumyluron (b-4), isoxadifen-ethyl (II-9), mefenpyr-diethyl (II-1), cloquintocet-mexyl (III-1), S3-1, h-1, h-2, h-3, dietholate (b-7), disulfoton (b-5), 1,8-naphthalic anhydride (b-1), fluxofenim (b-10), dichlormid (IV-1), benoxacor (IV-2), flurazole (b-12) and R-29148 (IV-4) have very good herbicidal activity against harmful plants such as Sinapis alba, Echinochloa crus-galli, Lolium multiflorum, Chrysanthemum segetum, Setaria viridis, Abutilon theophrasti, Amaranthus retroflexus, Panicum miliaceum and Avena sativa when applied by the post-emergence method at an application rate of 100 g or less of herbicide (A) per hectare.

3. Compatibility with Crop Plants

In further greenhouse trials, seeds of a relatively large number of crop plants and weeds were placed into sandy loam soil and covered with soil. Some of the pots were immediately treated as described in Section 1, the others were placed in a greenhouse until the plants had developed two to three true leaves and were then sprayed with various dosages of the herbicide-safener combinations according to the invention, as described in Section 2. Four to five weeks after the application and standing time in the greenhouse, it was established by visual scoring that the herbicide-safener combinations tested, for example of compounds Nos. 1-1, I-3, I-8, I-9, I-10, I-11, I-12, I-14, I-21, I-22, I-23, I-29, I-30, I-51, I-52, I-60, I-70, I-142, I-143, I-145 and other compounds from Table 1 with the safeners dymron (b-14), fenclorim (b-11), cumyluron (b-4), isoxadifen-ethyl (II-9), mefenpyr-diethyl (II-1), cloquintocet-mexyl (III-1), S3-1, h-1, h-2, h-3, dietholate (b-7), disulfoton (b-5), 1,8-naphthalic anhydride (b-1), fluxofenim (b-10), dichlormid (IV-1), benoxacor (IV-2), flurazole (b-12) and R-29148 (IV-4) did not cause any damage to crop plants such as cotton, oil seed rape, sugar beet and Gramineae crops such as barley, wheat, rye, millet, corn or rice when applied by the pre-emergence method or the post-emergence method. Application of a combination of 30 g/ha of compound (I-9) with 100 g of isoxadifen-ethyl (II-9), for example, does not cause any damage to corn crops.

The invention claimed is:

1. A herbicide-safener combination, comprising
(A) one or more compounds of the formula (I) or salts thereof

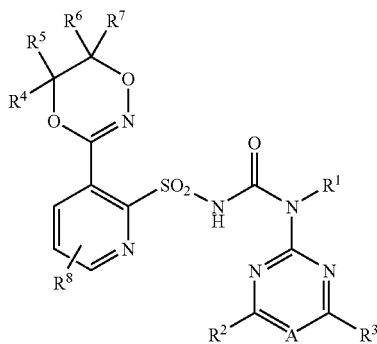

in which
A is or a $CR^{11}$ grouping,
where
$R^{11}$ is hydrogen,
$R^1$ is hydrogen or an optionally substituted radical from the group consisting of alkyl, alkoxy, alkoxyalkyl, alkenyl, akynyl, cycloalkyl, cycloalkylalkyl, aralkyl and aryl,
$R^2$ is hydrogen, halogen or in each case optionally halogen-substituted alkyl, alkoxy, alkylthio, alkylamino or dialkylamino having in each case 1 to 6 carbon atoms,
$R^3$ is hydrogen, halogen or in each case optionally halogen-substituted alkyl, alkoxy, alkylthio, alkylamino or dialkylamino having in each case 1 to 6 carbon atoms,
$R^4$-$R^7$ independently of one another are hydrogen, halogen, cyano, thiocyanato or in each case optionally halogen-substituted alkyl, alkoxy, alkylthio, alkylsulfinyl, alkylsulfonyl, alkylamino, alkylcarbonyl, alkoxycarbonyl, alkylaminocarbonyl having in each case 1 to 3 carbon atoms,
$R^8$ is hydrogen, halogen, cyano, thiocyanato or in each case optionally halogen-substituted alkyl, alkoxy, alkylthio, alkylsulfinyl, alkylsulfonyl, alkylamino, alkylcarbonyl, alkoxycarbonyl, alkylaminocarbonyl having in each case 1 to 3 carbon atoms,
where in the radicals mentioned above the alkyl and alkylene groups may in each case contain 1 to 6 carbon atoms, the alkenyl and alkynyl groups may in each case contain 2 to 6 carbon atoms, the cycloalkyl groups may in each case contain 3 to 6 carbon atoms and the aryl groups may in each case contain 6 or 10 carbon atoms; and
(B) one or more safeners.

2. The herbicide-safener combination as claimed in claim 1 in which in the compound of the formula (I)

A is a CH grouping,
$R^1$ is hydrogen or an optionally halogen-substituted radical from the group consisting of alkyl, alkoxy, alkoxyalkyl, alkenyl and alkynyl having in each case up to 3 carbon atoms,
$R^2$ is hydrogen, halogen or in each case halogen-substituted alkyl, alkoxy, alkylthio, alkylamino or dialkylamino having in each case 1 to 3 carbon atoms in the alkyl radicals,
$R^3$ is hydrogen, halogen or in each case halogen-substituted alkyl, alkoxy, alkylthio, alkylamino or dialkylamino having in each case 1 to 3 carbon atoms in the alkyl radicals,
$R^4$-$R^7$ independently of one another are hydrogen, halogen, cyano, thiocyanato or in each case optionally halogen-substituted alkyl, alkoxy, alkylthio, alkylsulfinyl, alkylsulfonyl, alkylamino, alkylcarbonyl, alkoxycarbonyl, or alkylaminocarbonyl having in each case 1 to 3 carbon atoms in the alkyl radicals,
$R^8$ is hydrogen, halogen, cyano, thiocyanato or in each case optionally halogen-substituted alkyl, alkoxy, alkylthio, alkylsulfinyl, alkylsulfonyl, alkylamino, alkylcarbonyl, alkoxycarbonyl or alkylaminocarbonyl having in each case 1 to 3 carbon atoms in the alkyl radicals.

3. The herbicidal-safener combination as claimed in claim 1 in which the safener(s) (B) is/are selected from the group consisting of: dymron (b-14), fenclorim (b-11), cumyluron (b-4), isoxadifen-ethyl (II-9), mefenpyr-diethyl (II-1), cloquintocet-mexyl (III-1), 4-cyclopropylaminocarbonyl-N-(2-methoxybenzoyl)benzenesulfonamide (S3-1), 1-[4-(N-2-methoxybenzoylsulfamoyl)phenyl]-3-methylurea (h-1), 1-[4-(N-2-methoxy-benzoylsulfamoyl)phenyl]-3,3-dimethylurea (h-2), 1-[4-(N-4,5-dimethyl-benzoylsulfamoyl)phenyl]-3-methylurea (h-3), dietholate (b-7), disulfoton (b-5), 1,8-naphthalic anhydride (b-1), fluxofenim (b-10), dichlormid (IV-1), benoxacor (IV-2), flurazole (b-12), and R-29148 (IV-4).

4. The herbicide-safener combination as claimed in claim 1, additionally comprising one or more further agrochemically active compounds and/or additives and formulation auxiliaries customary in crop protection.

5. A method for controlling unwanted plants, in which the components (A) and (B) of the herbicide-safener combination as claimed in claim 1 are applied together or separately to the plants, the seed or the area on which the plants grow.

6. The method as claimed in claim 5, wherein the crop plants are selected from the group consisting of: farm crops, vegetable crops, permanent crops and plantation crops.

7. The method as claimed in claim 5, wherein the crop plants are transgenic or tolerant owing to selection breeding.

8. A method of using the herbicide-safener combination as defined in claim 1 for controlling harmful plants comprising the step of applying the herbicide-safener combination to said harmful plants.

9. A method according to claim 8, wherein said harmful plants are located in crop plants.

10. A method of using the herbicide-safener combination as defined in claim 1, for controlling harmful plants comprising the step of applying the herbicide-safener combination to one or more seeds of the harmful plants.

11. A method of using the herbicide-safener combination as defined in claim 1, for controlling harmful plants comprising the step of applying the herbicide-safener combination to the area in which the harmful plants are growing.

12. A method of using the herbicide-safener combination as defined in claim 1, for controlling harmful plants comprising the step of applying the herbicide-safener combination to the area in which it is desired to control the growth of the harmful plants.

13. A method for controlling unwanted plants according to claim 5, wherein said unwanted plants are located in crop plants.

14. The herbicide-safener combination of claim 1 wherein said one or more compounds of Formula (I), or salts thereof, are selected from the group consisting of compounds of Formula (I), or salt thereof, in which
  A is a CH grouping,
  $R^1$ is hydrogen or methyl,
  $R^2$ is methoxy, ethoxy, methyl, ethyl, trifluoromethyl, difluoromethoxy, chloro, methylamino or dimethylamino,
  $R^3$ is methoxy, ethoxy, trifluoroethoxy, difluoromethoxy, methyl, ethyl trifluoromethyl, chloro, methylamino or dimethylamino,
  $R^4$-$R^7$ independently of one another are hydrogen,
  $R^8$ is hydrogen.

15. The herbicide-safener combination as claimed in claim 14, wherein said one or more compounds of Formula (I), or salts thereof, are selected from the group consisting of compounds of Formula (I), or salt thereof, in which
  A is a CH grouping,
  $R^1$ is hydrogen,
  $R^2$ is methoxy,
  $R^3$ is methoxy or chloro,
  $R^4$-$R^7$ independently of one another are hydrogen,
  $R^8$ is hydrogen.

16. The herbicide-safener combination as claimed in claim15, wherein said one or more compounds of Formula (I), or salts thereof, is the compound of Formula (I), or sodium salt thereof, wherein
  A is a CH grouping,
  $R^1$ is hydrogen,
  $R^2$ is methoxy,
  $R^3$ is methoxy,
  $R^4$-$R^7$ independently of one another are hydrogen,
  $R^8$ is hydrogen.

17. A herbicide-safener combination of claim 1, wherein said safener(s) (B) is/are selected from the group consisting of: isoxadifen-ethyl (II-9), 4-cyclopropylamino carbonyl-N-(2-methoxybenzoyl)benzenesulfonamide (S3-1), mefenpyr-diethyl (II -1), and cloquintocet-mexyl (III-1).

18. The herbicide-safener combination of claim 1 wherein said one or more compounds of Formula (I), or salts thereof, are selected from the group consisting of compounds of Formula (I), or salts thereof in which
  A is a CH grouping,
  $R^1$ is hydrogen or methyl,
  $R^2$ is methoxy, ethoxy, methyl, ethyl, trifluoromethyl, difluoromethoxy, chloro, methylamino or dimethylamino,
  $R^3$ is methoxy, ethoxy, trifluoroethoxy, difluoromethoxy, methyl, ethyl, trifluoromethyl, chloro, methylamino or dimethylamino,
  $R^4$-$R^7$ independently of one another are hydrogen,
  $R^8$ is hydrogen; and
  said safener(s) (B) is/are selected from the group consisting of: dymron (b-14), fenclorim (b-11), cumyluron (b-4), isoxadifen-ethyl (II -9), mefenpyr-diethyl (II-1), cloquintocet-mexyl (III-1), 4-cyclopropylaminocarbonyl-N-(2-methoxybenzoyl)benzenesulfonamide (S3-1), 1 -[4-(N-2-methoxybenzoylsulfamoyl)phenyl]-3-methylurea (h-1), 1-[4-(N-2-methoxy-benzoylsulfamoyl)phenyl]-3,3-dimethylurea (h-2), 1[4-(N-4,5-dimethylbenzoylsulfamoyl)phenyl]-3-methylurca (h-3), dietholate (b-7), disulfoton (b-5), 1,8-naphthalic anhydride (b-1), fluxofenim (b-10), dichlormid (IV-1), benoxacor (IV-2), flurazole (b-12), and R-29148 (IV-4).

19. The herbicide-safener combination of claim 18, wherein said one or more compounds of Formula (I), or salts thereof, are selected from the group consisting of compounds of Formula (I), or salts thereof in which
  A is a CU grouping,
  $R^1$ is hydrogen,
  $R^2$ is methoxy,
  $R^3$ is methoxy or chloro,
  $R^4$-$R^7$ independently of one another are hydrogen,
  $R^8$ is hydrogen.

20. The herbicide-safener combination of claim 19, wherein said one or more compounds of Formula (I), or salts thereof is the compound of Formula (I), or sodium salt thereof, wherein
  A is a CH grouping,
  $R^1$ is hydrogen,
  $R^2$ is methoxy,
  $R^3$ is methoxy,
  $R^4$-$R^7$ independently of one another are hydrogen,
  $R^8$ is hydrogen.

21. The herbicide-safener combination of claim 18, wherein said safener(s) (B) is/are selected from the group consisting of: isoxadifen-ethyl (II -9), 4-cyclopropylaminocarbonyl-N-(2-methoxybenzoyl)benzenesulfonamide (S3-1), mefenpyr-diethyl (II-1), and cloquintocet-mexyl (III -1).

\* \* \* \* \*

UNITED STATES PATENT AND TRADEMARK OFFICE
CERTIFICATE OF CORRECTION

PATENT NO. : 7,563,749 B2  Page 1 of 1
APPLICATION NO. : 11/090985
DATED : July 21, 2009
INVENTOR(S) : Martin Hills et al.

It is certified that error appears in the above-identified patent and that said Letters Patent is hereby corrected as shown below:

In the Claims:

In Claim 19, in column 56, on line 26, "CU grouping" should read -- CH grouping --.

Signed and Sealed this

Twenty-second Day of September, 2009

David J. Kappos
*Director of the United States Patent and Trademark Office*